US011732273B2

(12) United States Patent
Gurumurthy et al.

(10) Patent No.: US 11,732,273 B2
(45) Date of Patent: Aug. 22, 2023

(54) METHODS AND COMPOSITIONS FOR IN SITU GERMLINE GENOME ENGINEERING

(71) Applicants: BOARD OF REGENTS OF THE UNIVERSITY OF NEBRASKA, Lincoln, NE (US); TOKAI UNIVERSITY EDUCATIONAL SYSTEM, Tokyo (JP)

(72) Inventors: Channabasavaiah Gurumurthy, Omaha, NE (US); Masato Ohtsuka, Kanagawa (JP); Masahiro Sato, Kagoshima (JP)

(73) Assignees: Board of Regents of the University of Nebraska, Lincoln, NE (US); Tokai University Educational System, Tokyo (JP)

( * ) Notice: Subject to any disclaimer, the term of this patent is extended or adjusted under 35 U.S.C. 154(b) by 593 days.

(21) Appl. No.: 16/799,398

(22) Filed: Feb. 24, 2020

(65) Prior Publication Data
US 2020/0263198 A1    Aug. 20, 2020

Related U.S. Application Data

(63) Continuation-in-part of application No. PCT/US2018/047748, filed on Aug. 23, 2018.

(60) Provisional application No. 62/549,644, filed on Aug. 24, 2017.

(51) Int. Cl.
| | |
|---|---|
| *C12N 5/00* | (2006.01) |
| *C12N 15/85* | (2006.01) |
| *C12N 5/071* | (2010.01) |
| *C12N 9/22* | (2006.01) |
| *C12N 15/113* | (2010.01) |
| *A01K 67/027* | (2006.01) |
| *C12N 15/90* | (2006.01) |

(52) U.S. Cl.
CPC .......... *C12N 15/85* (2013.01); *A01K 67/0275* (2013.01); *C12N 5/0608* (2013.01); *C12N 5/0682* (2013.01); *C12N 9/22* (2013.01); *C12N 15/113* (2013.01); *C12N 15/907* (2013.01); *A01K 2227/105* (2013.01); *A01K 2267/03* (2013.01); *C12N 2310/20* (2017.05); *C12N 2800/80* (2013.01)

(58) Field of Classification Search
CPC .... C12N 15/85; C12N 5/0608; C12N 5/0682; C12N 9/22; C12N 15/113; C12N 15/907; C12N 2310/20; C12N 2800/80; A01K 67/0275; A01K 2227/105; A01K 2267/03
See application file for complete search history.

(56) References Cited

U.S. PATENT DOCUMENTS

| | | | |
|---|---|---|---|
| 2012/0202985 A1* | 8/2012 | Misaghi ............ | A01K 67/0275 800/9 |
| 2014/0170753 A1 | 6/2014 | Zhang | |
| 2014/0234972 A1 | 8/2014 | Zhang | |

FOREIGN PATENT DOCUMENTS

WO    2016/196887 A1    12/2016

OTHER PUBLICATIONS

Sato in "Intraoviductal Introduction of Plasmid DNA and Subsequent Electroporation for Efficient In Vivo Gene Transfer to Murine Oviductal Epithelium" (Molecular Reproduction and Development 2005 vol. 71: pp. 321-330). (Year: 2005).*
Gurumurthy et al. in "GONAD: a novel CRISPR/Cas9 genome editing method that does not require ex vivo handling of embryos" (Curr Protoc Hum Genet, published Jan. 1, 2017; vol. 88: pp. 1-17). (Year: 2017).*
Takahashi et al in "GONAD: Genome-editing via Oviductal Nucleic Acids Delivery system: a novel microinjection independent genome engineering method in mice" (Scientific Reports, published Jun. 22, 2015; vol. 5, No. 11406: pp. 1-11). (Year: 2015).*
Peng et al (J.Reprod. Dev. vol. 61, No. 6: pp. 559-564, published 2015). (Year: 2015).*
Kaneko et al in "Simple knockout by electroporation of engineered endonucleases into intact rat embryos" (Scientific Reports vol. 4: No. 6382: pp. 1-5; published Oct. 1, 2014). (Year: 2014).*
Hur et al "Targeted mutagenesis in mice by electroporation of Cpf1 ribonucleoproteins" (Nature Biotechnology vol. 34, No. 8, Aug. 2016, pp. 807-808). (Year: 2016).*
Sato et al (Biology Direct 2016 vol 11: No. 16; pp. 1-12). (Year: 2016).*
Hashimoto & Takemoto (Scientific Reports vol. 5: 11315 published Jun. 11, 2015, pp. 1-7). (Year: 2015).*
Qin W, Dion SL, Kutny PM, Zhang Y, Cheng AW, Jillette NL, et al. Efficient CRISPR/Cas9-mediated genome editing in mice by zygote electroporation of nuclease. Genetics 2015;200:423-30.
Quadros RM, Miura H, Harms DW, Akatsuka H, Sato T, Aida T, et al. Easi-CRISPR: a robust method for one-step generation of mice carrying conditional and insertion alleles using long ssDNA donors and CRISPR ribonucleoproteins. Genome Biol. 2017;18:92.

(Continued)

*Primary Examiner* — Catherine S Hibbert
(74) *Attorney, Agent, or Firm* — Quarles & Brady LLP

(57) ABSTRACT

Disclosed are methods and compositions for in situ germline genome engineering. The disclosed methods and compositions may be utilized for germline genome engineering in a subject having a reproductive organ containing a fertilized zygote, via: (i) isolating or obtaining the reproductive organ from the subject after a time period following insemination of the subject; (ii) introducing a reagent composition into the reproductive organ, the reagent composition comprising a nuclease system and/or an exogeneous polynucleotide; and (iii) electroporating the reproductive organ.

11 Claims, 38 Drawing Sheets

Specification includes a Sequence Listing.

(56) References Cited

OTHER PUBLICATIONS

Robbins et al., Viral Vectors for Gene Therapy. Phamacology & Therapeutics. 80(1) 35-47 (1998).
Schini S. A., B. D. Bavister, Two-cell block to development of cultured hamster embryos is caused by phosphate and glucose. Biol. Reprod. 39, 1183-1192 (1988).
Shmakov et al., Discovery and Functional Characterization of Diverse Class 2 CRISPR-Cas Systems. Molecular Cell 60:1-13 (2015).
Takahashi G, Gurumurthy CB, Wada K, Miura H, Sato M, Ohtsuka M. GONAD: Genome-editing via Oviductal Nucleic Acids Delivery system: a novel microinjection independent genome engineering method in mice. Sci Rep. 2015;5:11406.
Takano H., R. Yanagimachi, U. A. Urch, Evidence that acrosin activity is important for the development of fusibility of mammalian spermatozoa with the oolemma: inhibitor studies using the golden hamster. Zygote 1, 79-91 (1993).
Tesarik J., J. Drahorad, J. Peknicova, Subcellular immunochemical localization of acrosin in human spermatozoa during the acrosome reaction and zona pellucida penetration. Fertil. Steril 50, 133-141 (1988).
Wada K, Maeda YY, Watanabe K, Oshio T, Ueda T, Takahashi G, et al. A deletion in a cis element of Foxe3 causes cataracts and microphthalmia in rct mice. Mamm Genome. 2011;22:693-702.
Wang H, Yang H, Shivalila CS, Dawlaty MM, Cheng AW, Zhang F, et al. One-step generation of mice carrying mutations in multiple genes by CRISPR/Cas-mediated genome engineering. Cell 2013;153:910-8.
Whittaker D., "Hamster" in The UFAW Handbook on the Care and Management of Laboratory Animals, P. Trevor, Ed. (Blackwell Science Ltd., Oxford, 1999), vol. 1, pp. 356-366.
Kamagata K., A. Honda, S. I. Kashiwabara, T. Baba, Difference of acrosomal serine protease system between mouse and other rodent sperm. Dev. Genet. 25, 115-122 (1999).
Yanagida K., R. Yanagimachi, S. D. Perreault, R. G. Kleinfeld, Thermostability of sperm nuclei assessed by microinjection into hamster oocytes. Biol. Reprod. 44, 440-447 (1991).
Yanagimachi R., "Mammalian fertilization" in the Physiology of Reproduction, N. J. Knobil E, Ed. (Raven Press, New York, 1994), pp. 189-317.
Yanagimachi R., M. C. Chang, Fertilization of hamster eggs in vitro. Nature 200, 281-282 (1963).
Yanagimachi R., R. J. Teichman, Cytochemical demonstration of acrosomal proteinase in mammalian and avian spermatozoa by a silver proteinate method. Biol. Reprod. 6, 87-97 (1972).
Yokoyama T, Silversides DW, Waymire KG, Kwon BS, Takeuchi T, Overbeek PA. Conserved cysteine to serine mutation in tyrosinase is responsible for the classical albino mutation in laboratory mice. Nucleic Acids Res. 1990;18:7293-8.
Yu H, Zhang VW. Precision medicine for continuing phenotype expansion of Human Genetic diseases. Biomed Res Int. 2015;2015:745043.
Yunes R., J. Melendez, M. Valdivia, C. Barros, Golden hamster perivitelline spermatozoa do not show proacrosin/acrosin at the inner acrosomal membrane. Biol. Res. 25, 91-93 (1992).
Zetsche B, Gootenberg JS, Abudayyeh OO, Slaymaker IM, Makarova KS, Essletzbichler P, et al. Cpf1 is a single RNA-guided endonuclease of a class 2 CRISPR-Cas system. Cell. 2015;163:759-71.
Abe H, Kamimura K, Kobayashi Y, Ohtsuka M, Miura H, Ohashi R, et al. Effective prevention of liver fibrosis by liver-targeted hydrodynamic gene delivery of matrix metalloproteinase-13 in a rat liver fibrosis model. Mol Ther Nucleic Acids. 2016; 5:e276.
Aida T, Chiyo K, Usami T, Ishikubo H, Imahashi R, Wada Y, et al. Cloning-free CRISPR/Cas system facilitates functional cassette knock-in in mice. Genome Biol. 2015;16:87.
Austin C. R., M. W. H. Bishop, Role of the rodent acrosome and perforatorium in fertilisation Proc. R. Soc. Lond. B. Biol. Sci. 148, 241-248 (1958).

Baba T., S. Azuma, S. Kashiwabara, Y. Toyoda, Sperm from mice carrying a targeted mutation of the acrosin gene can penetrate the oocyte zona pellucida and effect fertilization. J. Biol. Chem. 269, 31845-31849 (1994).
Bavister B. D., R. Yanagimachi, The effects of sperm extracts and energy sources on the motility and acrosome reaction of hamster spermatozoa in vitro. Biol. Reprod. 16, 228-237 (1977).
Behringer R, Gertsenstein M, Nagy KV, Nagy A. Manipulating the mouse embryo: a laboratory manual. 4th ed. Cold Spring Harbor Laboratory Press: Cold Spring Harbor; 2014.
Blanga-Kanfi S. et al., Rodent phylogeny revised: analysis of six nuclear genes from all major rodent clades. BMC Evol. Biol. 9, 71 (2009).
Carlson et al., Targeting DNA with Fingers and TALENs. Molecular Therapy Nucleic Acids 1(1) (2012).
Chen S, Lee B, Lee AYF, Modzelewski AJ, He L. Highly efficient mouse genome editing by CRISPR ribonucleoprotein electroporation of zygotes. J Biol Chem. 2016;291:14457-67.
Cong et al., Multiplex Genoma Engineering Using CRISPR/Cas Systems. Science 339(6121):819-823 (2013).
Cummins J. M., R. Yanagimachi, Development of ability to penetrate the cumulus oophorus by hamster spermatozoa capacitated in vitro, in relation to the timing of the acrosome reaction. Gamete Res. 15, 187-212 (1986).
Dudkiewicz A. B., Inhibition of fertilization in the rabbit by anti-acrosin antibodies. Gamete Res. 8, 183-197 (1983).
Dumoulin JC, Land JA, Van Montfoort AP, Nelissen EC, Coonen E, Derhaag JG, et al. Effect of in vitro culture of human embryos on birthweight of newborns. Hum Reprod 2010;25:605-612.
Ferrer M. et al., MMP2 and acrosin are major proteinases associated with the inner acrosomal membrane and may cooperate in sperm penetration of the zona pellucida during fertilization. Cell Tissue Res. 349, 881-895 (2012).
Fraser L. R., p-Aminobenzamidine, an acrosin inhibitor, inhibits mouse sperm penetration of the zona pellucida but not the acrosome reaction. J. Reprod. Fertil. 65, 185-194 (1982).
Grealish S, Jönsson ME, Li M, Kirik D, Bjorklund A, Thompson LH. The A9 dopamine neuron component in grafts of ventral mesencephalon is an important determinant for recovery of motor function in a rat model of Parkinson's disease. Brain. 2010;133:482-95.
Green D. P., Mammalian sperm cannot penetrate the zona pellucida solely by force. Exp. Cell Res. 169, 31-38 (1987).
Gurumurthy C. B. et al., Creation of CRISPR-based germline-genome-engineered mice without ex vivo handling of zygotes by i-GONAD. Nature Protoc. 14, 2452-2482 (2019).
Gurumurthy CB, Grati M, Ohtsuka M, Schilit SLP, Quadras RM, Liu XZ. CRISPR: a versatile tool for both forward and reverse genetics research. Hum Genet. 2016;135:971-6.
Gurumurthy CB, Takahashi G, Wada K, Miura H, Sato M, Ohtsuka M. GONAD: a novel CRISPR/Cas9 genome editing method that does not require ex vivo handling of embryos. Curr Protoc Hum Genet 2016;88:15.8.1-15.8.12.
Hancks DC, Kazazian HH, Koning A, Gu W, Castoe T, Batzer M, et al. Roles for retrotransposon insertions in human disease. Mob DNA. 2016;7:9.
Harms DW, Quadros RM, Seruggia D, Ohtsuka M, Takahashi G, Montoliu L, et al. Mouse genome editing using the CRISPR/Cas system. Curr Protoc Hum Genet. 2014;83:15.7.1-15.7.27.
Hashimoto M, Takemoto T. Electroporation enables the efficient mRNA delivery into the mouse zygotes and facilitates CRISPR/Cas9-based genome editing. Sci Rep. 2015;5:11315.
Hashimoto M, Yamashita Y, Takemoto T. Electroporation of Cas9 protein/sgRNA into early pronuclear zygotes generates non-mosaic mutants in the mouse. Dev Biol. 2016;418:1-9.
Haubensak W, Attardo A, Denk W, Huttner WB. Neurons arise in the basal neuroepithelium of the early mammalian telencephalon: a major site of neurogenesis. Proc Natl Acad Sci. 2004;101:3196-201.
Hirose M., A. Ogura, The golden (Syrian) hamster as a model for the study of reproductive biology: Past, present, and future. Reprod. Med. Biol. 18, 34-39 (2019).

(56) References Cited

OTHER PUBLICATIONS

Honda A., J. Siruntawineti, T. Baba, Role of acrosomal matrix proteases in sperm-zona pellucida interactions. Hum. Reprod. Update 8, 405-412 (2002).

Honda A., K. Yamagata, S. Sugiura, K. Watanabe, T. Baba, A mouse serine protease TESP5 is selectively included into lipid rafts of sperm membrane presumably as a glycosylphosphatidylinositol-anchored protein. J. Biol. Chern. 277, 16976-16984 (2002).

Hosseini SH, Sadighi Gilani MA, Meybodi AM, Sabbaghian M. The impact of RABL2B gene (rs144944885) on human male infertility in patients with oligoasthenoteratozoospermia and immotile short tail sperm defects. J Assist Reprod Genet 34, 505-10 (2017).

Hur JK, Kim K, Been KW, Baek G, Ye S, Hur JW, et al. Targeted mutagenesis in mice by electroporation of Cpf1 ribonucleoproteins. Nat Biotechnol 2016;34:807-8.

Inoue N., Y. Satouh, M. Ikawa, M. Okabe, R. Yanagimachi, Acrosome-reacted mouse spermatozoa recovered from the perivitelline space can fertilize other eggs. Proc. Natl Acad. Sci. U. S. A. 108, 20008-20011 (2011).

Isotani A. et al., A delayed sperm penetration of cumulus layers by disruption of acrosin gene in rats. Biol. Reprod. 97, 61-68 (2017).

Jacobi AM, Rettig GR, Turk R, Collingwood MA, Zeiner SA, Quadros RM, et al. Simplified CRISPR tools for efficient genome editing and streamlined protocols for their delivery into mammalian cells and mouse zygotes. Methods. 2017;121-2:16-28.

Jedlicki A., C. Barros, Scanning electron microscope study of in vitro prepenetration gamete interactions. Gamete Res. 11, 121-131 (1985).

Kageyama S, Moriyasu S, Tabata T, Chikuni K. Amplification and sequence analysis of SRY (sex-determining region Y) conserved region of domestic animals using polymerase chain reaction. Anim Sci Technol. 1992;63:1059-65.

Kaneko T, Mashimo T. Simple genome editing of rodent intact embryos by electroporation. PLoS One. 2015;10:e0142755.

Kaneko T, Sakuma T, Yamamoto T, Mashimo T. Simple knockout by electroporation of engineered endonucleases into intact rat embryos. Sci Rep. 2014;4:6382.

Kawano N. et al., Mice lacking two sperm serine proteases, ACR and PRSS21, are subfertile, but the mutant sperm are infertile in vitro. Biol. Reprod. 83, 359-369 (2010).

Khosla S, Dean W, Reik W, Feil R. Culture of preimplantation embryos and its long-term effects on gene expression and phenotype. Hum Reprod Update 2001;7:419-27.

Liu D. Y., H. W. Baker, Inhibition of acrosin activity with a trypsin inhibitor blocks human sperm penetration of the zona pellucida. Biol. Reprod. 48, 340-348 (1993).

Mali et al., RNA-Guided Human Genome Engineering via Cas9. Science 339(6121): 823-826 (2013).

Mao H. T., W. X. Yang, Modes of acrosin functioning during fertilization. Gene 526, 75-79 (2013).

Mashimo T., Gene targeting technologies in rats: zinc finger nucleases, transcription activator-like effector nucleases, and clustered regularly interspaced short palindromic repeats. Dev. Growth. Differ. 56, 46-52 (2014).

Medina-Martinez O, Brownell I, Amaya-Manzanares F, Hu Q, Behringer RR, Jamrich M. Severe defects in proliferation and differentiation of lens cells in Foxe3 null mice. Mol Cell Biol. 2005;25:8854-63.

Michaux J., A. Reyes, F. Catzeflis, Evolutionary history of the most speciose mammals: molecular phylogeny of muroid rodents. Mol. Biol. Evol. 18, 2017-2031 (2001).

Miura H, Gurumurthy CB, Sato T, Sato M, Ohtsuka M. CRISPR/Cas9-based generation of knockdown mice by intronic insertion of artificial microRNA using longer single-stranded DNA. Sci Rep. 2015;5:12799.

Miura H, Quadros RM, Gurumurthy CB, Ohtsuka M. Easi-CRISPR for creating knock-in and conditional knockout mouse models using long ssDNA donors. Nat Protoc. 2018;13:195-215.

Nakanishi T. et al., Real-time observation of acrosomal dispersal from mouse sperm using GFP as a marker protein. FEBS Lett. 449, 277-283 (1999).

Okabe M., Mechanisms of fertilization elucidated by gene-manipulated animals. Asian J. Androl. 17, 646-652 (2015).

Pettitt SJ, Liang Q, Rairdan XY, Moran JL, Prosser HM, Beier DR, et al. Agouti C57BL/6N embryonic stem cells for mouse genetic resources. Nat Methods. 2009;6:493-5.

* cited by examiner

FIG. 1A
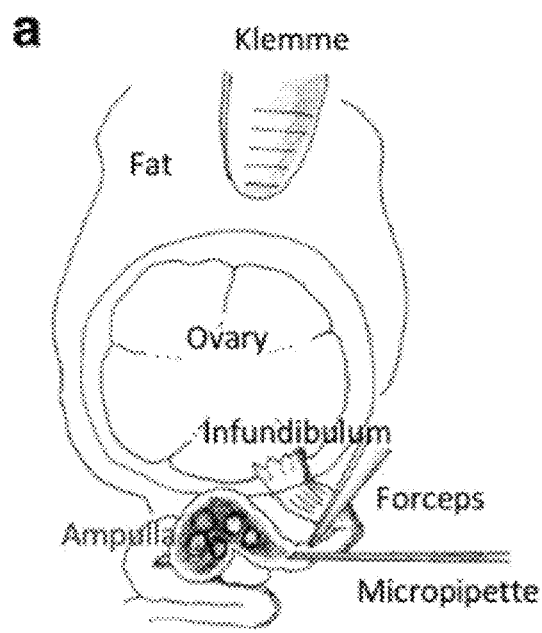
FIG. 1B
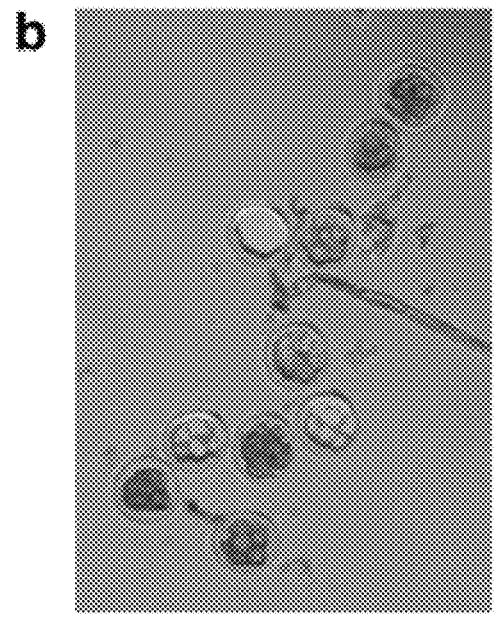
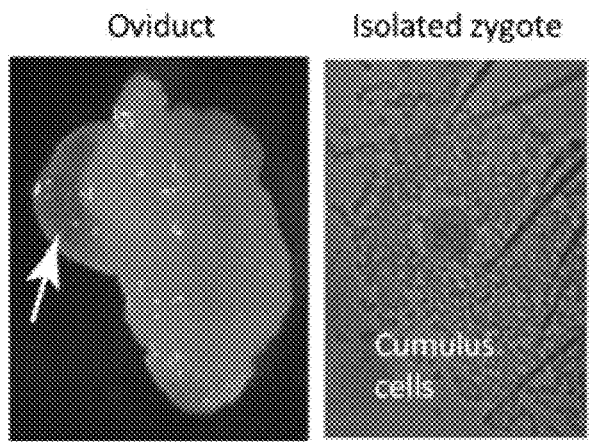
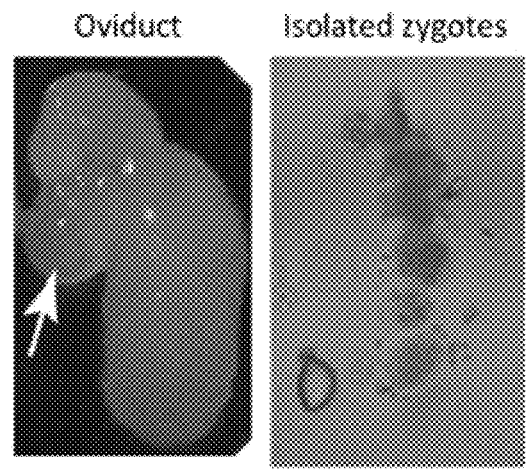
FIG. 1C

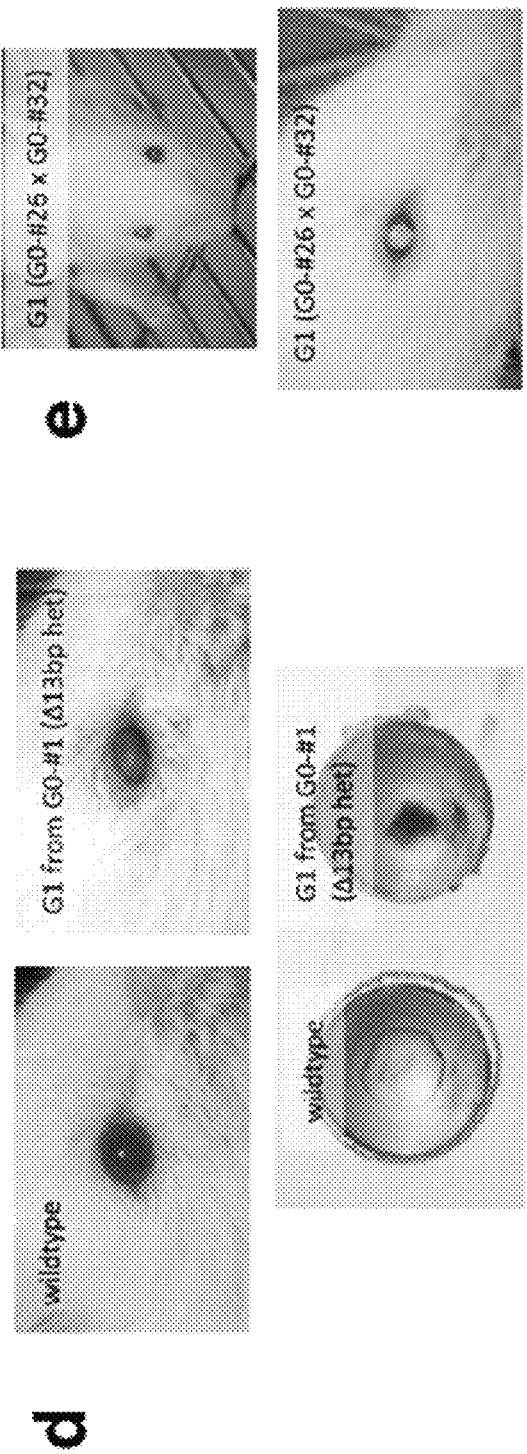

d

(SEQ ID NO: 74)

G0-#1

(SEQ ID NO: 75)

G0-#2

(SEQ ID NO: 76)

G0-#7

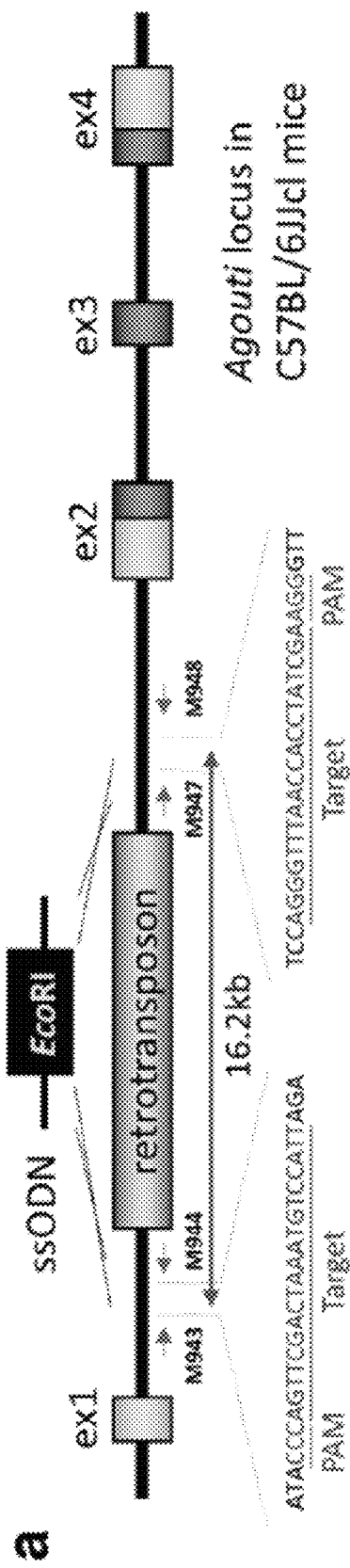
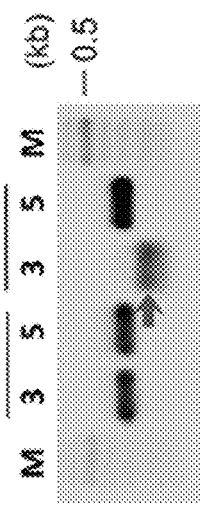
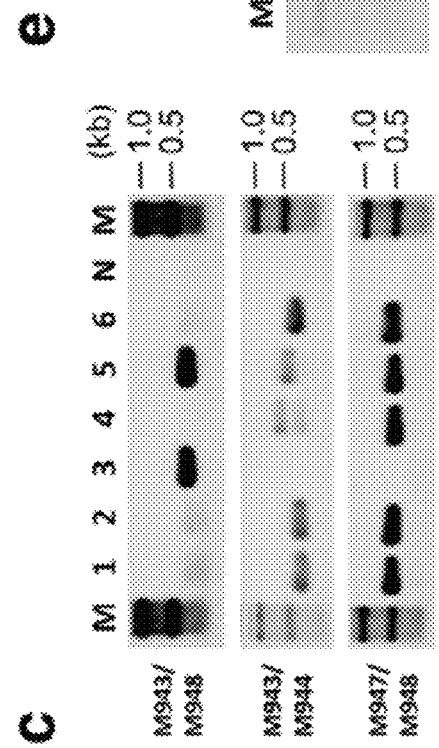
FIG. 4A
FIG. 4B
FIG. 4C
FIG. 4E

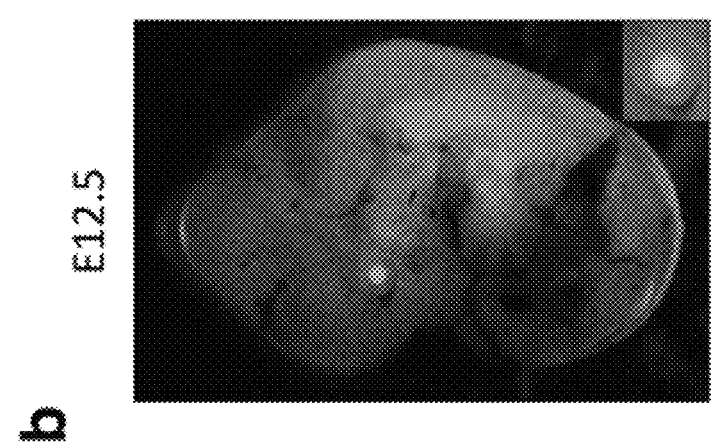
FIG. 5B
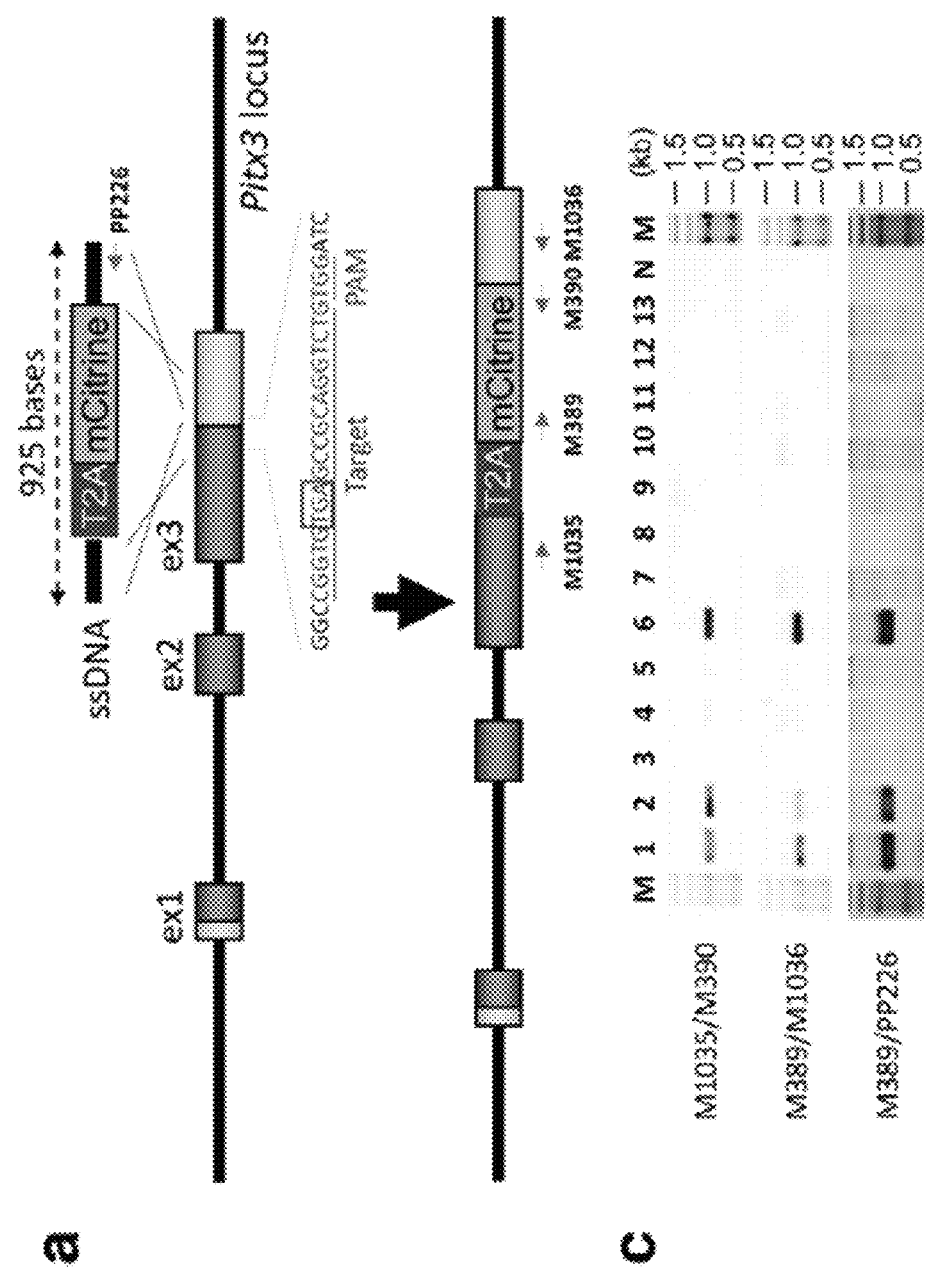
FIG. 5A
FIG. 5C a

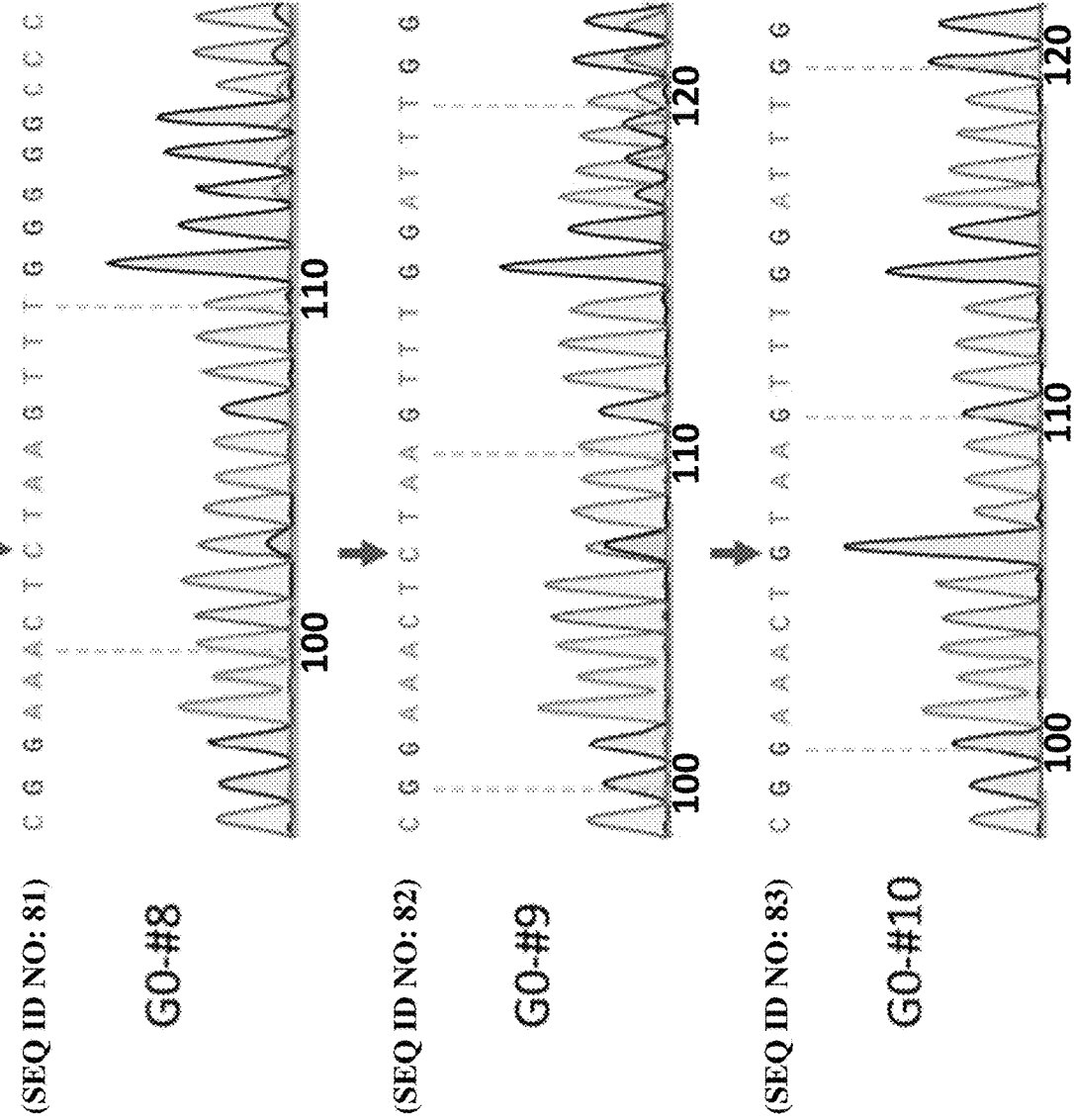

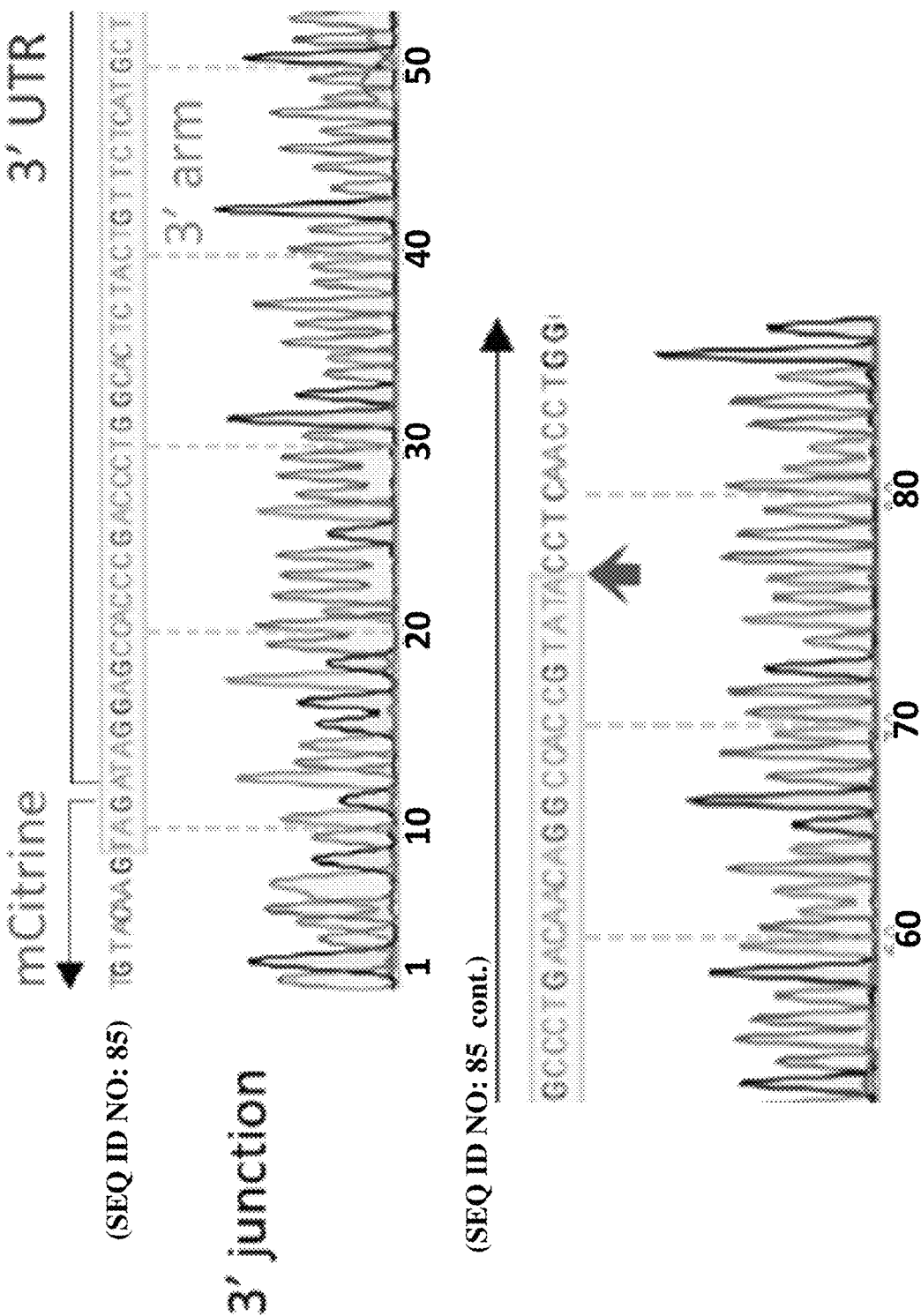

FIG. 9A
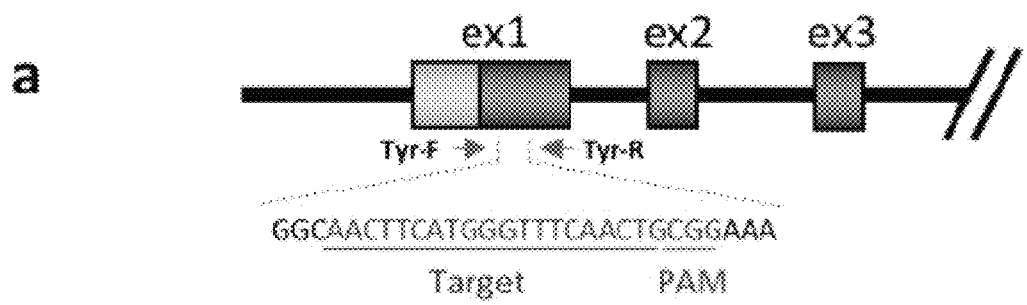
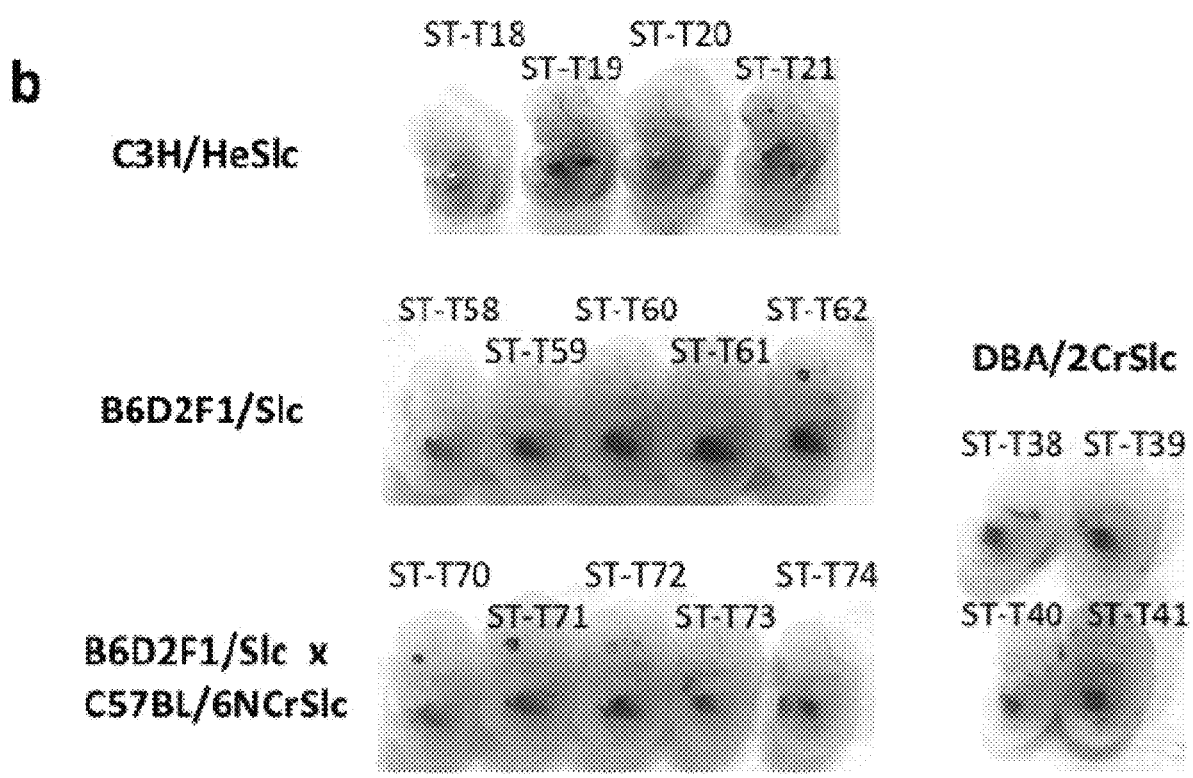
FIG. 9B

C3H/HeSlc

(ST-K9: mutation in both alleles: Δ20bp +3bp)

(SEQ ID NO: 91)

(ST-K19: mutation in one allele: Δ72bp)

(SEQ ID NO: 92)

C57BL/6NCrSlc

(ST-K17: mutation in both alleles: +1bp/ Δ7bp)

(SEQ ID NO: 93)

FIG. 11B

Cdkn1a-knock-in

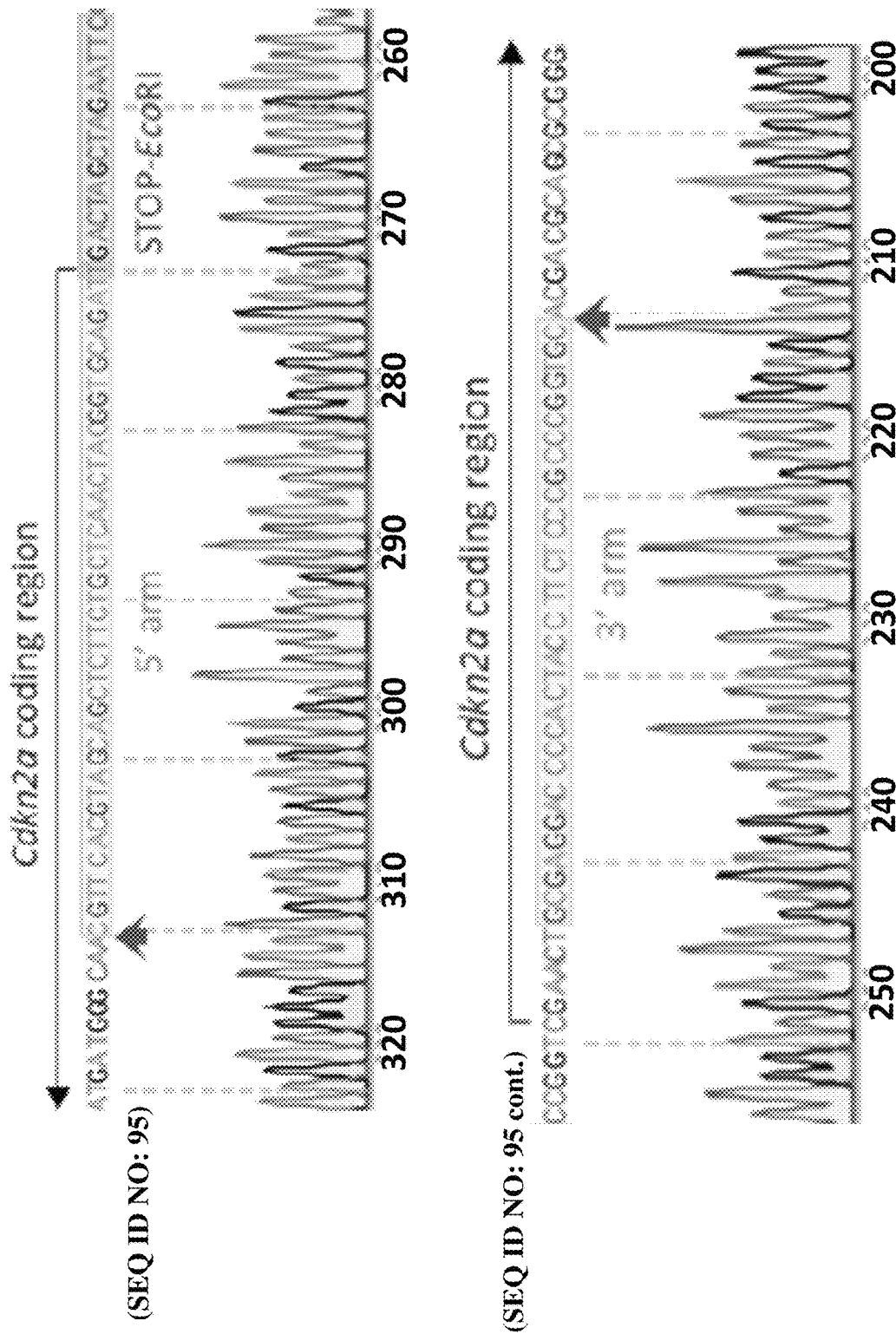

SEQUENCE LISTING

<160> NUMBER OF SEQ ID NOS: 100

<210> SEQ ID NO 1
<211> LENGTH: 29
<212> TYPE: DNA
<213> ORGANISM: Artificial Sequence
<220> FEATURE:
<223> OTHER INFORMATION: Synthetic: Foxe3 Target Sequence

<400> SEQUENCE: 1
cctgagacag ccgggcttcg cgccggggc					29

<210> SEQ ID NO 2
<211> LENGTH: 79
<212> TYPE: DNA
<213> ORGANISM: Artificial Sequence
<220> FEATURE:
<223> OTHER INFORMATION: Synthetic: WT

<400> SEQUENCE: 2
ctcggagccg gggaagccta cctgagacag ccgggcttcg cgccggggct ggagcgctac		60 ctgtgagtcg ctttccgct					79

<210> SEQ ID NO 3
<211> LENGTH: 60
<212> TYPE: DNA
<213> ORGANISM: Artificial Sequence
<220> FEATURE:
<223> OTHER INFORMATION: Synthetic: #1

<400> SEQUENCE: 3
ctcggagccg gggaagccta cctgagacag ccgagcgcta cctgtgagtc gctttccgct		60

<210> SEQ ID NO 4
<211> LENGTH: 39
<212> TYPE: DNA
<213> ORGANISM: Artificial Sequence
<220> FEATURE:
<223> OTHER INFORMATION: Synthetic: #3

<400> SEQUENCE: 4
ctcggaagct ggagcgctac ctgtgagtcg ctttccgct					39

<210> SEQ ID NO 5
<211> LENGTH: 80
<212> TYPE: DNA
<213> ORGANISM: Artificial Sequence
<220> FEATURE:
<223> OTHER INFORMATION: Synthetic: #5

<400> SEQUENCE: 5
ctcggagccg gggaagccta cctgagacag ccgggcttcg cgccggggc tggagcgcta		60 cctgtgagtc gctttccgct					80

<210> SEQ ID NO 6
<211> LENGTH: 44
<212> TYPE: DNA
<213> ORGANISM: Artificial Sequence
<220> FEATURE:
<223> OTHER INFORMATION: Synthetic: #8

<400> SEQUENCE: 6
ctcggagccg gggaagccta cctgagactg agtcgctttc cgct					44

```
<210> SEQ ID NO 7
<211> LENGTH: 76
<212> TYPE: DNA
<213> ORGANISM: Artificial Sequence
<220> FEATURE:
<223> OTHER INFORMATION: Synthetic: #9

<400> SEQUENCE: 7
ctcggagccg gggaagccta cctgagacag ccgggcttcg cggggctgga gcgctacctg    60
tgagtcgctt tccgct                                                   76

<210> SEQ ID NO 8
<211> LENGTH: 76
<212> TYPE: DNA
<213> ORGANISM: Artificial Sequence
<220> FEATURE:
<223> OTHER INFORMATION: Synthetic: #16

<400> SEQUENCE: 8
ctcggagccg gggaagccta cctgagacag ccgggcttcg cggggctgga gcgctacctg    60
tgagtcgctt tccgct                                                   76

<210> SEQ ID NO 9
<211> LENGTH: 33
<212> TYPE: DNA
<213> ORGANISM: Artificial Sequence
<220> FEATURE:
<223> OTHER INFORMATION: Synthetic: #24

<400> SEQUENCE: 9
ctcggagccg gggaagccta cctgctttcc gct                                 33

<210> SEQ ID NO 10
<211> LENGTH: 67
<212> TYPE: DNA
<213> ORGANISM: Artificial Sequence
<220> FEATURE:
<223> OTHER INFORMATION: Synthetic: #26

<400> SEQUENCE: 10
ctcggagccg gggaagccta cctgagacag ccgggcttcg agcgctacct gtgagtcgct    60
ttccgct                                                             67

<210> SEQ ID NO 11
<211> LENGTH: 54
<212> TYPE: DNA
<213> ORGANISM: Artificial Sequence
<220> FEATURE:
<223> OTHER INFORMATION: Synthetic: #32

<400> SEQUENCE: 11
ctcggagccg gggaagccta cctgagacag cctacctgtg agtcgctttc cgct          54

<210> SEQ ID NO 12
<211> LENGTH: 29
<212> TYPE: DNA
<213> ORGANISM: Artificial Sequence
<220> FEATURE:
<223> OTHER INFORMATION: Synthetic: Fig. 3 Target

<400> SEQUENCE: 12
tgcggaaact ctaagtttgg atttggggg                                      29

<210> SEQ ID NO 13
```

```
<211> LENGTH: 29
<212> TYPE: DNA
<213> ORGANISM: Artificial Sequence
<220> FEATURE:
<223> OTHER INFORMATION: Synthetic: Fig. 4 Target 1

<400> SEQUENCE: 13
atacccagtt cgactaaatg tccattaga                                29

Figure 5D:
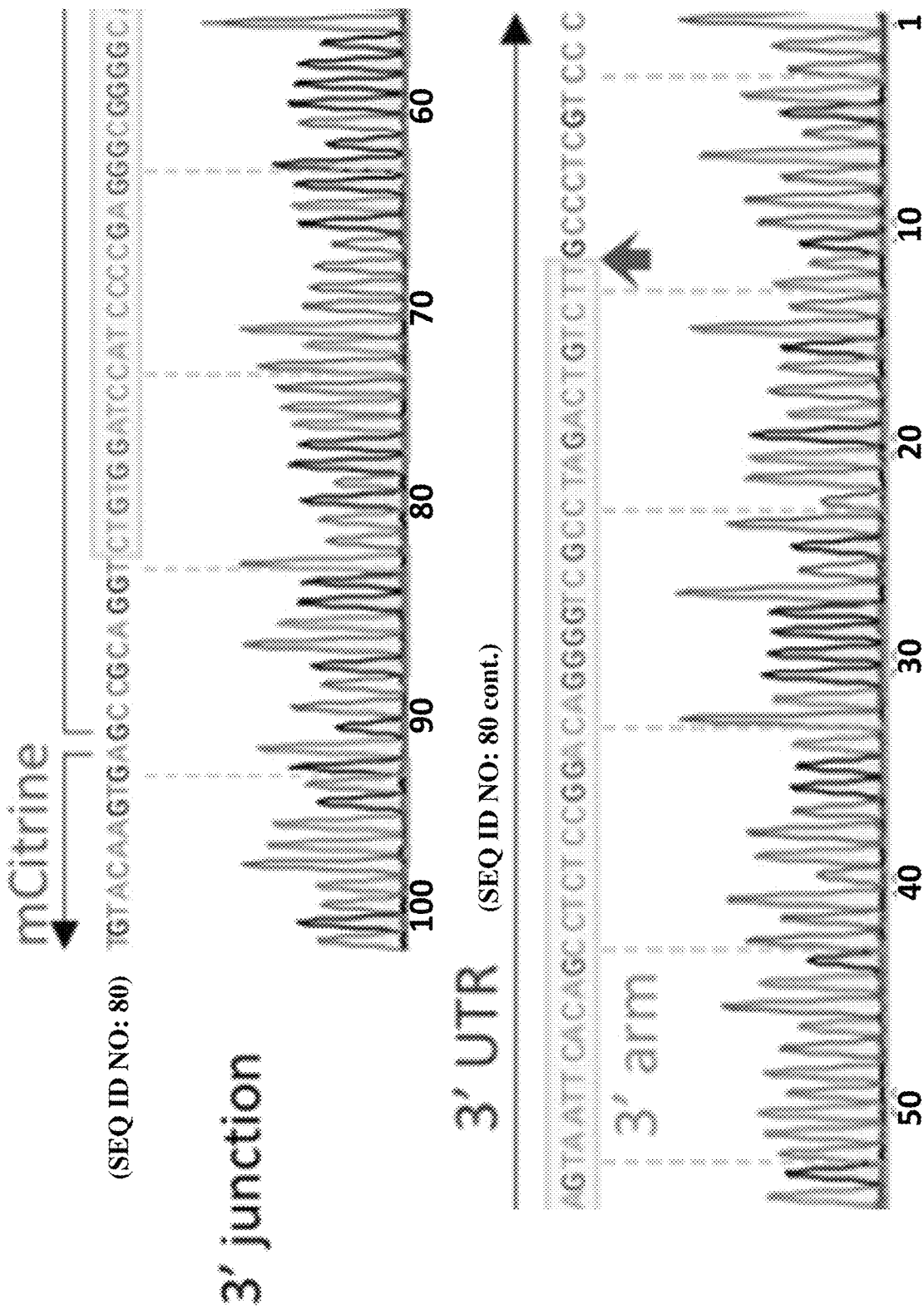

<210> SEQ ID NO 14
<211> LENGTH: 29
<212> TYPE: DNA
<213> ORGANISM: Artificial Sequence
<220> FEATURE:
<223> OTHER INFORMATION: Synthetic: Fig. 5 Target

<400> SEQUENCE: 14
ggccggtgtg agccgcaggt ctgtggatc                                29

<210> SEQ ID NO 15
<211> LENGTH: 29
<212> TYPE: DNA
<213> ORGANISM: Artificial Sequence
<220> FEATURE:
<223> OTHER INFORMATION: Synthetic: Fig. 8 Target

<400> SEQUENCE: 15
tggccgtctc cagctagata ggagccacc                                29

Figure 9C:
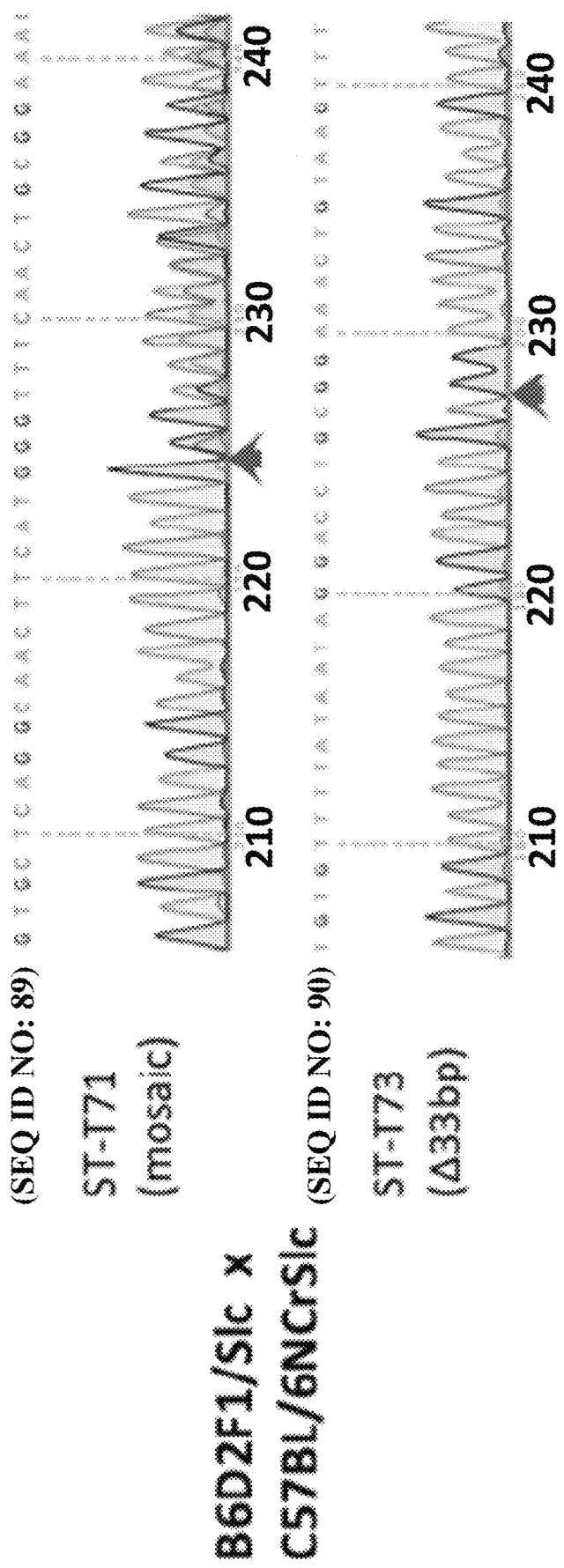

<210> SEQ ID NO 16
<211> LENGTH: 29
<212> TYPE: DNA
<213> ORGANISM: Artificial Sequence
<220> FEATURE:
<223> OTHER INFORMATION: Synthetic: Fig. 9 Target

<400> SEQUENCE: 16
ggcaacttca tgggtttcaa ctgcggaaa                                29

<210> SEQ ID NO 17
<211> LENGTH: 29
<212> TYPE: DNA
<213> ORGANISM: Artificial Sequence
<220> FEATURE:
<223> OTHER INFORMATION: Synthetic: Fig. 10 Target

<400> SEQUENCE: 17
actctgttca cgccgctgct cattggctt                                29

Figure 11A:
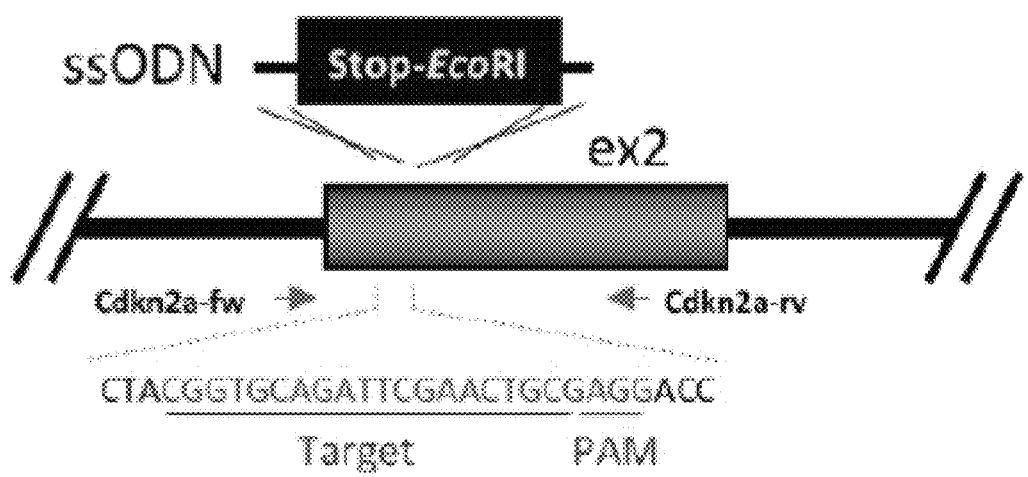

<210> SEQ ID NO 18
<211> LENGTH: 29
<212> TYPE: DNA
<213> ORGANISM: Artificial Sequence
<220> FEATURE:
<223> OTHER INFORMATION: Synthetic: Fig. 11 Target 1

<400> SEQUENCE: 18
ccgtgattgc gatgcgctca tggcgggct                                29

<210> SEQ ID NO 19
<211> LENGTH: 29
<212> TYPE: DNA
<213> ORGANISM: Artificial Sequence
<220> FEATURE:
<223> OTHER INFORMATION: Synthetic: Fig. 11 Target 2

<400> SEQUENCE: 19
```

```
ctacggtgca gattcgaact gcgaggacc                                        29

<210> SEQ ID NO 20
<211> LENGTH: 33
<212> TYPE: DNA
<213> ORGANISM: Artificial Sequence
<220> FEATURE:
<223> OTHER INFORMATION: Synthetic: Fig. 12 Target

<400> SEQUENCE: 20
gggtttcaac tgcggaaact ctaagtttgg att                                   33

<210> SEQ ID NO 21
<211> LENGTH: 20
<212> TYPE: DNA
<213> ORGANISM: Artificial Sequence
<220> FEATURE:
<223> OTHER INFORMATION: Synthetic: Foxe3 Target Seq

<400> SEQUENCE: 21
gagacagccg ggcttcgcgc                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic: Tyr (ICR) Target Seq

<400> SEQUENCE: 22
ggaaactcta agtttggatt                                                  20

<210> SEQ ID NO 23
<211> LENGTH: 20
<212> TYPE: DNA
<213> ORGANISM: Artificial Sequence
<220> FEATURE:
<223> OTHER INFORMATION: Synthetic: Agouti (1) Target Seq

<400> SEQUENCE: 23
aatggacatt tagtcgaact                                                  20

<210> SEQ ID NO 24
<211> LENGTH: 20
<212> TYPE: DNA
<213> ORGANISM: Artificial Sequence
<220> FEATURE:
<223> OTHER INFORMATION: Synthetic: Agouti (2) Target Seq

<400> SEQUENCE: 24
agggtttaac cacctatcga                                                  20

<210> SEQ ID NO 25
<211> LENGTH: 20
<212> TYPE: DNA
<213> ORGANISM: Artificial Sequence
<220> FEATURE:
<223> OTHER INFORMATION: Synthetic: Pitx3 Target Seq

<400> SEQUENCE: 25
cggtgtgagc cgcaggtctg                                                  20

<210> SEQ ID NO 26
<211> LENGTH: 20
<212> TYPE: DNA
```

```
<213> ORGANISM: Artificial Sequence
<220> FEATURE:
<223> OTHER INFORMATION: Synthetic: Tis21 Target Seq

<400> SEQUENCE: 26
ggctcctatc tagctggaga                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic: Tyr (wild) Target Seq

<400> SEQUENCE: 27
aacttcatgg gtttcaactg                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic: Kit Target Seq

<400> SEQUENCE: 28
ctgttcacgc cgctgctcat                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic: p21 (Cdkn1a) Target Seq

<400> SEQUENCE: 29
tgattgcgat gcgctcatgg                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic: p16/p19 (Cdkn2a) Target Seq

<400> SEQUENCE: 30
cggtgcagat tcgaactgcg                                                    20

<210> SEQ ID NO 31
<211> LENGTH: 131
<212> TYPE: DNA
<213> ORGANISM: Artificial Sequence
<220> FEATURE:
<223> OTHER INFORMATION: Synthetic: Tyr-rescue
<220> FEATURE:
<221> NAME/KEY: misc_feature
<222> LOCATION: (45)..(45)
<223> OTHER INFORMATION: n is inosine

<400> SEQUENCE: 31
tgttttataa taggacctgc cagtgctcag gcaacttcat gggtntcaac tgcggaaact        60
gtaagtttgg atttggggge ccaaattgta cagagaagcg agtcttgatt agaagaaaca       120
tttttgattt g                                                            131

<210> SEQ ID NO 32
<211> LENGTH: 124
```

```
<212> TYPE: DNA
<213> ORGANISM: Artificial Sequence
<220> FEATURE:
<223> OTHER INFORMATION: Synthetic: Agouti-rescue
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (24)..(24)
<223> OTHER INFORMATION: n is inosine
<220> FEATURE:
<221> NAME/KEY: misc_feature
<222> LOCATION: (43)..(43)
<223> OTHER INFORMATION: n is inosine
<220> FEATURE:
<221> NAME/KEY: misc_feature
<222> LOCATION: (124)..(124)
<223> OTHER INFORMATION: n is a, c, g, or t

<400> SEQUENCE: 32
tttattgcaa cctgcctntg cctntatatg tgttgaatat ttntagactt gatacccagt      60
gaattcgaag ggtttttccca aacccctcct cagaactcag gagtatcatt aaggtactgc   120 ggtn                                                                  124

<210> SEQ ID NO 33
<211> LENGTH: 20
<212> TYPE: DNA
<213> ORGANISM: Artificial Sequence
<220> FEATURE:
<223> OTHER INFORMATION: Synthetic: M1035

<400> SEQUENCE: 33 tcctcccct atgtataccg                                                   20

<210> SEQ ID NO 34
<211> LENGTH: 19
<212> TYPE: DNA
<213> ORGANISM: Artificial Sequence
<220> FEATURE:
<223> OTHER INFORMATION: Synthetic: M1036

<400> SEQUENCE: 34
tccctgttcc tggccttag                                                   19

<210> SEQ ID NO 35
<211> LENGTH: 20
<212> TYPE: DNA
<213> ORGANISM: Artificial Sequence
<220> FEATURE:
<223> OTHER INFORMATION: Synthetic: M1037

<400> SEQUENCE: 35
cctgtgggtt gatccctatg                                                  20

<210> SEQ ID NO 36
<211> LENGTH: 20
<212> TYPE: DNA
<213> ORGANISM: Artificial Sequence
<220> FEATURE:
<223> OTHER INFORMATION: Synthetic: M1038

<400> SEQUENCE: 36
caaacactgg ctcacagatg                                                  20

<210> SEQ ID NO 37
```

```
<211> LENGTH: 99
<212> TYPE: DNA
<213> ORGANISM: Artificial Sequence
<220> FEATURE:
<223> OTHER INFORMATION: Synthetic: M1051

<400> SEQUENCE: 37
gtaatacgac tcactatagg gcccgggccg ccgccggccg ctaaccttag ccccctgccag     60 tacgccgtgg aacgccggtg ggcagtggag agggcagag                            99

<210> SEQ ID NO 38
<211> LENGTH: 113
<212> TYPE: DNA
<213> ORGANISM: Artificial Sequence
<220> FEATURE:
<223> OTHER INFORMATION: Synthetic: M1052

<400> SEQUENCE: 38
catgaattca agccagtcta ggcgacccct gtccggagag gctgtgaatt actgccccgc     60
cctcggggat ggatccacag acctgcggct cacttgtaca gctcgtccat gcc            113

<210> SEQ ID NO 39
<211> LENGTH: 104
<212> TYPE: DNA
<213> ORGANISM: Artificial Sequence
<220> FEATURE:
<223> OTHER INFORMATION: Synthetic: M1053

<400> SEQUENCE: 39
gtaatacgac tcactatagg gcaagaacca gatgatgctg ggcaggagca gccctcgaa      60 gaactatgtg atggccgtct ccagcggcag tggagagggc agag                      104

<210> SEQ ID NO 40
<211> LENGTH: 98
<212> TYPE: DNA
<213> ORGANISM: Artificial Sequence
<220> FEATURE:
<223> OTHER INFORMATION: Synthetic: M1054

<400> SEQUENCE: 40
catgaattct atacggtggc ctgttgtcag ggcagcatga aacagtaga gtgccagggt      60 cgggtggctc ctatctactt gtacagctcg tccatgcc                             98

<210> SEQ ID NO 41
<211> LENGTH: 62
<212> TYPE: DNA
<213> ORGANISM: Artificial Sequence
<220> FEATURE:
<223> OTHER INFORMATION: Synthetic: M1055

<400> SEQUENCE: 41
taatacgact cactataggg agacagccgg gcttcgcgcg ttttagagct agaaatagca     60
ag                                                                    62

<210> SEQ ID NO 42
<211> LENGTH: 18
<212> TYPE: DNA
<213> ORGANISM: Artificial Sequence
<220> FEATURE:
<223> OTHER INFORMATION: Synthetic: M272

<400> SEQUENCE: 42
caggaaacag ctatgacc                                                   18
```

<210> SEQ ID NO 43
<211> LENGTH: 26
<212> TYPE: DNA
<213> ORGANISM: Artificial Sequence
<220> FEATURE:
<223> OTHER INFORMATION: Synthetic: M389

<400> SEQUENCE: 43
tcgccaccat ggtgagcaag ggcgag                                26

<210> SEQ ID NO 44
<211> LENGTH: 30
<212> TYPE: DNA
<213> ORGANISM: Artificial Sequence
<220> FEATURE:
<223> OTHER INFORMATION: Synthetic: M390

<400> SEQUENCE: 44
ctctagactt tacttgtaca gctcgtccat                            30

<210> SEQ ID NO 45
<211> LENGTH: 21
<212> TYPE: DNA
<213> ORGANISM: Artificial Sequence
<220> FEATURE:
<223> OTHER INFORMATION: Synthetic: M463

<400> SEQUENCE: 45
tccttctgtc cagtgcacca t                                     21

<210> SEQ ID NO 46
<211> LENGTH: 19
<212> TYPE: DNA
<213> ORGANISM: Artificial Sequence
<220> FEATURE:
<223> OTHER INFORMATION: Synthetic: M939

<400> SEQUENCE: 46
aaaaaaagca ccgactcgg                                        19

<210> SEQ ID NO 47
<211> LENGTH: 21
<212> TYPE: DNA
<213> ORGANISM: Artificial Sequence
<220> FEATURE:
<223> OTHER INFORMATION: Synthetic: M943

<400> SEQUENCE: 47
aggatctgtg ttcaacccat t                                     21

<210> SEQ ID NO 48
<211> LENGTH: 21
<212> TYPE: DNA
<213> ORGANISM: Artificial Sequence
<220> FEATURE:
<223> OTHER INFORMATION: Synthetic: M944

<400> SEQUENCE: 48
acaaagaaaa ccaagcgtga c                                     21

<210> SEQ ID NO 49
<211> LENGTH: 21
<212> TYPE: DNA
<213> ORGANISM: Artificial Sequence
<220> FEATURE:

```
<223> OTHER INFORMATION: Synthetic: M947

<400> SEQUENCE: 49
cttgagaaag gccacagttt c                                              21

<210> SEQ ID NO 50
<211> LENGTH: 21
<212> TYPE: DNA
<213> ORGANISM: Artificial Sequence
<220> FEATURE:
<223> OTHER INFORMATION: Synthetic: M948

<400> SEQUENCE: 50
acgaacctct tcatctgctg t                                              21

<210> SEQ ID NO 51
<211> LENGTH: 18
<212> TYPE: DNA
<213> ORGANISM: Artificial Sequence
<220> FEATURE:
<223> OTHER INFORMATION: Synthetic: M992

<400> SEQUENCE: 51
cctggacagc ctgttggg                                                  18

<210> SEQ ID NO 52
<211> LENGTH: 21
<212> TYPE: DNA
<213> ORGANISM: Artificial Sequence
<220> FEATURE:
<223> OTHER INFORMATION: Synthetic: M993

<400> SEQUENCE: 52
ttcagtctgg tggtgagaca g                                              21

<210> SEQ ID NO 53
<211> LENGTH: 20
<212> TYPE: DNA
<213> ORGANISM: Artificial Sequence
<220> FEATURE:
<223> OTHER INFORMATION: Synthetic: M999

<400> SEQUENCE: 53
atgggtgttg acccattgtt                                                20

<210> SEQ ID NO 54
<211> LENGTH: 20
<212> TYPE: DNA
<213> ORGANISM: Artificial Sequence
<220> FEATURE:
<223> OTHER INFORMATION: Synthetic: PP226

<400> SEQUENCE: 54
caagccagtc taggcgaccc                                                20

<210> SEQ ID NO 55
<211> LENGTH: 21
<212> TYPE: DNA
<213> ORGANISM: Artificial Sequence
<220> FEATURE:
<223> OTHER INFORMATION: Synthetic: PP227

<400> SEQUENCE: 55
catgaattct atacggtggc c                                              21
```

<210> SEQ ID NO 56
<211> LENGTH: 22
<212> TYPE: DNA
<213> ORGANISM: Artificial Sequence
<220> FEATURE:
<223> OTHER INFORMATION: Synthetic: Mm HPRT F1S

<400> SEQUENCE: 56
aggtttcgag ccctgatatt cg                                              22

<210> SEQ ID NO 57
<211> LENGTH: 22
<212> TYPE: DNA
<213> ORGANISM: Artificial Sequence
<220> FEATURE:
<223> OTHER INFORMATION: Synthetic: Mm HPRTR1S

<400> SEQUENCE: 57
atgtggcaag gtcaaaaaca gt                                              22

<210> SEQ ID NO 58
<211> LENGTH: 21
<212> TYPE: DNA
<213> ORGANISM: Artificial Sequence
<220> FEATURE:
<223> OTHER INFORMATION: Synthetic: Tyr-F

<400> SEQUENCE: 58
tctctgatgg ccattttcct c                                               21

<210> SEQ ID NO 59
<211> LENGTH: 20
<212> TYPE: DNA
<213> ORGANISM: Artificial Sequence
<220> FEATURE:
<223> OTHER INFORMATION: Synthetic: Tyr-R

<400> SEQUENCE: 59
aacatgggtg ttgacccatt                                                 20

<210> SEQ ID NO 60
<211> LENGTH: 22
<212> TYPE: DNA
<213> ORGANISM: Artificial Sequence
<220> FEATURE:
<223> OTHER INFORMATION: Synthetic: Kit-F
<220> FEATURE:
<221> NAME/KEY: misc_feature
<222> LOCATION: (18)..(18)
<223> OTHER INFORMATION: n is inosine

<400> SEQUENCE: 60
gagggaaatg gtttagtntg gg                                              22

<210> SEQ ID NO 61
<211> LENGTH: 20
<212> TYPE: DNA
<213> ORGANISM: Artificial Sequence
<220> FEATURE:
<223> OTHER INFORMATION: Synthetic: Kit-R

<400> SEQUENCE: 61
gggtttctgg aggagaaagg                                                 20

<210> SEQ ID NO 62
<211> LENGTH: 21
<212> TYPE: DNA

```
<213> ORGANISM: Artificial Sequence
<220> FEATURE:
<223> OTHER INFORMATION: Synthetic: Cdkn1a-lw

<400> SEQUENCE: 62
cctgaagact gtgatggggt a                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetic: Cdkn1a-rv

<400> SEQUENCE: 63
tctccgtgac gaagtcaaag t                                              21

<210> SEQ ID NO 64
<211> LENGTH: 21
<212> TYPE: DNA
<213> ORGANISM: Artificial Sequence
<220> FEATURE:
<223> OTHER INFORMATION: Synthetic: Cdkn2a-lw
<220> FEATURE:
<221> NAME/KEY: misc_feature
<222> LOCATION: (20)..(20)
<223> OTHER INFORMATION: n is inosine

<400> SEQUENCE: 64
gccgtgatcc ctctactttn t                                              21

<210> SEQ ID NO 65
<211> LENGTH: 21
<212> TYPE: DNA
<213> ORGANISM: Artificial Sequence
<220> FEATURE:
<223> OTHER INFORMATION: Synthetic: Cdkn2a-rv

<400> SEQUENCE: 65
tatcgcacga tgtcttgatg t                                              21

<210> SEQ ID NO 66
<211> LENGTH: 31
<212> TYPE: DNA
<213> ORGANISM: Artificial Sequence
<220> FEATURE:
<223> OTHER INFORMATION: Synthetic: Sry-F2

<400> SEQUENCE: 66
aagcgaccca tgaatgcatt catggtgtgg t                                   31

<210> SEQ ID NO 67
<211> LENGTH: 37
<212> TYPE: DNA
<213> ORGANISM: Artificial Sequence
<220> FEATURE:
<223> OTHER INFORMATION: Synthetic: Sry-R2

<400> SEQUENCE: 67
gaggtcgata cttatagttc gggtatttct ctctgtg                             37

<210> SEQ ID NO 68
<211> LENGTH: 29
<212> TYPE: DNA
<213> ORGANISM: Artificial Sequence
<220> FEATURE:
<223> OTHER INFORMATION: Synthetic: Fig. 4 Target 2
```

<400> SEQUENCE: 68
tccagggttt aaccacctat cgaagggtt                                    29

<210> SEQ ID NO 69
<211> LENGTH: 21
<212> TYPE: DNA
<213> ORGANISM: Artificial Sequence
<220> FEATURE:
<223> OTHER INFORMATION: Synthetic: MmHPRT-273-S Primer

<400> SEQUENCE: 69
gtgccctctt ctggcctgcc a                                            21

<210> SEQ ID NO 70
<211> LENGTH: 37
<212> TYPE: DNA
<213> ORGANISM: Artificial Sequence
<220> FEATURE:
<223> OTHER INFORMATION: Synthetic

<400> SEQUENCE: 70
tacctgagac agccgggctt cgccggggct ggagcgc                           37

<210> SEQ ID NO 71
<211> LENGTH: 41
<212> TYPE: DNA
<213> ORGANISM: Artificial Sequence
<220> FEATURE:
<223> OTHER INFORMATION: Synthetic

<400> SEQUENCE: 71
tacctgagac agccgggctt cgcgcgcgct acgggtgact c                      41

<210> SEQ ID NO 72
<211> LENGTH: 39
<212> TYPE: DNA
<213> ORGANISM: Artificial Sequence
<220> FEATURE:
<223> OTHER INFORMATION: Synthetic

<400> SEQUENCE: 72
tacctgagac agccgggctt cgagcgctac ctgtgagtc                         39

<210> SEQ ID NO 73
<211> LENGTH: 39
<212> TYPE: DNA
<213> ORGANISM: Artificial Sequence
<220> FEATURE:
<223> OTHER INFORMATION: Synthetic

<400> SEQUENCE: 73
tacctgagac agcctacctg tgagtcgctt tccgctgcg                         39

<210> SEQ ID NO 74
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: n is a, c, g, or t

<400> SEQUENCE: 74

```
cggaaactct aantttgggg gccc                                           24
```

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75

```
cggaaactgt aagtttggat ttgg                                           24
```

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76

```
cggaaactgt aagtttggag gccg                                           24
```

<210> SEQ ID NO 77
<211> LENGTH: 33
<212> TYPE: DNA
<213> ORGANISM: Artificial Sequence
<220> FEATURE:
<223> OTHER INFORMATION: Synthetic

<400> SEQUENCE: 77

```
acttgatacc cagtgaattc gaagggtttt ccc                                 33
```

<210> SEQ ID NO 78
<211> LENGTH: 29
<212> TYPE: DNA
<213> ORGANISM: Artificial Sequence
<220> FEATURE:
<223> OTHER INFORMATION: Synthetic

<400> SEQUENCE: 78

```
acttgatacc cagttcgaag ggttttccc                                      29
```

<210> SEQ ID NO 79
<211> LENGTH: 143
<212> TYPE: DNA
<213> ORGANISM: Artificial Sequence
<220> FEATURE:
<223> OTHER INFORMATION: Synthetic

<400> SEQUENCE: 79

```
tatcccgccg tgcccgggcc gccgccggcc gctaaccttA gcccctgcca gtacgccgtg    60
gaacggccgg tgggcagtgg agagggcaga ggaagtctgc taacatgcgg tgacgtcgag   120
gagaatcctg gccaatggtg agc                                           143
```

<210> SEQ ID NO 80
<211> LENGTH: 102
<212> TYPE: DNA
<213> ORGANISM: Artificial Sequence
<220> FEATURE:
<223> OTHER INFORMATION: Synthetic

<400> SEQUENCE: 80

```
tgtacaagtg agccgcaggt ctgtggatcc atccccgagg gcggggcagt aattcacagc    60
ctctccggac aggggtcgcc tagactgtct tgccctcgtc cc                      102
```

<210> SEQ ID NO 81
<211> LENGTH: 24
<212> TYPE: DNA
<213> ORGANISM: Artificial Sequence
<220> FEATURE:
<223> OTHER INFORMATION: Synthetic

<400> SEQUENCE: 81
cggaaactct aagtttgggg gccc                                          24

<210> SEQ ID NO 82
<211> LENGTH: 24
<212> TYPE: DNA
<213> ORGANISM: Artificial Sequence
<220> FEATURE:
<223> OTHER INFORMATION: Synthetic

<400> SEQUENCE: 82
cggaaactct aagtttggat ttgg                                          24

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
cggaaactgt aagtttggat ttgg                                          24

<210> SEQ ID NO 84
<211> LENGTH: 148
<212> TYPE: DNA
<213> ORGANISM: Artificial Sequence
<220> FEATURE:
<223> OTHER INFORMATION: Synthetic

<400> SEQUENCE: 84
gctcctcacc tgcaagaacc agatgatgct gggcaggagc agcccctcga agaactatgt    60
gatggccgtc tccagcggca gtggagaggg cagaggaagt ctgctaacat gcggtgacgt   120
cgaggagaat cctggcccaa tggtgagc                                     148

<210> SEQ ID NO 85
<211> LENGTH: 87
<212> TYPE: DNA
<213> ORGANISM: Artificial Sequence
<220> FEATURE:
<223> OTHER INFORMATION: Synthetic

<400> SEQUENCE: 85
tgtacaagta gataggagcc acccgaccct ggcactctac tgttctcatg ctgccctgac    60
aacaggccac cgtataccte aacctgg                                       87

<210> SEQ ID NO 86
<211> LENGTH: 35
<212> TYPE: DNA
<213> ORGANISM: Artificial Sequence
<220> FEATURE:
<223> OTHER INFORMATION: Synthetic

<400> SEQUENCE: 86
aacttcatgg gtttcaaact gcggaaactg taagt                              35

<210> SEQ ID NO 87
<211> LENGTH: 38
<212> TYPE: DNA
<213> ORGANISM: Artificial Sequence
<220> FEATURE:
<223> OTHER INFORMATION: Synthetic

<400> SEQUENCE: 87
tcaggcaact tcatgggttt cttagaggaa actgtaag        38

<210> SEQ ID NO 88
<211> LENGTH: 34
<212> TYPE: DNA
<213> ORGANISM: Artificial Sequence
<220> FEATURE:
<223> OTHER INFORMATION: Synthetic

<400> SEQUENCE: 88
tcaggcaact tcatgaaact gtaagtttgg attt        34

<210> SEQ ID NO 89
<211> LENGTH: 36
<212> TYPE: DNA
<213> ORGANISM: Artificial Sequence
<220> FEATURE:
<223> OTHER INFORMATION: Synthetic

<400> SEQUENCE: 89
gtgctcaggc aacttcatgg gtttcaactg cggaaa        36

<210> SEQ ID NO 90
<211> LENGTH: 37
<212> TYPE: DNA
<213> ORGANISM: Artificial Sequence
<220> FEATURE:
<223> OTHER INFORMATION: Synthetic

<400> SEQUENCE: 90
tgtgttttat aataggacct gcggaaactg taagttt        37

<210> SEQ ID NO 91
<211> LENGTH: 40
<212> TYPE: DNA
<213> ORGANISM: Artificial Sequence
<220> FEATURE:
<223> OTHER INFORMATION: Synthetic

<400> SEQUENCE: 91
caggcccaca ctctgttcca gtgtggttgc agctggcgcg        40

<210> SEQ ID NO 92
<211> LENGTH: 36
<212> TYPE: DNA
<213> ORGANISM: Artificial Sequence
<220> FEATURE:
<223> OTHER INFORMATION: Synthetic

<400> SEQUENCE: 92
cccacactct gttcacgccg caggtcagcg ttgaat        36

<210> SEQ ID NO 93
<211> LENGTH: 35
<212> TYPE: DNA
<213> ORGANISM: Artificial Sequence
<220> FEATURE:
<223> OTHER INFORMATION: Synthetic

```
<400> SEQUENCE: 93
actctgttca cgccgctgct tctgtggctt cggggg                              35

<210> SEQ ID NO 94
<211> LENGTH: 117
<212> TYPE: DNA
<213> ORGANISM: Artificial Sequence
<220> FEATURE:
<223> OTHER INFORMATION: Synthetic

<400> SEQUENCE: 94
cgttgtctct tcggtcccgt ggacagtgag cagttgcgcc gtgattgcga ttgactagct    60
agaattcccg ggcgctcatg gcgggctgtc tccaggaggc ccgagaacgg tggaact     117

<210> SEQ ID NO 95
<211> LENGTH: 125
<212> TYPE: DNA
<213> ORGANISM: Artificial Sequence
<220> FEATURE:
<223> OTHER INFORMATION: Synthetic

<400> SEQUENCE: 95
atgatgggca acgttcagta gcagctcttc tgctcaacta cggtgcagat tgactagcta    60
gaattcccgg tcgaactgcg aggaccccac taccttctcc cgcccggtgc acgacgcagc   120
gcggg                                                              125

<210> SEQ ID NO 96
<211> LENGTH: 42
<212> TYPE: DNA
<213> ORGANISM: Artificial Sequence
<220> FEATURE:
<223> OTHER INFORMATION: Synthetic

<400> SEQUENCE: 96
ttcatgggtt tcaactgcgg aaactctaag tttggatttg gg                       42

<210> SEQ ID NO 97
<211> LENGTH: 42
<212> TYPE: DNA
<213> ORGANISM: Artificial Sequence
<220> FEATURE:
<223> OTHER INFORMATION: Synthetic

<400> SEQUENCE: 97
ttcatgggtt tcaactgcgg aaactgtaag tttggatttg gg                       42

<210> SEQ ID NO 98
<211> LENGTH: 42
<212> TYPE: DNA
<213> ORGANISM: Artificial Sequence
<220> FEATURE:
<223> OTHER INFORMATION: Synthetic

<400> SEQUENCE: 98
ttcatgggtt tcaactgcgg aaactgttTt tttggatttg gg                       42

<210> SEQ ID NO 99
<211> LENGTH: 22
<212> TYPE: DNA
<213> ORGANISM: Artificial Sequence
<220> FEATURE:
<223> OTHER INFORMATION: Synthetic- WT
```

```
<400> SEQUENCE: 99
ttctggacag ggggacagtg gt                                            22

<210> SEQ ID NO 100
<211> LENGTH: 26
<212> TYPE: DNA
<213> ORGANISM: Artificial Sequence
<220> FEATURE:
<223> OTHER INFORMATION: Synthetic- F0 ID #8 F

<400> SEQUENCE: 100
tggagtctac acagccacct gggccc                                        26
```

METHODS AND COMPOSITIONS FOR IN SITU GERMLINE GENOME ENGINEERING

CROSS-REFERENCE TO RELATED PATENT APPLICATIONS

The present application is a continuation-in-part under 35 U.S.C. § 120 to international application PCT/US2018/047748, filed on Aug. 23, 2018, which international application claims the benefit of priority under 35 U.S.C. § 119(e) to U.S. Provisional Patent Application No. 62/549,644, filed on Aug. 24, 2017, the contents of which applications are incorporated herein by reference in their entireties.

SEQUENCE LISTING

This application is being filed electronically via EFS-Web and includes an electronically submitted Sequence Listing in .txt format. The .txt file contains a sequence listing entitled "170799.00011 2023-02-15_ST25.txt" created on Feb. 15, 2023 and is 21,770 bytes in size. The Sequence Listing contained in this .txt file is part of the specification and is hereby incorporated by reference herein in its entirety.

BACKGROUND

Recent advances in genome editing using clustered regularly interspaced short palindromic repeats (CRISPR)/CRISPR associated protein (Cas) enable production of genetically-modified animals easily and rapidly [1, 2, 3]. CRISPR animal genome engineering, methods include three broad steps: mating of females and isolation of zygotes, microinjection of genome editing components into the zygotes, and transfer of microinjected zygotes into the oviducts of females [1, 2]. These steps require (1) a very high level of technical expertise by the technicians who perform these procedures and (2) expensive apparatus, including micromanipulators. Because of the complex nature of the protocol, animal genome engineering experiments are difficult to perform in individual laboratories, and are typically performed in centralized cores, where highly trained personnel offer genome engineering services on a day-to-day basis. The development of methods that circumvent such complex steps enables animal genome engineering technologies to be performed by many more laboratories, not just cores. Some groups have investigated the use of in vitro electroporation of zygotes as an alternative to microinjection, and they successfully produced genome-edited fetuses and pups using this approach [4, 5, 6, 7, 8, 9]. Electroporation of zygotes overcomes the microinjection step, but this strategy still requires the other two difficult steps: isolation of zygotes for ex vivo handling and their transfer back into pseudopregnant females. Accordingly, there remains a need in the art for new genome engineering methods that could simplify the production of genetically-modified animals.

SUMMARY

In one aspect of the present invention, methods for germline genome engineering in a subject having a reproductive organ containing a fertilized zygote are provided. The methods may include isolating or obtaining the reproductive organ from the subject after a time period following insemination of the subject; introducing a reagent composition into the reproductive organ, the reagent composition comprising a nuclease system and/or an exogeneous polynucleotide, and electroporating the reproductive organ.

In another aspect, the present invention relates to reproductive organ compositions. The compositions may include a reproductive organ containing a fertilized zygote from a subject after a time period following insemination of the subject, the reproductive organ comprising a reagent composition, and the reagent composition comprising a nuclease system and/or an exogenous polynucleotide.

In a still further aspect, the present invention relates to uses of an electroporator. The uses may include the use of an electroporator to introduce a reagent composition comprising a nuclease system and/or an exogenous polynucleotide into a reproductive organ containing a fertilized zygote from a subject after a time period following insemination of the subject.

BRIEF DESCRIPTION OF DRAWINGS

FIGS. 1A-1C show an evaluation of earlier time points for performing GONAD. FIG. 1A Diagrammatic illustration showing the anatomical structures of ovary and oviduct and the surgical equipment used for GONAD procedure. A small amount of solution is injected by direct insertion of a glass micropipette through oviduct wall located at the region between the ampulla and infundibulum. Immediately after injection, in vivo electroporation is performed on the entire oviduct. FIG. 1B Detection of eGFP fluorescence in 8-cell to morula embryos after delivery of eGFP mRNA via GONAD procedure. The eGFP fluorescence in preimplantation embryos, isolated 2 days post GONAD procedure performed on naturally mated Jcl:MCH(ICR) female at 0.7 day of pregnancy. FIG. 1C Oviducts and zygotes dissected on days 0.4 (left panel) and 0.7 (right panel). Note that the oviduct dissected on day 0.4 exhibits swelling of the ampulla (arrow). The zygotes isolated from the day 0.4 ampulla are usually surrounded by thick layer of cumulus cells. These cells may hamper efficient uptake of exogenous nucleic acids/proteins injected intra-oviductally and subsequently electroporated. The oviduct dissected on day 0.7 exhibits shrinkage of the ampulla (arrow), and zygotes isolated from the day 0.7 ampulla have fewer cumulus cells, which will less likely hamper the uptake of exogenous nucleic acids/proteins upon electroporation FIGS. 2A-2E show creating gene-inactivated animal models using the GONAD method. FIG. 2A Schematic of the targeting strategy to inactivate Foxe3 gene using Foxe3 target sequence (SEQ ID NO: 1) and the primer set used for genotyping. FIG. 2B Direct sequencing results of polymerase chain reaction (PCR) products amplified from the founder (G0) mice with the primer set shown in FIG. 2A. The red arrows below the electropherogram show the region with indel mutations. FIG. 2C Mutated Foxe3 alleles in the G0 mice (SEQ ID NOS: 2-11). The changes in the nucleotide sequence are shown in red, and the type of changes (insertions+Xnt, or deletions Δ) is indicated on the right side of the sequences. FIG. 2D and FIG. 2E Cataract phenotypes in the G1 mice.

FIG. 3A Schematic to show rescue of Tyr gene mutation. The target region containing the guide sequence and the genotyping primer binding sites are shown (SEQ ID NO: 12). FIG. 3B Representative E14.5 litter showing Tyr rescued G0 fetuses. The pigmented eyes of the fetuses are indicated by yellow arrows. FIG. 3C Representative Tyr rescued G0 mouse litters obtained from #5 female mouse in Table 3. G0 mice indicated in # numbers (shown in yellow) were used for germline transmission analysis (see details in FIGS. 7A-7B). FIG. 3D Direct sequencing results of PCR products amplified from the G0 fetuses in FIG. 3B. The positions for mutated/corrected nucleotides are indicated by red arrows.

FIGS. 4A-4E show creating large deletion using the i-GONAD method. FIG. 4A Schematic diagram showing deletion of 16.2-kb sequence consisting of retrotransposon in the C57BL/6JJcl mouse genome, to restore agouti phenotype. The target sequences and genotyping primers are shown (SEQ ID NOS: 13 and 68). ssODN containing EcoRI site at the middle of the sequence was used. FIG. 4B Representative mice showing rescued agouti phenotype (indicated by yellow arrows). These mice were recovered through caesarean section and nursed by Jcl:MCH(ICR) foster mother with her own pups. FIG. 4C Genotyping analyses. Expected fragment sizes: M943/M948=290 or 295 bp (ssODN knock-in), M943/M94=337 bp, M947/M948=477 bp. FIG. 4D Direct sequencing results of PCR products amplified from the G0 mice. The position of junctional sequences is indicated by yellow rectangles. FIG. 4E EcoRI digestion of PCR products amplified from G0 mice (G0-#3 and -#5) with the M943/M948 primer set. Red arrow indicates digested fragment.

FIGS. 5A-5D show generation of reporter knock-in mice using the i-GONAD method. FIG. 5A Schematic diagram showing insertion of T2A-mCitrine cassette into Pitx3 locus. The target sequence and the genotyping primer sets are shown (SEQ ID NO: 14). A 925-base-long ssDNA synthesized by ivTRT method was used as the donor DNA. FIG. 5B mCitrine fluorescence in fetus collected at E12.5. The eye of the fetus is enlarged as an inset. FIG. 5C Example of genotyping analysis of knock-in G0 fetuses. Expected fragment sizes: M1035/M390=948 bp, M389/M1036=956 bp, M389/PP226=809 bp. N negative control, M size marker. FIG. 5D Representative sequencing chromatogram showing 5' and 3' junctional regions of the inserted cassette. The junctional sequences showing insertion derived from G0-#1 in c are shown. Red arrows indicate junctions between the arms and the genomic sequences.

FIGS. 7A-7B show Germline transmission of Tyr-gene-corrected allele. The G0 mice (G0-#8, -#9, and -#10 obtained from female #5 mouse in Table 3; see also FIG. 3C) were mated with Jcl:MCH(ICR) mice and germline transmission of repaired allele was checked by coat color observation. FIG. 7A The G0-#9 and -#10 mice (shown in yellow arrows) were mated with Jcl:MCH(ICR) mice (shown in black arrows) to obtain G1 offspring. FIG. 7B Direct sequencing results of PCR products amplified from each of the G0 mouse. Red arrows indicate the position of the mutated/corrected nucleotides.

FIG. 8A Schematic diagram illustrating the insertion of "T2A-mCitrine" cassette into the Tis21 locus. The target sequence and the primer sets used for genotyping are shown (SEQ ID NO: 15). A 922 bases-long ssDNA synthesized by ivTRT method was used as the donor DNA. FIG. 8B mCitrine fluorescence in the G0-#2 fetus collected at Day 14.5 (right) whereas no fluorescence was detected in the fetus G0-#1 (left). FIG. 8C Genotyping analysis for the knock-in allele in G0 fetuses. Expected fragment sizes: M1037/M390=964-bp, M389/M1038=1005-bp, M389/PP227=802-bp. N: negative control, M: size marker. The PCR band shown with a red arrow indicates the correct insertion of the cassette and the bands shown in blue arrows indicate partial insertion. FIG. 8D sequencing chromatogram showing 5' and 3' junctional regions of the inserted cassette. The junctional sequences showing insertion in the G0-#2 fetus in FIG. 8B is shown. Red arrows indicate junctions between the arms and the genomic sequences.

FIG. 9A-9C shows generation of indel mutation in the Tyr locus of various mouse strains using I GONAD. FIG. 9A Schematic of the Tyr gene targeting strategy and the primer set used for genotyping (SEQ ID NO: 16). FIG. 9B Representative fetuses showing Tyr knockout phenotype (loss of eye pigmentation). FIG. 9C Direct sequencing results of PCR products amplified from each of the G0 fetuses. Red arrows indicate the position of the mutated nucleotides.

FIG. 10A Schematic of the Kit gene targeting strategy and the primer set used for genotyping (SEQ ID NO: 17). FIG. 10B Representative fetuses showing Kit knockout phenotype (body color phenotype). FIG. 10C Direct sequencing results of PCR products amplified from each of the G0 fetuses. Red arrows indicate the position of the mutated nucleotides.

Figure 11B:
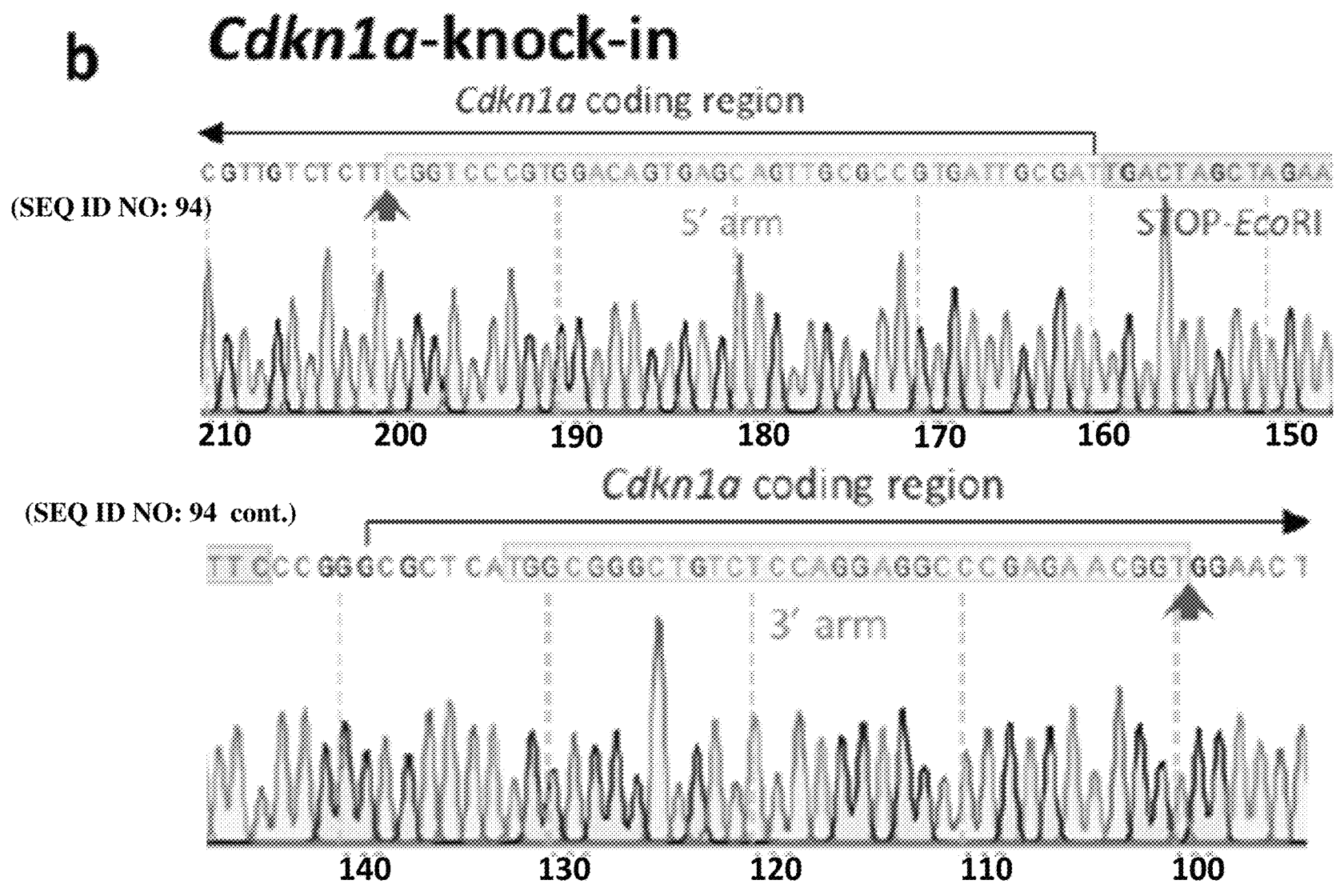

FIGS. 11A-11B show knock-in of ssODN into Cdkn1a and Cdkn2a loci in the C57BL/6NCrl mouse strain using i-GONAD. FIG. 11A Schematic of the targeting strategy to inactivate Cdkn1a or Cdkn2a gene and the primer sets used for genotyping (SEQ ID NOS: 18 and 19). FIG. 11B Sequencing results of cloned PCR products amplified from each of the G0 fetuses. Red arrows indicate junctions between the arms and the genomic sequences.

FIG. 12A Schematic to show rescue of Tyr gene mutation. The target region containing the guide sequence for AsCpf1 and the genotyping primer binding sites are shown (SEQ ID NO: 20). FIG. 12B Representative E14.5 litter showing Tyr rescued G0 fetuses. The pigmented eyes of the fetuses are indicated by yellow arrows. FIG. 12C Direct sequencing results of PCR products amplified from the G0 fetuses (in FIG. 12B). The position for mutated/corrected nucleotides are indicated by red arrows.

DETAILED DESCRIPTION

Figure 2A:
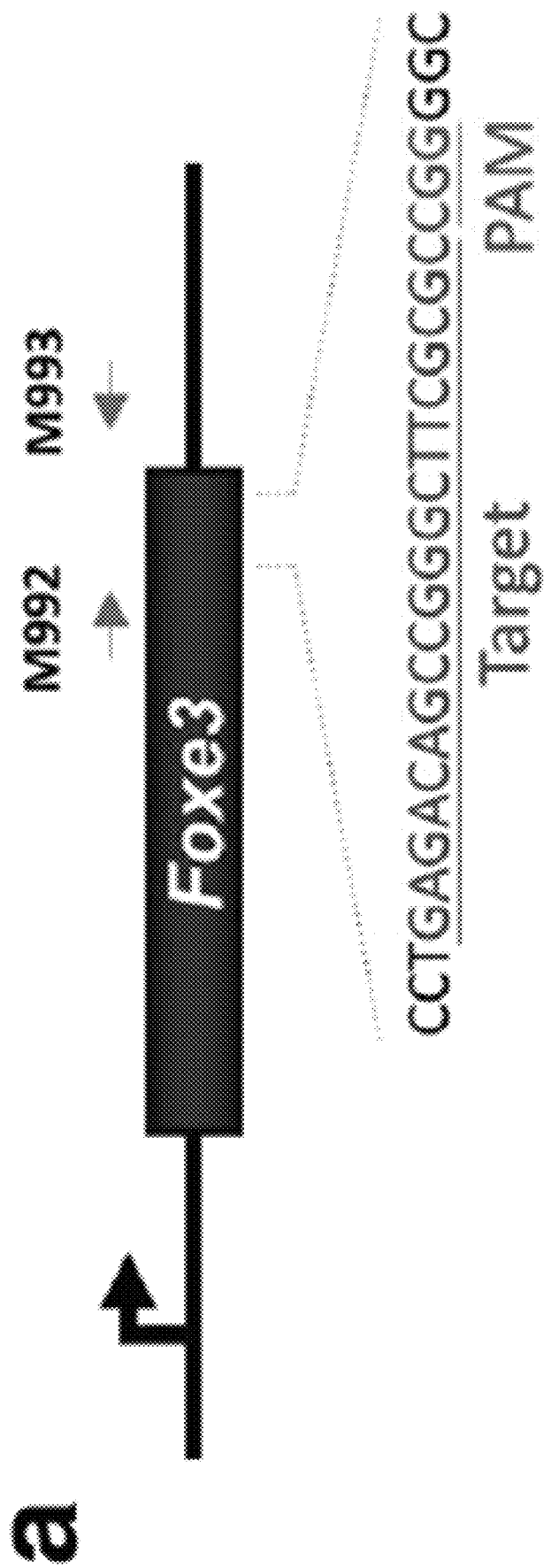

Here, in the non-limiting Examples, the present inventors disclose a robust method called improved-Genome editing via Oviductal Nucleic Acids Delivery (i-GONAD). The method generates mouse models containing single-base changes, kilobase-sized deletions, and knock-ins. The efficiency of i-GONAD is comparable to that of traditional microinjection methods, which rely on ex vivo handling of zygotes and require recipient animals for embryo transfer. In contrast, i-GONAD avoids these technically difficult steps, and it can be performed at any laboratory with simple equipment and technical expertise. Further, i-GONAD-treated females retain reproductive function, suggesting future use of the method for germline gene therapy.

Methods

In one aspect of the present invention, methods for germline genome engineering in a subject having a reproductive organ containing a fertilized zygote are provided. The methods may include isolating or obtaining the reproductive organ from the subject after a time period following insemination of the subject; introducing a reagent composition into the reproductive organ, the reagent composition comprising a nuclease system and/or an exogenous polynucleotide, and electroporating the reproductive organ.

As used herein, the term "subject" or "subject having a reproductive organ containing a fertilized zygote" are used interchangeably herein and refer to both human and nonhuman animals having at least one reproductive organ containing a fertilized zygote. The term "nonhuman animals" of the disclosure may include, without limitation, vertebrates, e.g., mammals and non-mammals, such as nonhuman primates, sheep, goat, dog, cat, horse, cow, pig, mice, rats, chickens, amphibians, reptiles, and the like, or invertebrates, e.g., insects. In some embodiments, the subject is a human patient. The subject may be a human patient in need of a genetically-modified zygote or genetically-modified cells in an embryo harbored by the subject. In some embodiments, the subject is a rodent (e.g., a mouse, rat, or hamster).

The "reproductive organ" or "reproductive organ containing a fertilized zygote" may be any organ or tissue in a reproductive tract of a subject that may include a fertilized zygote including, without limitation, an oviduct, uterus, or ovary.

In some embodiments, the reproductive organ is an oviduct. An "oviduct" is the tube through which an ovum or egg passes from an ovary. In some subjects, an oviduct may also be referred to as a "uterine tube," (i.e., female mammals) "Fallopian tube," (i.e., female mammals) or "ciliated tube" (i.e., amphibians).

To isolate or obtain the reproductive organ from the subject, appropriate surgical procedures may be used to expose the reproductive organ of the subject. The reproductive organ may be temporarily removed from the body of the subject or remain within the body of the subject. For example, in the non-limiting Examples, the present inventors performed surgical procedures on anesthetized female mice. The ovary/oviduct/uterus from the mice were exposed after making an incision at the dorsal skin.

As used herein, the terms "inseminate," "inseminated," "insemination," etc. refers to the introduction of sperm into a subject for the purposes of impregnating the subject (i.e., fertilizing an egg in the subject). The subject may be inseminated by either natural or artificial means. Natural insemination may include sexual intercourse. In some embodiments, the subject is inseminated by mating the subject with another subject. Artificial insemination may include non-intercourse methods of introducing sperm into the subject such as, without limitation, intracervical insemination or intrauterine insemination.

The reproductive organ of the subject may be isolated or obtained following a "time period" after insemination of the subject. The present inventors previously performed their GONAD method with reproductive organs ~1.5 to 1.7 days after insemination. At this stage of pregnancy, embryos are at the 2-cell stage and the inventors discovered that delivery of genome editing reagents at this stage results in a high frequency of mosaic embryos or fetuses [10]. Here, to investigate the ideal time to deliver gene editing components that would correspond to the 1-cell stage and thus reduce genetic mosaicism, the present inventors performed the methods disclosed herein at two separate time points, day 0.4 and day 0.7. The present inventors discovered that although the methods disclosed herein performed 0.7 days after insemination were effective for genome editing and reduced mosaicism, they also observed that 0.4 days after insemination did not elicit effective genome editing.

Based in part on this discovery, the time period following insemination of the subject may be between 0.5 days (12 hours) and 1.4 days (33.6 hours), 0.6 days (14.4 hours) and 1.3 days (31.2 hours), 0.7 days (16.8 hours) and 1.2 days (28.8 hours), 0.8 days (19.2 hours) and 1.1 days (26.4 hours), or any range therein. In some embodiments, the time period following insemination of the subject may be between 0.6 days (14.4 hours) and 0.8 days (19.2 hours).

In some embodiments, the time period following insemination of the subject may be about 0.5 days (12 hours), about 0.6 days (14.4 hours), about 0.7 days (16.8 hours), about 0.8 days (19.2 hours), about 0.9 days (21.6 hours), about 1.0 days (24 hours), about 1.1 days (26.4 hours), about 1.2 days (28.8 hours), about 1.3 days (31.2 hours), or about 1.4 days (33.6 hours).

The time period following insemination may be measured as done by the present inventors in the non-limiting Examples. Briefly, female mice subjects were mated with males. Matings were set up at 16:00-17:00, and copulation plugs were confirmed by visual inspection the next morning (9:00-10:00). They designated day 0 of gestation at 0:00 (midnight) according to *Manipulating the Mouse Embryo: A Laboratory Manual* [30], and the females with plugs were designated as day 0.4 of gestation at 10:00 and day 0.7 of gestation at 16:00. Corresponding procedures may be adapted to subjects beyond mice by those of skill in the art.

The reagent composition may be "introduced" into the reproductive organ using methods including, without limitation, injection or microinjection. Suitably, in some embodiments, the reagent composition is introduced an oviduct by injecting the reagent composition into the lumen of the oviduct.

The reagent compositions disclosed herein may include a "nuclease system." As used herein, a "nuclease system" may include any rare-cutting endonuclease system capable of cutting a target DNA sequence in a genome or other DNA within a cell. The nuclease system may include a rare-cutting endonuclease that generally can be distinguished from other endonucleases (e.g., restriction enzymes) that may cut at several locations in a genome. The nuclease system may also include a guide polynucleotide that directs the endonuclease to a specific polynucleotide sequence. The nuclease system may produce a double strand break at the target DNA sequence or may nick the target DNA sequence. Nuclease systems such as engineered meganucleases, zinc finger nucleases (ZFN), transcription activator-like effector nucleases (TALEN), and CRISPR/Cas systems, are known in the art. The nuclease system of the present invention is suitably selected from zinc finger nucleases (ZFN), transcription activator-like effector nucleases (TALEN), and CRISPR/Cas systems. ZFNs and TALENs are artificial endonuclease proteins that can bind and cut DNA at specific sequences. The structure and functionality of ZFNs and TALENs are known in the art. See, e.g., Carlson et al., *Molecular Therapy Nucleic Acids* 1(1): e3 (2012).

CRISPR stands for "Clustered Regularly Interspaced Short Palindromic Repeats." A Cas protein, such as Cas9 or Cpf1, is a nuclease that can bind and cut DNA at specific sequences by means of a single-guide RNA (sgRNA). Several CRISPR/Cas systems are known in the art (See, e.g., US Patent Publication No. 20140170753, 20140234972; Mali et al., *Science* 339(6121): 823-826 (2013); Cong et al., *Science* 339(6121): 819-823; Shmakov et al., *Molecular Cell* 60: 1-13 (2015)).

Suitably, the nuclease system of the present invention includes a CRISPR/Cas system. In some embodiments, the RNA-programmable nuclease of the CRISPR/Cas system may include a Cas9 polypeptide or a Cpf1 polypeptide. Exemplary Cas9 and Cpf1 polypeptides are disclosed in the Examples and are well-known in the art.

The endonuclease of the nuclease system may be a protein or polypeptide or encoded by a polynucleotide (e.g., DNA or RNA). The guide polynucleotide of the nuclease system may be a polynucleotide (e.g., DNA or RNA).

In embodiments that include CRISPR-Cas nuclease systems, the Cas endonuclease may be a protein or encoded in polynucleotide (e.g., DNA or RNA). The guide RNA may be composed of single-stranded RNA or encoded in a DNA polynucleotide. The guide RNA may include a single guide RNA or include a crRNA and tracrRNA molecule (See, e.g., Alt-R™ CRISPR guide RNAs, Integrated DNA Technologies).

In some embodiments, the nuclease system may include an RNA-programmable nuclease polypeptide and a guide RNA polynucleotide. In some embodiments, the RNA-programmable nuclease polypeptide may include a Cas9 or Cpf1 polypeptide and the guide RNA may include a crRNA and a tracrRNA.

The reagent compositions disclosed herein may further include a single-stranded DNA (ssDNA) or double-stranded DNA (dsDNA) repair template. The ssDNA repair template may be a relatively short oligonucleotide (i.e., 10-150 nucleotides) or may be a relatively longer nucleotide sequences being, for example, 200-10,000 nucleotides in length. Methods for using longer ssDNA repair templates were previously disclosed in WO 2016/196887, the content of which is incorporated herein in its entirety. Methods for using and preparing shorter ssDNA repair templates and longer dsDNA repair templates are generally known in the art.

The reagent compositions disclosed herein may include an "exogenous polynucleotide." As used herein, an "exogenous polynucleotide" may include, without limitation, DNA (double-stranded or single-stranded) or RNA polynucleotides. The exogenous polynucleotide may encode a protein product, an RNA product, a DNA regulatory element, a variant DNA sequence, or any combinations thereof.

Protein products may be full-length proteins, fragments of proteins such as exons, fusion proteins, polypeptides, or peptides. The protein products may be expressed (e.g., exogenous sequence is transcribed and translated to produce protein product) when the exogenous polynucleotide is introduced into a cell. The protein products may become part of a fusion protein that becomes expressed in the cell when the exogenous sequence is introduced into a target DNA sequence or may be expressed as individual proteins.

The exogenous polynucleotide may be an RNA product. The RNA products may include RNAs involved in protein synthesis, RNAs involved in post-transcriptional modification or DNA replication, or regulatory RNAs. RNAs involved in protein synthesis may include, without limitation, mRNAs, rRNAs, tRNAs, or SRP RNAs. RNAs involved in post-transcriptional modification may include, without limitation, snRNAs, snoRNAs, or Y RNAs. Regulatory RNAs may include, without limitation, antisense RNAs, CRISPR RNAs, guide RNAs, long noncoding RNAs, microRNAs, siRNAs, piRNAs, tasiRNAs, 5'UTR sequences, 3'UTR sequences, RNA splicing regulatory sequences, IRES sequences, or polyA signal sequences.

The exogenous polynucleotide may encode DNA regulatory elements. DNA regulatory elements may be non-coding DNA sequences that regulate the transcription of genes or serve as recognition sequences for protein products or RNA products. Exemplary DNA regulatory elements may include, without limitation, promoters, enhancers, silencers, insulators, tissue-specific regulatory elements, or recognition sequences for protein products or RNA products. Recognition sequences for protein products or RNA products may include, without limitation, recognition sequences for site-specific recombinases or integrases such as FRT, loxP, rox, and attB/attP sequences. Promoters useful in the practice of the present invention include, without limitation, constitutive, inducible, temporally-regulated, developmentally regulated, chemically regulated, physically regulated (e.g., light regulated or temperature-regulated), tissue-preferred, and tissue-specific promoters. Promoters may include pol I, pol II, or pol III promoters. Suitable promoters for expression in plants include, without limitation, the 35S promoter of the cauliflower mosaic virus, ubiquitine, tCUP cryptic constitutive promoter, the Rsyn7 promoter, pathogen-inducible promoters, the maize In2-2 promoter, the tobacco PR-1a promoter, glucocorticoid-inducible promoters, estrogen-inducible promoters and tetracycline-inducible and tetracycline-repressible promoters. Those of skill in the art are familiar with a wide variety of additional promoters for use in various cell types.

The exogenous polynucleotide may encode a "variant DNA sequence." As used herein, a "variant DNA sequence" refers to a DNA molecule having a sequence that differs from a reference DNA sequence. A variant DNA sequence may include one or more copies of a DNA sequence that creates a repetitive (repeat) sequence or copy number variegation when the variant DNA sequence is inserted at a target DNA sequence. A variant DNA sequence may have 1, 2, 3, 4, 5, 6, 7, 8, 9, 10, or more insertions, deletions, or substitutions of a nucleotide base(s) relative to a reference molecule such as a target DNA sequence.

The exogenous polynuceltotide may encode any combination of protein products, RNA products, or DNA regulatory elements described herein.

The exogenous polynucleotide may also be a viral vector. The viral vector may be a virus particle or may be encoded on a polynucleotide such as a plasmid. The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors may be used. Suitable viral vectors that may be used in accordance with the present invention may include, without limitation, retroviral vectors, adeno-associated viral (AAV) vectors, adenoviral vectors, or herpes-simplex vectors. Retroviral vectors may include, for example, lentiviral vectors.

As used herein, "electroporating" or "electroporation" refers to the process of introducing materials (i.e., DNA, RNA, or proteins) into a cell using one or more pulses of electricity to open pores in the cell membrane. The present inventors have discovered that several different types of electroporators (T820, NEPA21, or CUY21EDIT II) and eletroporator parameters may be used in conjunction with the present invention. The electroporater may include tweezer-type electrodes that may be used to surround the reproductive organ of the subject.

The reproductive organ may be electroporated using a T820 electroporator. In such embodiments, the electroporation parameters may include: eight square-wave pulses with a pulse duration of 5 ms, a pulse interval of 1 s, and the electric field intensity may range anywhere from 10 V to 100 V (i.e. 10 V, 15 V, 20 V, 25 V, 30 V, 35 V, 40 V, 45 V, 50 V, 55 V, 60 V, 65V, 70 V, 75 V, 80 V, 85 V, 90 V, 95 V, or 100 V). In some embodiments, the electroporation parameters may include: eight square-wave pulses with a pulse duration of 5 ms, a pulse interval of 1 s, and an electric field intensity of 50 V.

The reproductive organ may be electroporated using a NEPA21 electroporator. In such embodiments, the electroporation parameters may include: poring pulse: 10V-100 V (i.e. 10 V, 15 V, 20 V, 25 V, 30 V, 35 V, 40 V, 45 V, 50 V, 55 V, 60 V, 65V, 70 V, 75 V, 80 V, 85 V, 90 V, 95 V, or 100 V), 5-ms pulse, 50-ms pulse interval, 3 pulse, 10% decay (±pulse orientation) and transfer pulse: 5 V-100 V (i.e. 5 V, 10 V, 15 V, 20 V, 25 V, 30 V, 35 V, 40 V, 45 V, 50 V, 55 V, 60 V, 65V, 70 V, 75 V, 80 V, 85 V, 90 V, 95 V, or 100 V), 50-ms pulse, 50-ms pulse interval, 3 pulse, 40% decay (±pulse orientation). In some embodiments, the electroporation parameters may include: poring pulse: 50 V, 5-ms pulse, 50-ms pulse interval, 3 pulse, 10% decay (±pulse orientation) and transfer pulse: 10 V, 50-ms pulse, 50-ms pulse interval, 3 pulse, 40% decay (±pulse orientation).

The reproductive organ may be eletroporated using a CUY21EDIT II electroporator. In such embodiments, the electroporation parameters may include: square (mA), (+/−), Pd V: 60 V or 80 V, Pd A: 50 mA-300 mA (i.e., 50 mA, 75 mA, 100 mA, 125 mA, 150 mA, 175 mA, 200 mA, 225 mA, 250 mA, 275 mA, or 300 mA), Pd on: 5.00 ms, Pd off: 50 ms, Pd N: 3, Decay: 10%, DecayType: Log. In some embodiments, the electroporation parameters may include: square (mA), (+/−), Pd V: 60 V or 80 V, Pd A: 150 mA, Pd on: 5.00 ms, Pd off: 50 ms, Pd N: 3, Decay: 10%, DecayType: Log.

Reproductive Organ Compositions

In another aspect, the present invention relates to reproductive organ compositions. The compositions may include a reproductive organ containing a fertilized zygote from a subject after a time period following insemination of the subject, the reproductive organ comprising a reagent composition, and the reagent composition comprising a nuclease system and/or an exogenous polynucleotide.

Uses of an Electroporator

In a still further aspect, the present invention relates to uses of an electroporator. The uses may include the use of an electroporator to introduce a reagent composition comprising a nuclease system and/or an exogenous polynucleotide into a reproductive organ containing a fertilized zygote from a subject after a time period following insemination of the subject.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

Illustrative Embodiments

The following embodiments are meant only to be illustrative and are not meant as limitations on the scope of the invention or of the appended claims.

Embodiment 1. A method for germline genome engineering in a subject having a reproductive organ containing a fertilized zygote comprising: (a) isolating or obtaining the reproductive organ from the subject after a time period following insemination of the subject; (b) introducing a reagent composition into the reproductive organ, the reagent composition comprising a nuclease system and/or an exogeneous polynucleotide; and (c) electroporating the reproductive organ (i.e., subjecting the reproductive organ to electroporation).

Embodiment 2. The method of embodiment 1, wherein the time period is between 0.5 days (12 hours) to 1.4 days (33.6 hours).

Embodiment 3. The method of embodiment 2, wherein the time period is about 0.7 days (16.8 hours).

Embodiment 4. The method of any one of the preceding embodiments, wherein the nuclease system comprises an RNA-programmable nuclease polypeptide and a guide RNA polynucleotide.

Embodiment 5. The method of embodiment 4, wherein the RNA-programmable nuclease polypeptide comprises a Cas9 polypeptide and the guide RNA comprises a crRNA and a tracrRNA.

Embodiment 6. The method of embodiment 4, wherein the RNA-programmable nuclease polypeptide comprises a Cpf1 polypeptide.

Embodiment 7. The method of any one of the preceding embodiments, wherein the reagent composition further comprises a single-stranded (ssDNA) repair template.

Embodiment 8. The method of any one of the preceding embodiments, wherein the reproductive organ is electroporated using a NEPA21 electroporator using the following parameters: poring pulse: 50 V, 5-ms pulse, 50-ms pulse interval, 3 pulse, 10% decay (±pulse orientation) and transfer pulse: 10 V, 50-ms pulse, 50-ms pulse interval, 3 pulse, 40% decay (±pulse orientation).

Embodiment 9. The method of any one of the preceding embodiments, wherein the reproductive organ is electroporated using a CUY21EDIT II electroporator using the following parameters: square (mA), (+/−), Pd V: 60 V or 80 V, Pd A: 150 mA, Pd on: 5.00 ms, Pd off: 50 ms, Pd N: 3, Decay: 10%, DecayType: Log.

Embodiment 10. The method of any one of the preceding embodiments, wherein the subject is inseminated by mating the subject with another subject.

Embodiment 11. The method of any one of the preceding embodiments, wherein the subject is a rodent (e.g., a mouse, rat, or hamster).

Embodiment 12. The method of any one of the preceding embodiments, wherein the reproductive organ is an oviduct.

Embodiment 13. The method of embodiment 12, wherein the reagent composition is introduced into the oviduct by injecting the reagent composition into the lumen of the oviduct.

Embodiment 14. A reproductive organ containing a fertilized zygote from a subject after a time period following insemination of the subject, the reproductive organ comprising a reagent composition, and the reagent composition comprising a nuclease system and/or an exogenous polynucleotide.

Embodiment 15. The reproductive organ of embodiment 14, wherein the time period is between 0.5 days (12 hours) to 1.4 days (33.6 hours).

Embodiment 16. The reproductive organ of embodiment 15, wherein the time period is about 0.7 days (16.8 hours).

Embodiment 17. The reproductive organ of any one of embodiments 14-16, wherein the nuclease system comprises an RNA-programmable nuclease polypeptide and a guide RNA polynucleotide.

Embodiment 18. The reproductive organ of embodiment 17, wherein the RNA-programmable nuclease polypeptide comprises a Cas9 polypeptide and the guide RNA comprises a crRNA and a tracrRNA.

Embodiment 19. The reproductive organ of embodiment 17, wherein the RNA-programmable nuclease polypeptide comprises a Cpf1 polypeptide.

Embodiment 20. The reproductive organ of any one of embodiments 14-19, wherein the reagent composition further comprises a single-stranded (ssDNA) repair template.

Embodiment 21. The reproductive organ of any one of embodiments 14-20, wherein the subject is a rodent (e.g., a mouse, rat, or hamster).

Embodiment 22. The reproductive organ of any one of embodiments 14-21, wherein the reproductive organ is an oviduct.

Embodiment 23. Use of an electroporator to introduce a reagent composition comprising a nuclease system and/or an exogenous polynucleotide into a reproductive organ containing a fertilized zygote from a subject after a time period following insemination of the subject.

Embodiment 24. The use of embodiment 23, wherein the time period is between 0.5 days (12 hours) to 1.4 days (33.6 hours).

Embodiment 25. The use of embodiment 24, wherein the time period is about 0.7 days (16.8 hours).

Embodiment 26. The use of any one of embodiments 23-25, wherein the nuclease system comprises an RNA-programmable nuclease polypeptide and a guide RNA polynucleotide.

Embodiment 27. The use of embodiment 26, wherein the RNA-programmable nuclease polypeptide comprises a Cas9 polypeptide and the guide RNA comprises a crRNA and a tracrRNA.

Embodiment 28. The use of embodiment 26, wherein the RNA-programmable nuclease polypeptide comprises a Cpf1 polypeptide.

Embodiment 29. The use of any one of embodiments 23-28, wherein the reagent composition further comprises a single-stranded (ssDNA) repair template.

Embodiment 30. The use of any one of embodiments 23-29, wherein the subject is a rodent (e.g., a mouse, rat, or hamster).

Embodiment 31. The use of any one of embodiments 23-30, wherein the reproductive organ is an oviduct.

EXAMPLES

The following examples are meant only to be illustrative and are not meant as limitations on the scope of the invention or of the appended claims.

Example 1—i-GONAD: a Robust Method for In Situ Germline Genome Engineering Using CRISPR Nucleases Abstract We present a robust method called improved-Genome editing via Oviductal Nucleic Acids Delivery (i-GONAD) that delivers CRISPR ribonucleoproteins to E0.7 embryos via in situ electroporation. The method generates mouse models containing single-base changes, kilobase-sized deletions, and knock-ins. The efficiency of i-GONAD is comparable to that of traditional microinjection methods, which rely on ex vivo handling of zygotes and require recipient animals for embryo transfer. In contrast, i-GONAD avoids these technically difficult steps, and it can be performed at any laboratory with simple equipment and technical expertise. Further, i-GONAD-treated females retain reproductive function, suggesting future use of the method for germline gene therapy.

Background

Recent advances in genome editing using clustered regularly interspaced short palindromic repeats (CRISPR)/CRISPR associated protein 9 (Cas9) enable production of gene knock-out animals easily and rapidly [1, 2, 3]. CRISPR animal genome engineering methods include three broad steps: mating of super-ovulated females and isolation of zygotes, microinjection of genome editing components into the zygotes, and transfer of microinjected zygotes into the oviducts of pseudopregnant females [1, 2]. These steps require (1) a very high level of technical expertise by the technicians who perform these procedures and (2) expensive apparatus, including micromanipulators. Because of the complex nature of the protocol, animal genome engineering experiments are difficult to perform in individual laboratories, and are typically performed in centralized cores, where highly trained personnel offer genome engineering services on a day-to-day basis. The development of methods that circumvent such complex steps enables animal genome engineering technologies to be performed by many more laboratories, not just cores. Some groups have investigated the use of in vitro electroporation of zygotes as an alternative to microinjection, and they successfully produced genome-edited fetuses and pups using this approach [4, 5, 6, 7, 8, 9]. Electroporation of zygotes overcomes the microinjection step, but this strategy still requires the other two difficult steps: isolation of zygotes for ex vivo handling and their transfer back into pseudopregnant females. We recently demonstrated that all three steps can be bypassed by performing in situ electroporation of zygotes.

To simplify germline genome editing, we developed a method called Genome-editing via Oviductal Nucleic Acids Delivery (GONAD), which does not require isolation of zygotes or their ex vivo handling for microinjection and subsequent transfer to recipient females [10]. GONAD is performed on pregnant mouse females bearing E1.5 (2-cell stage) embryos. The ovaries and oviducts are surgically exposed through an incision at a dorsolateral position, and genome editing reagents are injected into the oviductal lumen using a glass capillary pipette. Immediately after solution injection, the entire oviduct is subjected to electroporation using tweezer-type electrodes. After electroporation, the ovaries and oviducts are returned to their original position and the incision is sutured. The in situ genome-edited embryos subsequently develop to term, and the offspring are genotyped for the targeted mutation. We demonstrated that it is possible to create indel mutations at target loci in some of the fetuses with 28% efficiency (7/25) [10]. When developing this strategy, we realized that the method could be significantly improved by systematically testing various parameters, enabling the method to achieve precise genome editing. The improvements that needed to be achieved included methods for (1) small point mutation knock-in and large cassette knock-ins (not just indels); (2) germline transmission of the founder (G0) mutations; (3) reduction of mosaicism, which typically occurs if genome editing happens at the 2-cell stage and beyond; (4) testing of additional commercially available electroporators (the model used in our initial studies is no longer available; (5) ascertainment of the fertility of females following the GONAD procedure; and (6) determining whether the GONAD method works with AsCpf1, the second most commonly used CRISPR family nuclease.

In this study, we made major modifications to improve GONAD. We termed the new method improved GONAD (i-GONAD), because it offers much higher genome editing efficiencies. We demonstrate that the i-GONAD approach can be used to create germline-modified G1 offspring with genetic changes including large deletions and knock-ins. Furthermore, we demonstrate that i-GONAD is robust because many commonly used electroporators can be used. These features make i-GONAD easily adaptable for all laboratory personnel, including beginners or students who do not possess the skills needed to operate specialized equipment such as micromanipulators.

Results

GONAD on Day 0.7

In our first report on the GONAD method, experiments were performed at ~1.5 to 1.7 day post-mating. At this stage of pregnancy, embryos are at the 2-cell stage. Delivery of genome editing reagents at this stage results in a high frequency of mosaic embryos or fetuses [10]. The ideal time to deliver gene editing components would be one that corresponds to the 1-cell stage because it would reduce genetic mosaicism. To investigate the earliest time of editing component delivery, we tested GONAD at two separate time points, day 0.4 and day 0.7. We injected 1.0-1.5 µl of a solution containing enhanced green fluorescent protein (eGFP) messenger RNA (mRNA) (1 µg/µl) and trypan blue into oviduct lumens (schematic shown in FIG. 1A) and then performed in vivo electroporation using a BTX T820 instrument under previously described conditions [10]. Two days after mRNA delivery, 8-cell stage embryos were isolated from the treated females and observed for the presence of eGFP fluorescence. We did not observe appreciable eGFP in any of the embryos treated at the 0.4 day time point, whereas uniform eGFP fluorescence was observed in 13 of 31 embryos treated at the 0.7 day time point (FIG. 1B). One of the reasons for the lack of success at day 0.4 could be that cumulus cells tightly surround the zygotes at this stage (FIG. 1C, left), and this may hamper efficient electrophoretic delivery of nucleic acids to zygotes. In contrast, most zygotes at day 0.7 should be devoid of thick cumulus cells (FIG. 1C, right), permitting access of the injection mix to the zygotes. These results suggested that 0.7 day (~16 h) post-mating would be the best time to perform GONAD.

Generation of Foxe3 Knock-Out Lines by a Modified GONAD Protocol

Figure 2B:
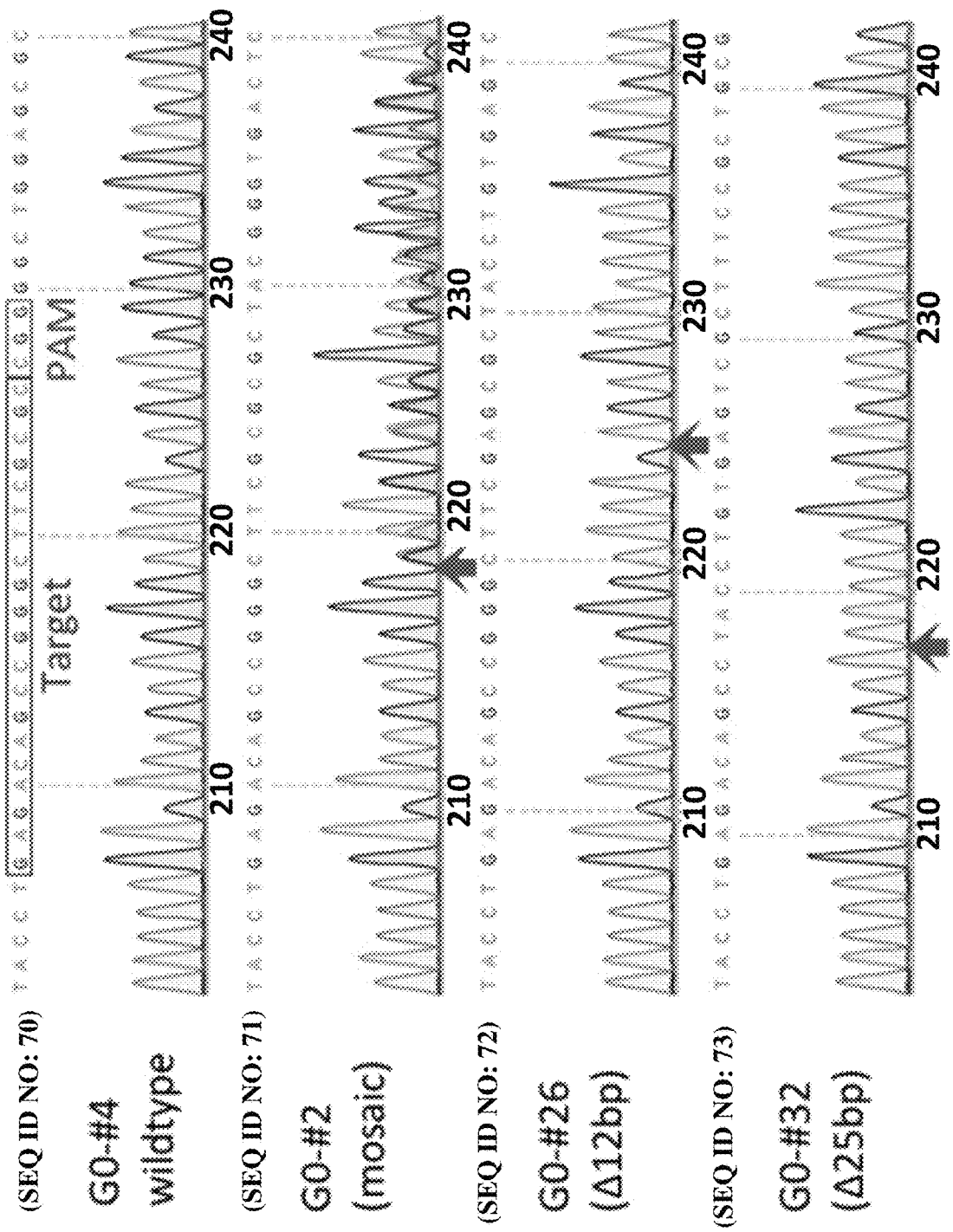

Next, we asked whether the GONAD method could be used to create gene-disrupted animal models. We chose the Foxe3 locus for gene targeting (FIG. 2A) because its inactivation causes abnormal development of the eye and cataracts in mice [11, 12]. GONAD was performed on 0.7-day pregnant Jcl:MCH(ICR) females using Cas9 mRNA and a single-guide (sg)RNA targeting the Foxe3 gene. The electroporation conditions used were 8 pulses of 50 V at 5 ms wave length. Seven of the eight GONAD-treated females delivered pups. Sequencing of genomic DNA isolated from the ears of G0 offspring demonstrated that 11 of 36 G0 pups (31%) had a mutated allele in the target locus (FIGS. 2B and 2C, Table 1). Notably, there was still a high frequency of pups with mosaic alleles (82% [9/11]), and mosaicism was absent from only two pups (18% [2/11]; G0-#26 and -#32 in FIG. 2B). Intercrossing of G0 founders resulted in G1 offspring, some of which exhibited the expected cataract phenotype (FIGS. 2D and 2E). Sequencing of genomic DNA isolated from G1 mice with cataracts revealed germline transmission of the mutated alleles. Taken together, these results indicate that GONAD can be used to create gene-disrupted mouse models.

TABLE 1

Generation of Foxe3 knock-out mice using conventional GONAD and i-GONAD approaches.

| Mice | Concentration of CRISPR/Cas9 components | Electroporator used | No. of G0 fetuses/pups obtained | No. of G0 fetuses/pups with mutation | No. of mosaic fetuses/pups |
|---|---|---|---|---|---|
| #1 | conventional GONAD | BTX T820 | 7 | 4 | 4 |
| #2 | | | | | |
| #3 | Cas9 mRNA | | 13 | 3 | 3 |
| #4 | (1.5 µg/µl) | | | | |
| #5 | Foxe3_3_Cr_sgRNA | | 11 | 3 | 2 |
| #6 | (0.8 µg/µl) | | | | |
| #7 | | | 5 | 1 | 0 |
| #8 | | | | | |
| total | | | 36 | 11 (31%) | 9 (82%) |
| #9 | i-GONAD | BTX T820 | 2 | 2 | 1 |
| #10 | Cas9 protein | | 2 | 2 | 1 |
| #11 | (1 mg/ml) | | 9 | 9 | 7 |
| #12 | crRNA-Foxe3-3-Cr | CUY21EDIT II | 6 | 5 | 2 |
| #13 | (30 µM) | | 5 | 5 | 4 |
| #14 | tracrRNA (30 µM) | | 3 | 3 | 0 |
| #15 | | | 9 | 9 | 5 |
| total | | | 36 | 35 (97%) | 20 (57%) |

Higher Genome Editing Efficiency Using CRISPR RNA (crRNA)+Trans-Activating crRNA (tracrRNA)+Cas9 Protein (ctRNP) Complexes It is now becoming increasingly clear that the use of Cas9 protein, instead of Cas9 mRNA [7, 13, 14], together with crRNA+tracrRNA (two-part guide RNA), instead of a single guide RNA (sgRNA), yields higher genome editing efficiencies [13]. We thus examined the combinatorial use of these components (crRNA+tracrRNA+Cas9 protein: ctRNP) for GONAD-mediated genome editing. We targeted the Foxe3gene, as an example, using the same guide sequence as in the previous experiment except that annealed crRNA+tracrRNA were used in place of sgRNA, and Cas9 protein was used in place of Cas9 mRNA. A mixture of ctRNP complexes was injected into the oviduct lumen of seven pregnant Jcl:MCH(ICR) females at day 0.7. The oviduct was electroporated in vivo using the same electroporator as before or using the CUY21Edit II electroporator. Embryos were isolated at E13.5 or E17.5. All seven females contained fetuses (totaling 36). Surprisingly, nearly all had indel mutations within the Foxe3 target sequence ($^{35}/_{36}$, 97%), which was much higher than the frequency when Cas9 mRNA was used (31%, p<0.001) (Table 1; Table 2). Note that 57% ($^{20}/_{35}$) of fetuses exhibited mosaicism. Although this is lower than the frequency obtained when using Cas9 mRNA (82%), it was not statistically significant (p=0.139). These results suggest that combinational use of crRNA, tracrRNAs, and Cas9 protein (ctRNP) offers the highest efficiency of genome editing with GONAD. We termed this RNP-based GONAD as improved GONAD (i-GONAD).

TABLE 2

Efficiencies of Foxe3 gene editing. CRISPR components used were either Cas9 mRNA/sgRNA or Cas9 protein/CRISPR RNA (crRNA)/trans-activating crRNA (tracrRNA) (see Table 1 for details)

| Cas9 | No. Mice Treated | No. G0 fetuses/newborns obtained | No. G0 mice with mutation | No. mosaic fetuses/pups |
|---|---|---|---|---|
| mRNA | 8 | 36 | 11 (31%) | 9 (82%) |
| protein | 7 | 36 | 35 (97%) | 20 (57%) |

Generation of Gene-Corrected Animal Models Using i-GONAD

Figure 3A:
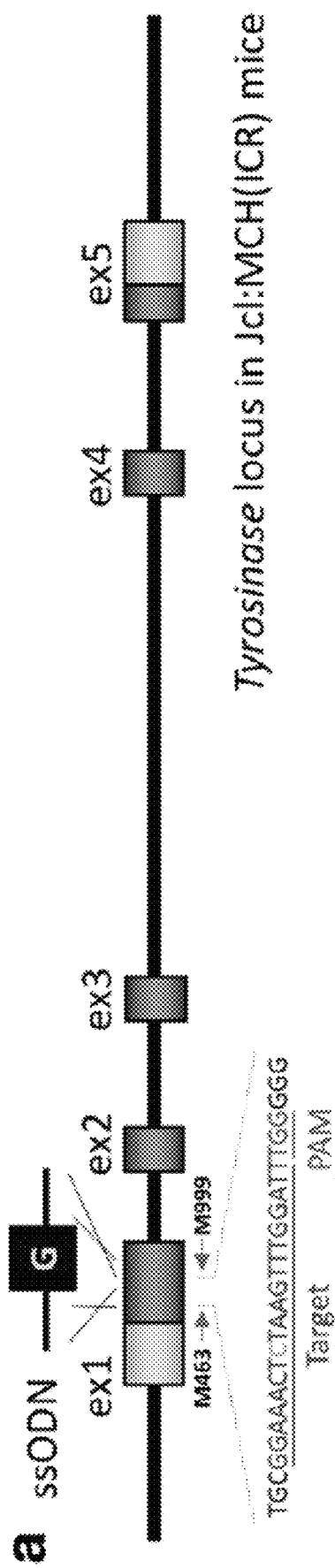
FIGS. 3A-3D show creating small genetic change animal models using the i-GONAD method. Restoration of Tyrgene of albino Jcl:MCH(ICR) mice by single-stranded oligo donor (ssODN)-based knock-in with the i-GONAD method.
Figure 3B:
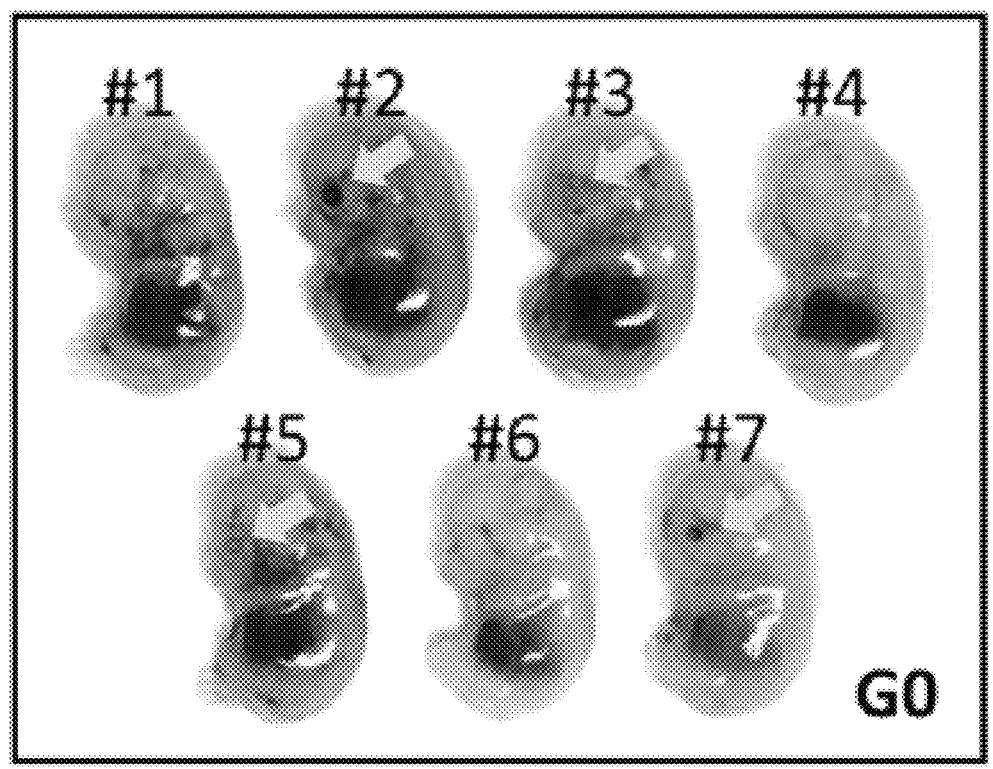
Figure 3C:
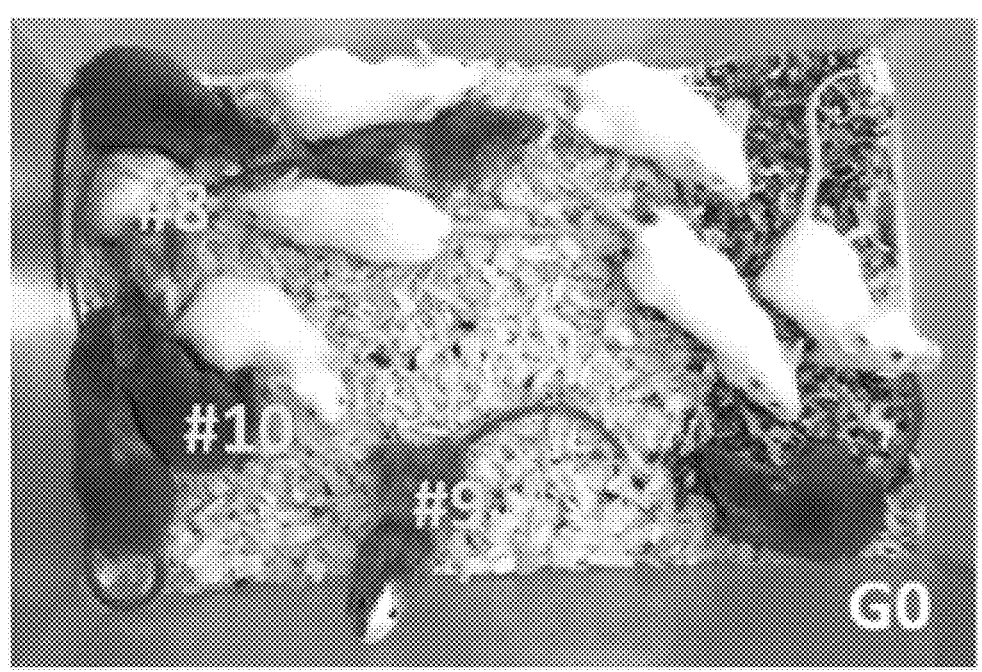

Next, we asked whether i-GONAD could be used to make small genetic changes. We chose the codon 103 of the Tyrosinase (Tyr) gene as an example. The mice containing codon TGT (cysteine) at this location will have normal pigmentation in coat and eyes (regarded as the wild-type phenotype, for example, C3H/He strain mice), and mice with TCT (serine) will have the non-pigmented phenotype of albino coat color and clear eyes (regarded as a mutant phenotype, for example, Jcl:MCH(ICR) strain) [15], due to reduced tyrosinase enzyme activity. We designed a gRNA for a region spanning the point mutation and constructed a single-stranded oligo donor (ssODN) that corresponds to the wild-type sequence of Tyr (FIG. 3A) to rescue the mutant phenotype in Jcl:MCH(ICR) strain (non-pigmented) to the wild-type (pigmented) phenotype.

i-GONAD was performed in five pregnant Jcl:MCH(ICR) females. A total of 32 offspring from these females were harvested at different stages of gestation (from E14.5 to E19.5), or postnatally. Fifteen (47%) of these samples exhibited the expected phenotype of dark eye pigmentation (in fetuses) or agouti coat color (in newborn pups; FIGS. 3B and 3C). Sequence analysis demonstrated that at least one allele had the corrected sequence (C to G) at the target site in all of the offspring with a normal pigmentation phenotype (FIG. 3D; Table 3).

TABLE 3

Correction of Tyr mutation by ssODN knock-in using the i-GONAD method.

| Female mice | Concentration of CRISPR/Cas9 components | Electroporator used | No. of G0 fetuses/pups obtained | No. of G0 fetuses/pups with modified allele | No. of G0 fetuses/pups with repaired allele | No. of G0 fetuses/pups with indel mutation | No. of mosaic fetuses/pups |
|---|---|---|---|---|---|---|---|
| #1 | Cas9 protein | BTX T820 | 4 | 4 | 1 | 4 | 0 |
| #2 | (1 mg/ml) | | 7 | 7 | 3 | 7 | 5 |
| #3 | crRNA-ICR-tyr | | 4 | 4 | 1 | 4 | 2 |
| #4 | (30 µM) | | 4 | 3 | 3 | 3 | 2 |
| #5 | tracrRNA(30 µM) | | 13 | 11 | 7 | 10 | 9 |
| total | ssODN-tyr | | 32 | 29 (91%) | 15 (47%) | 28 (88%) | 18 (62%) |
| #6 | (2 µg/µl) | NEPA21 | 7 | 7 | 4 | 6 | 3 |
| #7 | | | 10 | 7 | 3 | 7 | 5 |
| #8 | | | 4 | 4 | 4 | 2 | 2 |
| #9 | | | 4 | 4 | 2 | 4 | 2 |
| #10 | | | 0 | 0 | 0 | 0 | 0 |
| #11 | | | 7 | 5 | 3 | 5 | 3 |
| total | | | 32 | 27 (84%) | 16 (50%) | 24 (75%) | 15 (56%) |
| #12 | | CUY21EDIT II | 6 | 6 | 2 | 6 | 5 |
| #13 | | | 4 | 4 | 3 | 2 | 2 |
| total | | | 10 | 10 (100%) | 5 (50%) | 8 (80%) | 7 (70%) |
| total of all the experiments | | | 74 | 66 (89%) | 36 (49%) | 60 (81%) | 40 (61%) |

Figure 6:
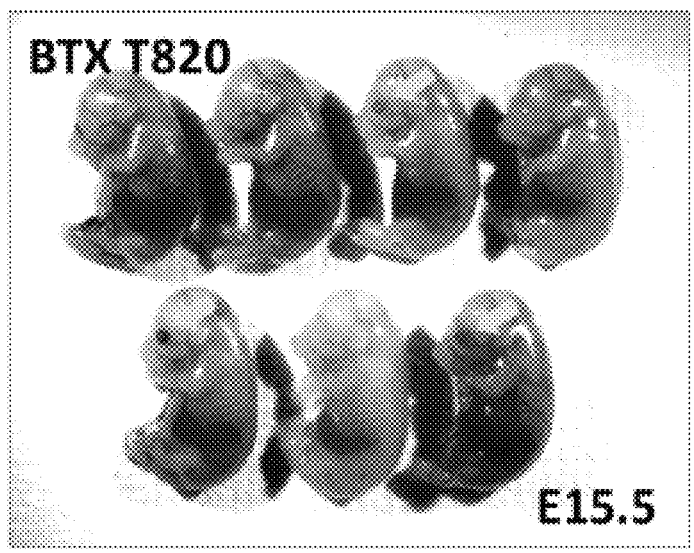
FIG. 6 shows fetuses recovered from the i-GONAD procedure to edit the Tyr-gene. Data shows that i-GONAD can produce comparable levels of genome editing using electroporators from three different manufacturers. The pigmented eyes of the fetuses are indicated by yellow arrows.
Figure 6:
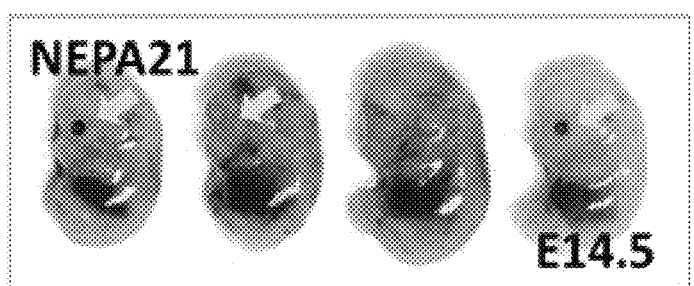
Figure 6:
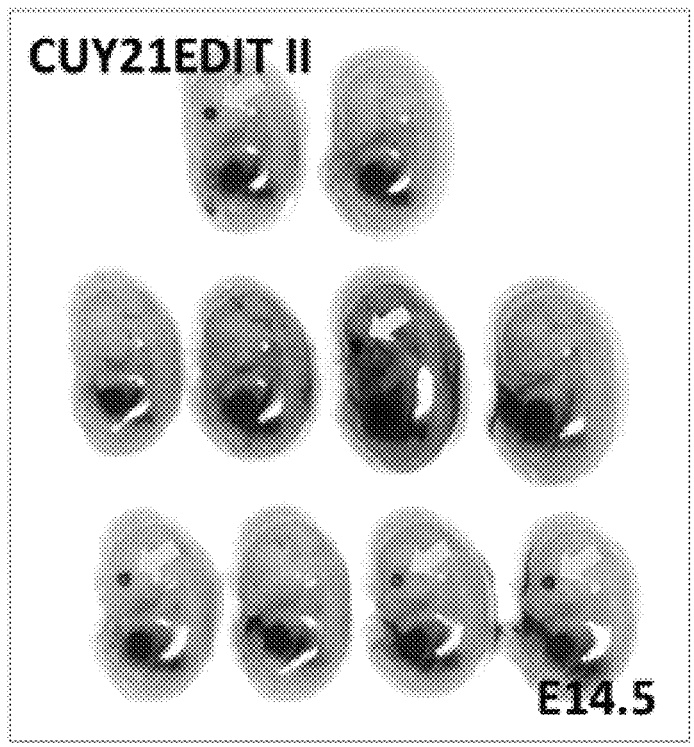

The original experiments were performed using a BTX T820 electroporator, a model that is no longer manufactured. We therefore tested two newer electroporators, NEPA21 (Nepa Gene Co) and CUY21EDIT II (BEX Co). Six females were subjected to i-GONAD using NEPA21. This yielded 32 offspring, of which 16 (50%) showed the expected genetic change and the phenotypic change of eye pigmentation or coat color (Table 3; Table 4). Two females were subjected to i-GONAD using the CUY21EDIT II electroporator, and the fetuses were analyzed at E14.5. Of 10 fetuses obtained, 5 (50%) showed the expected genetic change as well as the phenotypic change (eye pigmentation or coat color) (Table 3; Table 4). Highly consistent genome editing efficiencies (47%, 50%, and 50%) were thus obtained from three different electroporators (FIG. 6), demonstrating the robustness and reproducibility of i-GONAD. These results suggest that i-GONAD can be used for high-efficiency gene correction via co-delivery of a ssODN repair donor.

TABLE 4

Genome editing efficiency of the Tis21 locus using the i-GONAD method.

| No. mice treated | Concentration of ssDNA | No. G0 fetuses/newborns obtained | No. G0 mice with modified allele | No. G0 mice with knock-in allele |
|---|---|---|---|---|
| 2 | 0.85 µg/µl | 14 | 5 (35%) | 1 (7%) |

Figure 3D:
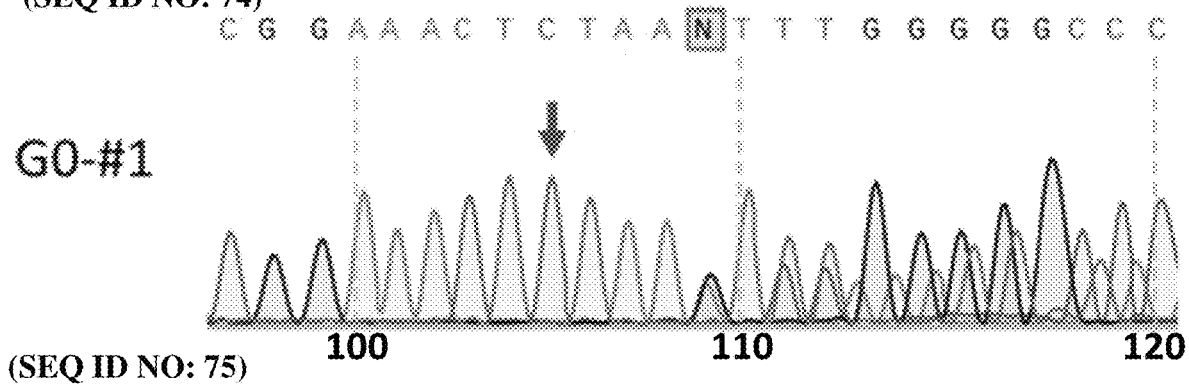
Figure 3D:
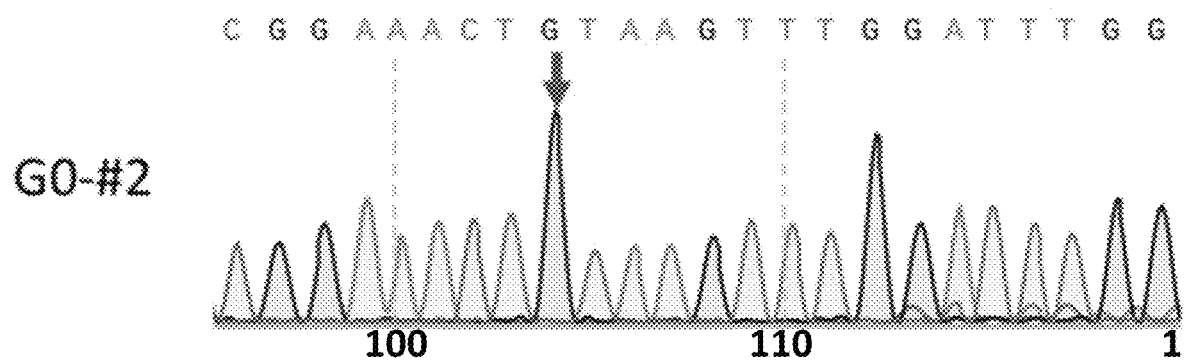
Figure 3D:
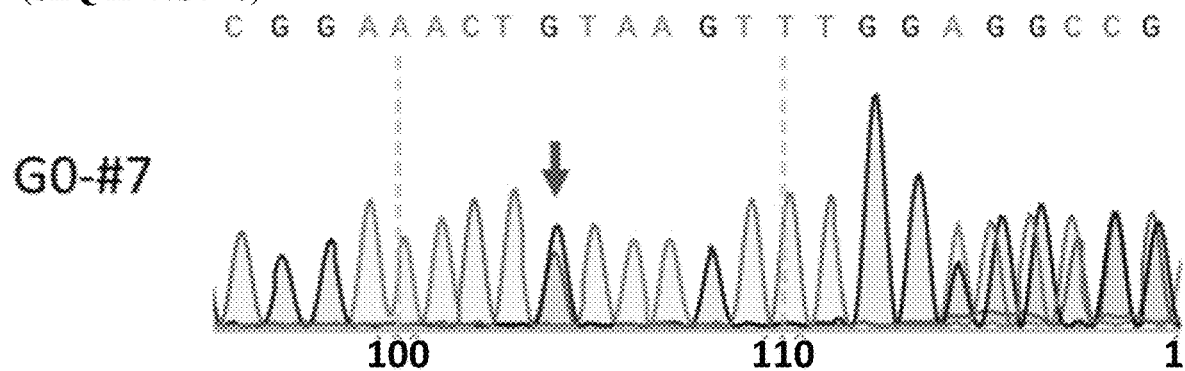

Eighty-three percent ($30/36$) of the offspring with the pigmentation phenotype were found in three experiments to have indel mutations around the target region of their second allele (FIG. 3D). Of note, 79% ($30/38$) of the unpigmented offspring thought not to be repaired had indel mutations. Considering gene correction and indels together, a total of 89% ($66/74$) of G0 offspring were genome-edited (Table 3;

Table 4). These results further support the conclusion that i-GONAD yields very high efficiencies of genome editing.

Figure 7A:
Figure 7A:
Figure 8A:
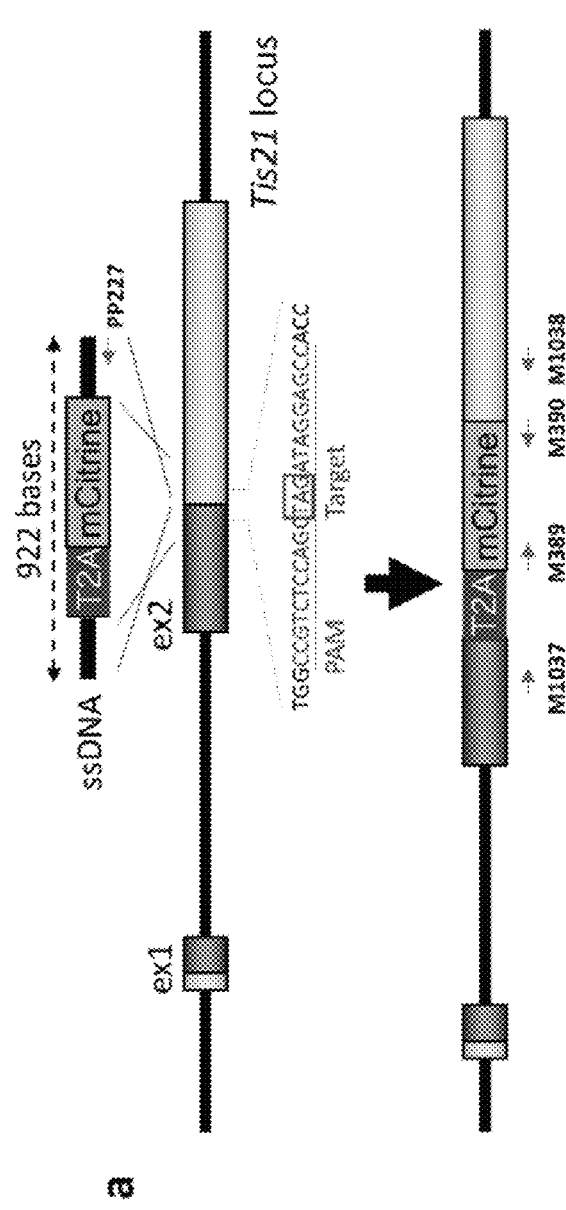
FIGS. 8A-8D show generation of reporter knock-in mice at the Tis21 locus using the i-GONAD method.
Figure 8B:
Figure 8C:
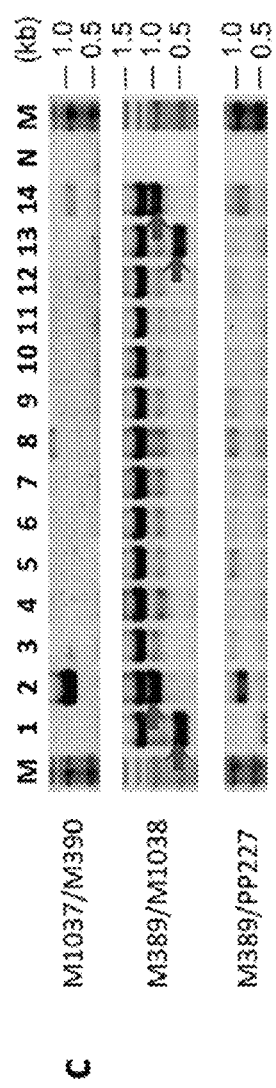
Figure 8D:
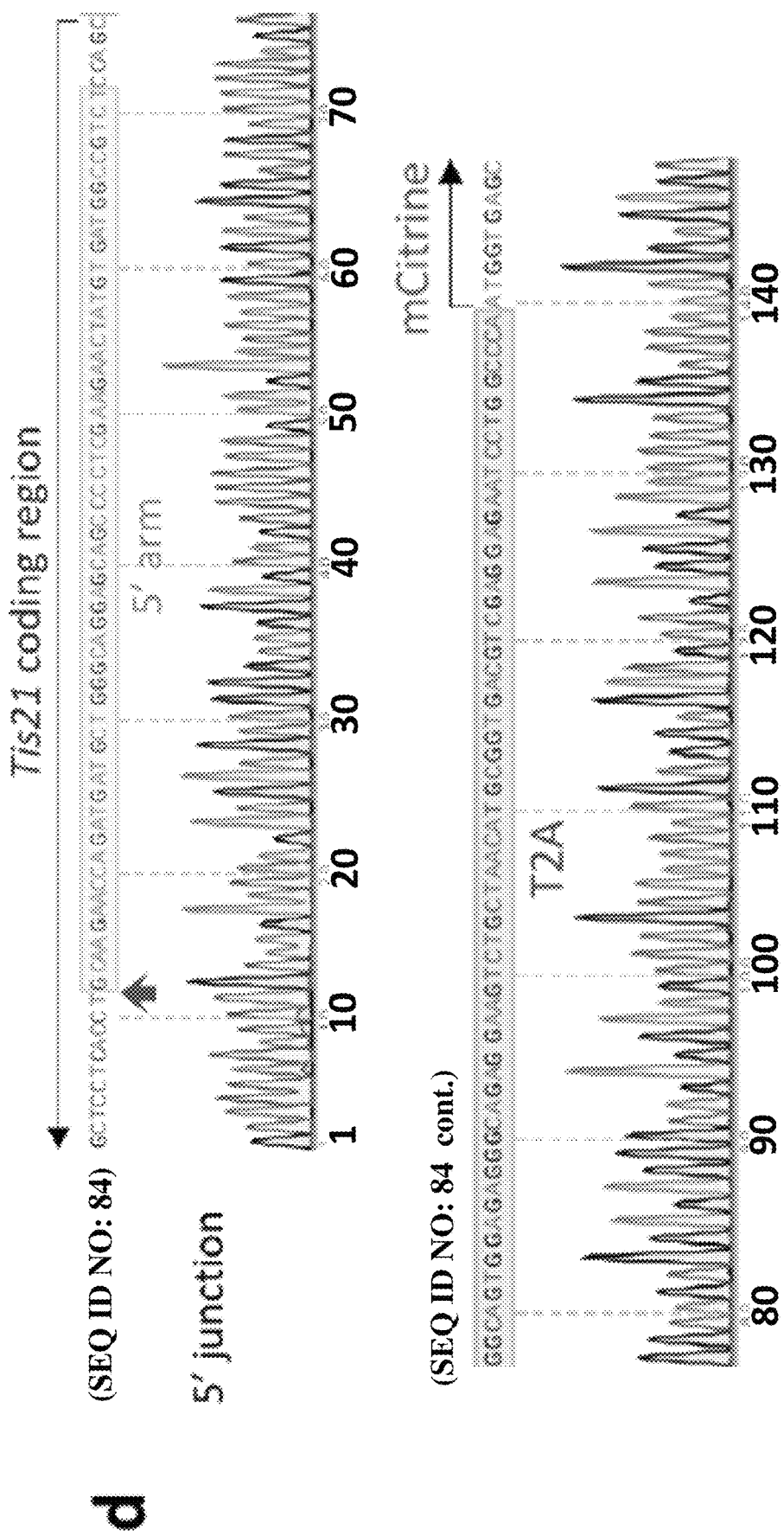

Three representative founder mice containing the repaired allele (G0-#8: 5% mosaic, G0-#9: 60% mosaic, G0-#10: 100% mosaic [based on the coat color]; FIG. 3C) were bred with Jcl:MCH(ICR) mice to assess germline transmission of the repaired allele. Although we did not obtain rescued progeny from G0-#8 (0/43), pups exhibiting an agouti coat color were obtained from founders G0-#9 and -#10 (#9 [8/18] and #10 [30/30]) (FIGS. 7A and Table 5).

TABLE 5

Germline transmission rate.

| G0 mice | No. G1 newborns obtained | No. G1 newborns with agouti coat color |
|---|---|---|
| #8 | 43 | 0 |
| #9 | 18 | 8 |
| #10 | 30 | 30 |

Figure 4D:
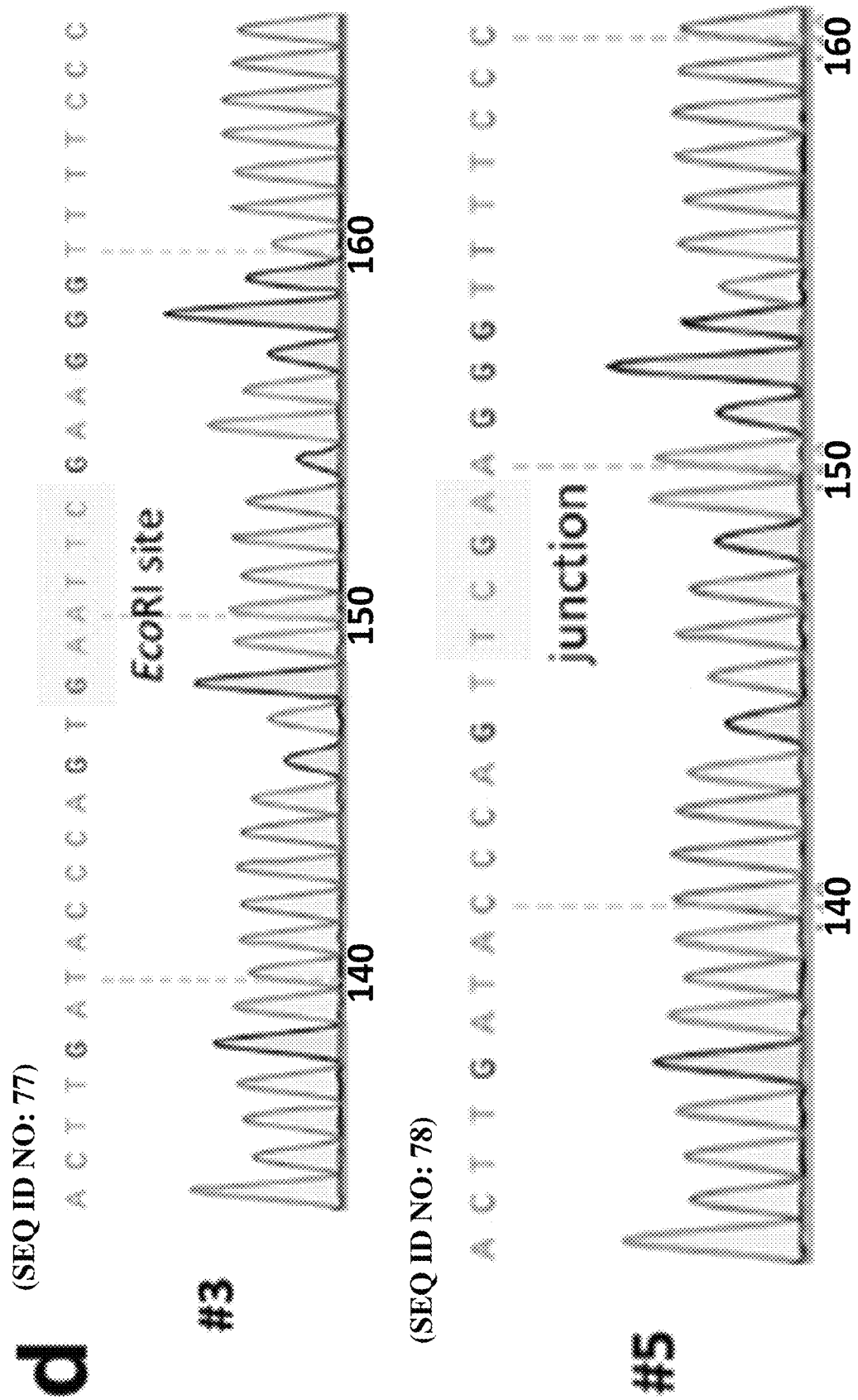

Comparison of the Genome Editing Efficiencies Between i-GONAD and Microinjection Methods We compared the genome editing efficiency of i-GONAD with that of the microinjection-based approach. For this study, we used the i-GONAD dataset presented above and compared it with microinjection of isolated zygotes. Oocytes from 35 super-ovulated Jcl:MCH(ICR) females were in vitro fertilized (IVF) to generate zygotes for microinjection. We injected 339 such zygotes with CRISPR reagents and cultured them. Of these 242 (71%) advanced to the 2-cell stage, and they were then transferred to 12 recipient females (Table 6). The females were euthanized at E14.5 or E15.5. Of 62 fetuses recovered, 32 (52%) had pigmented eyes. Sequencing analysis showed that the fetuses with pigmented eyes had the corrected sequence at the target site. Considering gene correction and indels together, a total of 79% (49/62) of G0 fetuses were genome-edited. These data, directly comparing genome editing using i-GONAD with standard microinjection-based techniques, clearly demonstrate that the efficiency is comparable between the two strategies (p=0.103). There was a somewhat lower mosaicism in genome-edited fetuses from microinjection (21/49, 43%; Table 6) compared with the i-GONAD approach (40/66, 61%; Table 3), but the difference was not statistically significant (p=0.059). Notably, the standard microinjection-based approach needed about 2.5 times more animals when the Jcl:MCH(ICR) strain was used: 20 mice were required to obtain 10 correctly genome-edited mice (11 females as egg donors+1 male as sperm donor for IVF+4 pseudopregnant females+4 vasectomized males), whereas i-GONAD used only 8 mice (4 embryo donors mated with 4 stud males).

precise joining of the genomic ends, we provided a ssODN donor containing short homology sequences to the two cleaved ends. The ssODN also included an EcoRI site for use in a restriction fragment length polymorphism (RFLP) assay. We injected a solution containing Cas9 protein, two crRNA/tracrRNAs, and the ssODN into the oviduct lumen of eight E0.7 pregnant C57BL/6JJcl females and performed in vivo electroporation. Of these, only four females remained pregnant, from which six G0 pups were recovered through caesarean section. Genotyping of the pups revealed that three (50%) exhibited large deletions in their agouti locus (G0-#3 and -#5) and/or agouti coat color (G0-#4 and -#5) (FIGS. 4B-4D; Table 7). Notably, one pup (G0-#3; 1/6 [17%]) had a correctly inserted ssODN at the target site, while another (G0-#5) showing agouti coat color did not have the insertion (FIGS. 4D and 4E). The polymerase chain

TABLE 6

Correction of Tyr mutation by zygote microinjection of CRISPR/Cas9 components.

| Exp. | Eggs injected | Embryos transferred | No. of G0 fetuses obtained | No. of G0 fetuses with modified allele | No. of G0 fetuses with repaired allele | No. of G0 fetuses with indel mutation | No. of mosaic fetuses |
|---|---|---|---|---|---|---|---|
| 1 | 64 | 50 | 3 | 1 | 1 | 0 | 0 |
| 2 | 116 | 93 | 32 | 24 | 17 | 16 | 8 |
| 3 | 159 | 99 | 27 | 24 | 14 | 19 | 13 |
| total | 339 | 242 | 62 | 49 (79%) | 32 (52%) | 35 (56%) | 21 (43%) |

Generation of Large Genomic Deletion Animal Models Using i-GONAD

We next asked whether the i-GONAD method could be used to generate mice with large genomic deletions by targeting a retrotransposon sequence present in the first intron of the agouti locus in C57BL/6JJcl mice [16]. A genomic region spanning 16.2 kb containing the retrotransposon sequence was targeted for deletion by making two cleavages that flank the retrotransposon insertion site (FIG. 4A). The deletion of this region should result in a coat color change from black to agouti mice (FIG. 4B). To aid in the reaction (PCR) did not yield an amplicon from the G0-#4 agouti pup, suggesting that one or both of the primer binding sites may have been deleted. Interestingly, the G0-#6 pup, one that showed neither a large deletion at the target locus nor agouti coat color, had indel mutations at both of the cleavage sites (Table 7; Table 8). The percentage of individual pups that were genome-edited (large deletions and short indels taken together) was 67% (4/6) (Table 8). These data suggest that i-GONAD can create large genomic deletions.

TABLE 7

Restoration of agouti gene expression by elimination of retrotransposon sequence using the i-GONAD method.

| Female Mice | Concentration of CRISPR/Cas9 components | Electroporator used | No. of G0 mice obtained | No. of G0 mice with modified allele | No. of G0 mice with repaired allele | Knock-in of ssODN |
|---|---|---|---|---|---|---|
| #3 | Cas9 protein | BTX T820 | 2 | 0 | 0 | 0 |
| #4 | (1 mg/ml) | | 0 | 0 | 0 | 0 |
| #7 | Agouti-crRNA- | | 0 | 0 | 0 | 0 |
| #8 | 1 (15 µM) | | 0 | 0 | 0 | 0 |
| #1 | Agouti-crRNA- | NEPA21 | 1 | 1 | 1 | 1 |
| #2 | 2 (15 µM) | | 0 | 0 | 0 | 0 |
| #5 | tracrRNA | | 1 | 1 | 1 | 0 |
| #6 | (30 µM) ssODN (2 µg/µl) | | 2 | 2 | 1 | 0 |
| total | | | 6 | 4 (67%) | 3 (50%) | 1 (17%) |

TABLE 8

Efficiencies of agouti gene editing (see Table 7 for details)

| No. mice treated | No. G0 newborns obtained | No. G0 mice with modified allele | No. G0 mice with deletion/ agouti | No. G0 mice with ssODN insertion |
|---|---|---|---|---|
| 8 | 6 | 4 (67%) | 3 (50%) | 1 (17%) |

Knocking-In Long ssDNA Donors Using i-GONAD

We previously demonstrated that knocking-in long DNA sequences can be achieved efficiently by using ssDNA donors [17, 18, 19]. We asked whether long ssDNA donors could be used with i-GONAD to create knock-in alleles. The Pitx3 and Tis21 genes were selected for these knock-in experiments in order to create reporter models containing T2A-mCitrine fusion cassettes. See FIGS. 5A-5D and FIGS. 8A-8D; Table 9.

TABLE 9

Genome editing efficiency of the Tis21 locus using the i-GONAD method.

| No. mice treated | Concentration of ssDNA | No. G0 fetuses/ newborns obtained | No. G0 mice with modified allele | No. G0 mice with knock-in allele |
|---|---|---|---|---|
| 2 | 0.85 µg/µl | 14 | 5 (35%) | 1 (7%) |

Figure 5D:
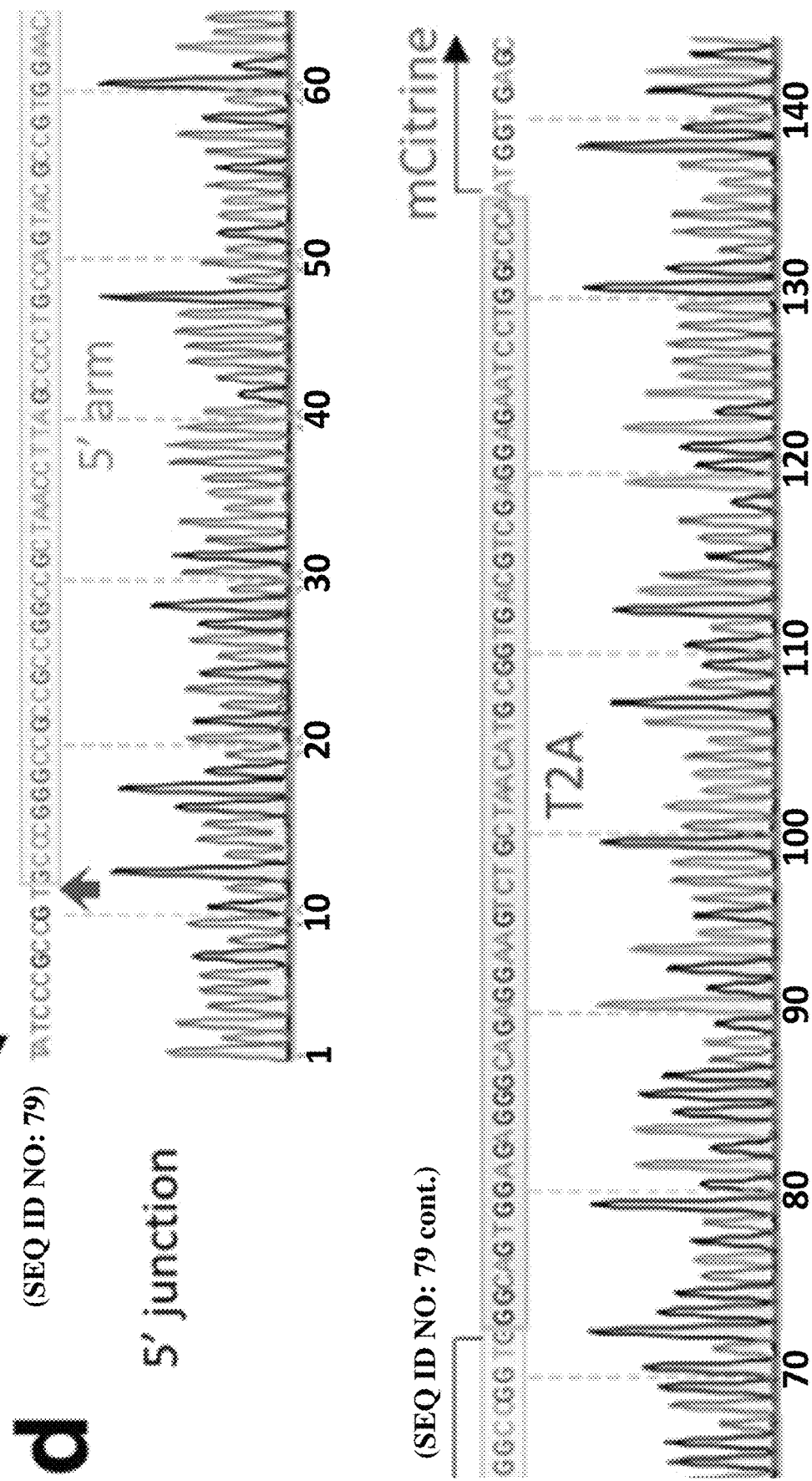

We inserted a 783-bp T2A-mCitrine cassette immediately upstream of the stop codon of the Pitx3 gene (FIG. 5A). The ssDNA donor was prepared using an in vitrotranscription and reverse transcription (ivTRT) method described previously [17]. The concentration of Cas9 protein (1 mg/ml) and crRNA/tracrRNA (30 µM) was the same as used in the previous experiment. The ssDNA donor was used at concentrations of 1.3 or 1.4 µg/µl in the i-GONAD procedure. G0 fetuses were dissected at E12.5 and were observed for fluorescence under a dissecting microscope. The lenses of some fetuses exhibited fluorescence (FIG. 5B), suggestive of correct insertion of the fusion cassette. This observation is similar to the previously created knock-in model [20]. The correct insertion of the cassette at the target site was confirmed by PCR amplification and sequencing of the target region (FIG. 5C), which revealed that 15% (5/34) of samples contained the knock-in cassettes (FIG. 5D and Table 10). Of note, the other alleles of these five samples contained indel mutations. Also, 16 fetuses that did not contain the insertion of the T2A-mCitrine cassette contained indel mutations (Table 10; Table 11). Collectively, the percentage of G0 individuals that had been genome-edited (knock-in and/or indel mutations) was 62% (21/34) (Table 10). No random insertions were detected in the fetuses that did not contain the target insertion allele.

TABLE 10

Genome editing efficiency of the Pitx3 locus by the i-GONAD method

| No. mice treated | Concentration of ssDNA | No. G0 fetuses/ newborns obtained | No. G0 mice with modified allele | No. G0 mice with knock-in allele |
|---|---|---|---|---|
| 2 | 1.3 µg/µl | 21 | 11 (52%) | 2 (10%) |
| 1 | 1.4 µg/µl | 13 | 10 (77%) | 3 (23%) |
| total 3 | — | 34 | 21 (62%) | 5 (15%) |

TABLE 11

Generation of reporter gene knock-in mice using i-GONAD with ssDNA as donors.

| Female mice | Locus | Concentration of ssDNA | No. of G0 fetuses obtained | No. of G0 fetuses with modified allele* | No. of G0 knock-in fetuses |
|---|---|---|---|---|---|
| #1 | Pitx3 | 1.3 µg/µl | 8 | 5 | 1 |
| #2 | | | 13 | 6 | 1 |
| #3 | | 1.4 µg/µl | 13 | 10 | 3 |
| total | | | 34 | 21 (62%) | 5 (15%) |
| #4 | Tis21 | 0.85 µg/µl | 11 | 2 | 1 |
| #5 | | | 3 | 3 | 0 |
| total | | | 14 | 5 (36%) | 1 (7%) |

Figure 9C:
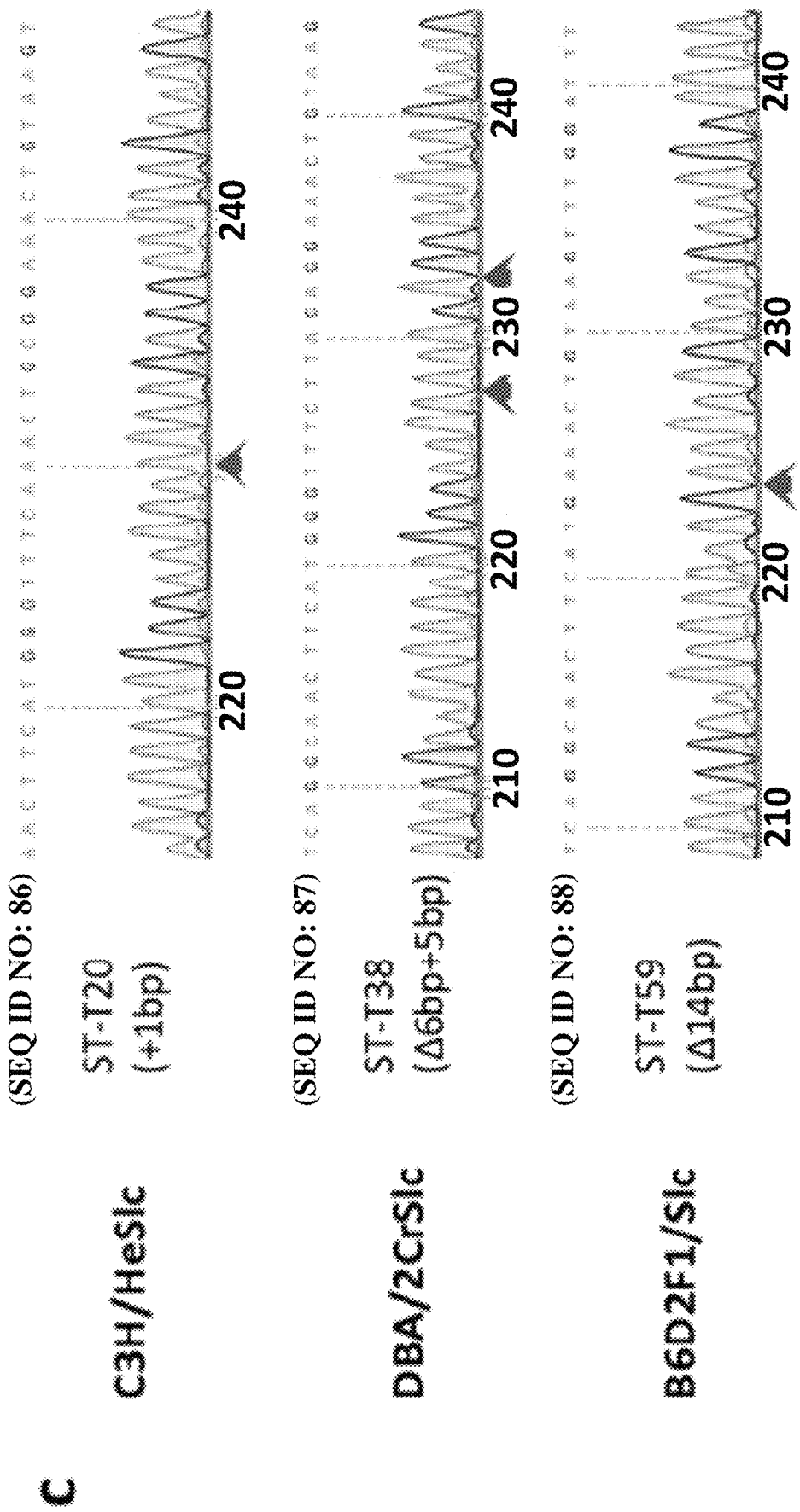
Figure 10A:
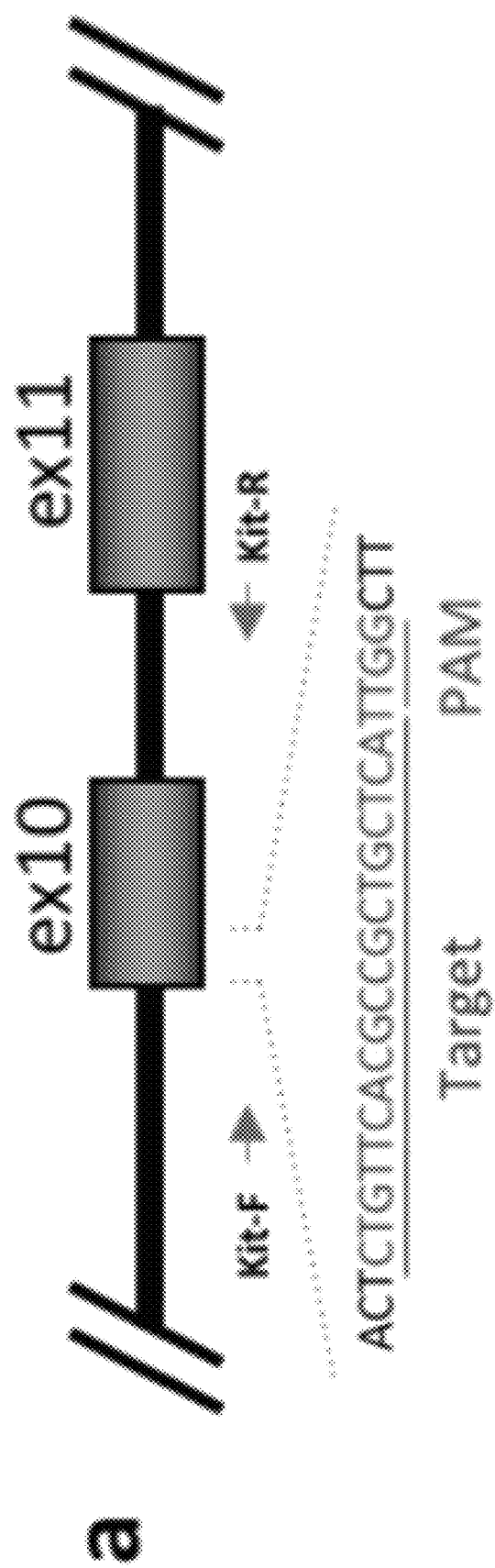
FIGS. 10A-10C show generation of indel mutation in the Kit locus of C3H/HeSlc and C57BL/6NCrSlc mouse strains using i-GONAD.
Figure 10B:
Figure 10B:
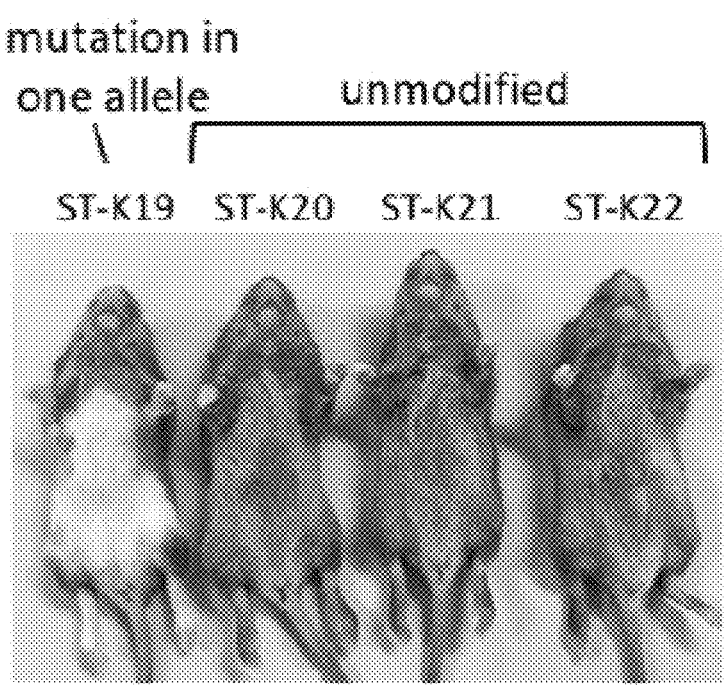
Figure 10B:
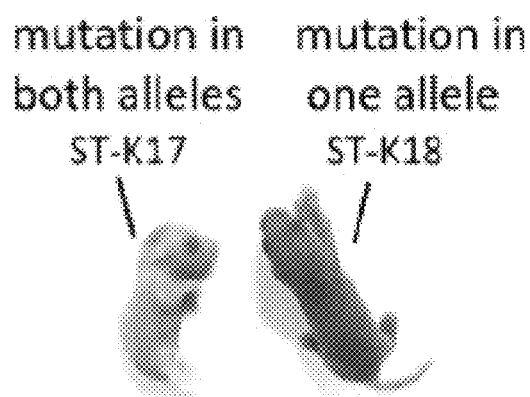
Figure 10C:
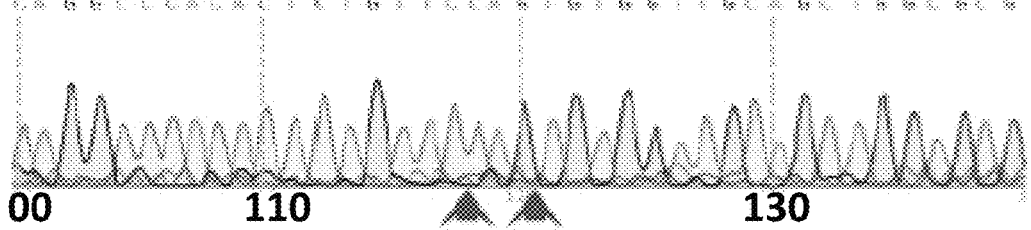
Figure 10C:
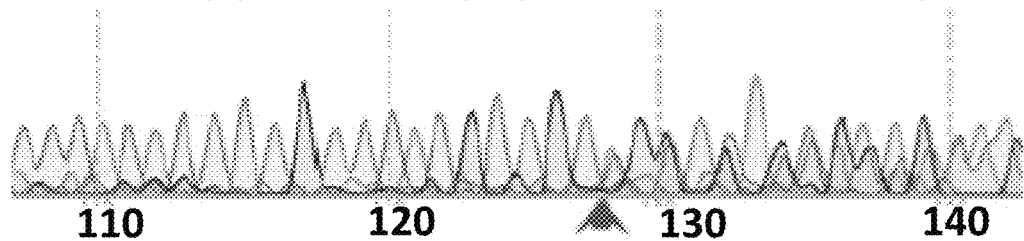
Figure 10C:
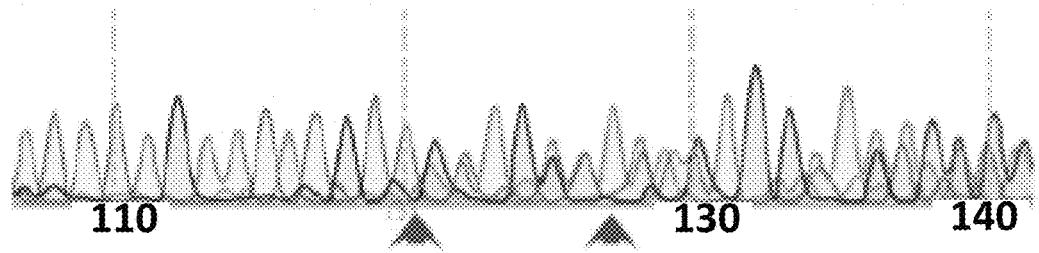
Figure 11A:
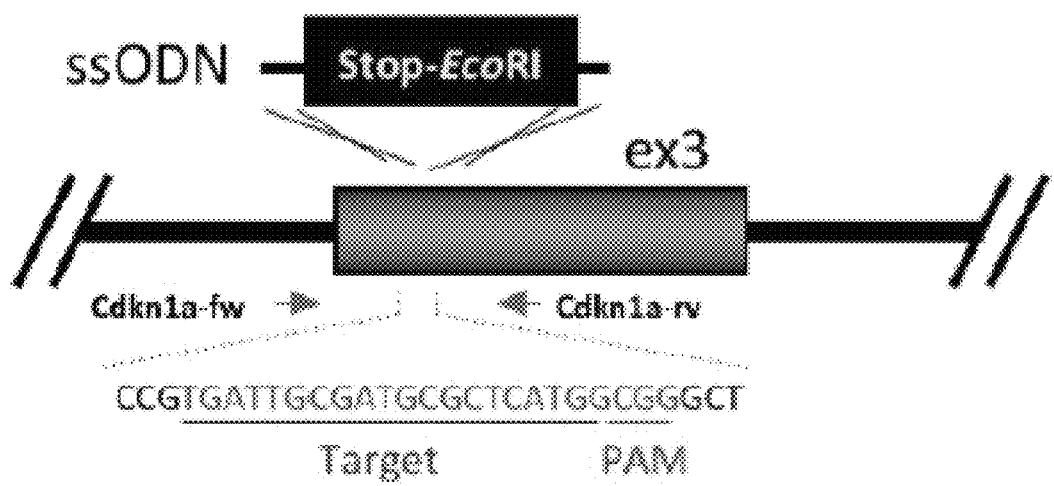

*including those containing indel mutation, complete knock-in cassette, and partical knock-in i-GONAD in Various Mouse Strains We next assessed the performance of i-GONAD in some inbred and hybrid mouse strains, and at additional loci (Table 12). i-GONAD was performed to introduce indelmutations in the Tyr gene of the C3H/HeSlc, C57BL/6NCrSlc, DBA/2CrSlc, B6D2F1/Slc, and the hybrid of the B6D2F1/Slc and C57BL/6NCrSlc strains (FIGS. 9A-9C). We also targeted indels into the Kit gene in the C3H/HeSlc and C57BL/6NCrSlc strains (FIGS. 10A-10C). We inserted small genetic changes via ssODNs into Cdkn1a and Cdkn2a of the C57BL/6NCrl strain (FIGS. 11A-11B) and Tyr in the BALB/cAJcl strain. Results showed that i-GONAD produced genome editing at all the loci tested and in all of the mice strains, except for targeting the Tyr locus in C57BL/6NCrSlc mice. This result may be due to the difficulty of obtaining pregnant females in our C57BL/6NCrSlc colony. The overall pregnancy rates in the inbred strain females were lower. Unlike the outbred strains, many animals of inbred strains, that were confirmed to be mated by the presence of vaginal plugs, did not contain implanted embryos. Taken together, these results indicate that i-GONAD can be used in many mouse strains, although its success rate is strain dependent, and further optimization may be required for certain inbred strains.

TABLE 12

| Type of genome editing | Concentration of CRISPR components | Electroporator used | No. of mice female treated | Strain | Locus | No. of pregnant mice | No. G0 pups/fetuses obtained | No. of G0 pups/fetuses with modified allele (%) | No. of G0 pups/fetuses with intended allele (%) |
|---|---|---|---|---|---|---|---|---|---|
| Knock-out | Cas9 protein (1 mg/ml) Integrated DNA Technologies(IDT) Tyr-crRNA (30 µM) FASMAC tracrRNA (30 µM) FASMAC | NEPA21 | 7 | C3H/HeSlc (inbred) | Tyr | 3 | 13 | 12 (92%) | 12 (92%) both alleles |
| Knock-out | Cas9 protein (1 mg/ml) IDT Kit-crRNA (30 µM) FASMAC tracrRNA (30 µM) FASMAC | NEPA21 | 6 | C3H/HeSlc (inbred) | Kit | 4 | 16 | 11 (69%) | 7 (44%) both alleles 4 (25%) one allele |
| Knock-out | Cas9 protein (1 mg/ml) IDT Tyr-crRNA (30 µM) FASMAC tracrRNA (30 µM) FASMAC | NEPA21 | 11 | C57BL/6NCrSlc (inbred) | Tyr | 0 | 0 | 0 (0%) | 0 (0%) |
| Knock-out | Cas9 protein (1 mg/ml) IDT Kit-crRNA (30 µM) FASMAC tracrRNA (30 µM) FASMAC | NEPA21 | 7 | C57BL/6NCrSlc (inbred) | Kit | 2 | 3 | 3 (100%) | 1 (33%) both alleles 2 (67%) one allele |
| Knock-out | Cas9 protein (1 mg/ml) IDT Tyr-crRNA (30 µM) FASMAC tracrRNA (30 µM) FASMAC | NEPA21 | 10 | DBA/2CrSlc (inbred) | Tyr | 4 | 6 | 6 (100%) | 6 (100%) both alleles |
| Knock-out | Cas9 protein (1 mg/ml) IDT Tyr-crRNA (30 µM) FASMAC tracrRNA (30 µM) FASMAC | NEPA21 | 4 | B6D2F1/Slc (hybrid) | Tyr | 4 | 23 | 20 (87%) | 19 (83%) both alleles 1 (4%) one allele |
| Knock-out | Cas9 protein (1 mg/ml) IDT Tyr-crRNA (30 µM) FASMAC tracrRNA (30 µM) FASMAC | NEPA21 | 4 | B6D2F1/Slc (female) x C57BL/6NCrSlc (male) (hybrid) | Tyr | 4 | 19 | 18 (95%) | 15 (79%) both alleles 3 (16%) one allele |
| ssODN knock-in | Cas9 protein (1 mg/ml) IDT crRNA-p21 (30 µM) IDT tracrRNA (30 µM) IDT ssODN-p21 (1 µg/µl) Eurofins Genomics | NEPA21 | 5 | C57BL/6NCrl (inbred) | Cdkn1a | 2 | 13 | 5 (38%) | 4 (31%) |
| ssODN knock-in | Cas9 protein (1 mg/ml) IDT crRNA-p16/p19 (30 µM) IDT tracrRNA (30 µM) IDT ssODN-p16/p19 (1 µg/µl) Eurofins Genomics | NEPA21 | 4 | C57BL/6NCrl (inbred) | Cdkn2a | 2 | 10 | 7 (70%) | 4 (40%) |
| ssODN knock-in | Cas9 protein (1 mg/ml) IDT crRNA-ICR-tyr (30 µM) IDT tracrRNA (30 µM) IDT ssODN-tyr (2 µg/µl) IDT | CUY21EDIT II | 4 | BALB/cAJcl (inbred) | Tyr | 2 | 6 | 3 (50%) | 1 (17%) | i-GONAD Using the AsCpf1 Nuclease

Recently, Cpf1 derived from *Acidaminococcus* sp. (AsCpf1) has been added as a genome editing tool [22, 23]. We asked whether AsCpf1 protein could be used in i-GONAD, which was performed by injecting 6.3 μM of AsCpf1 protein into the oviduct lumen of five pregnant Jcl:MCH(ICR) mice together with 30 μM of crRNA targeting the Hprt locus. A total of 40 embryos were isolated at E13.5, and the presence or absence of indels was analyzed by PCR and sequencing.

DNA from one fetus did not produce a PCR amplicon, probably due to the deletion of primer binding site(s), and DNA from 25 fetuses contained indel mutations. The results show that 65% (26/40) of the G0 offspring recovered after i-GONAD with AsCpf1 were genome-edited, and about 65% of these samples (17/26) were mosaic (Table 13).

TABLE 13

Editing of the Hprt locus using i-GONAD with AsCpf1.

| Female mice | Concentration of Cpf1/crRNA components [Electroporator used] | No. og G0 fetuses obtained | No. of G0 fetuses with mutation | No. of mosaic fetuses |
|---|---|---|---|---|
| #1 | Cpf1 protein | 2 | 2 | 2 |
| #2 | (6.3 μM) | 9 | 9 | 6 |
| #3 | Cpf1 crRNA | 6 | 4 | 1 |
| #4 | (30 μM) | 16 | 7 | 5 |
| #5 | [NEPA21] | 7 | 4 | 3 |
| total | | 40 | 26 (65%) | 17 (65%) |

Figure 12A:
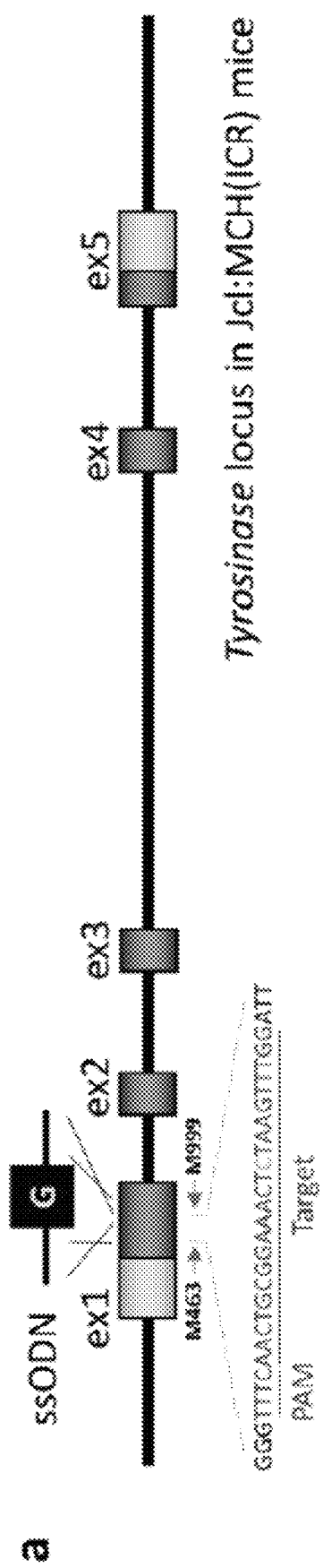
FIGS. 12A-12C show restoration of Tyr mutation of albino Jcl:MCH(ICR) mice by ssODN-based knock-in using i-GONAD with AsCpf1.
Figure 12B:
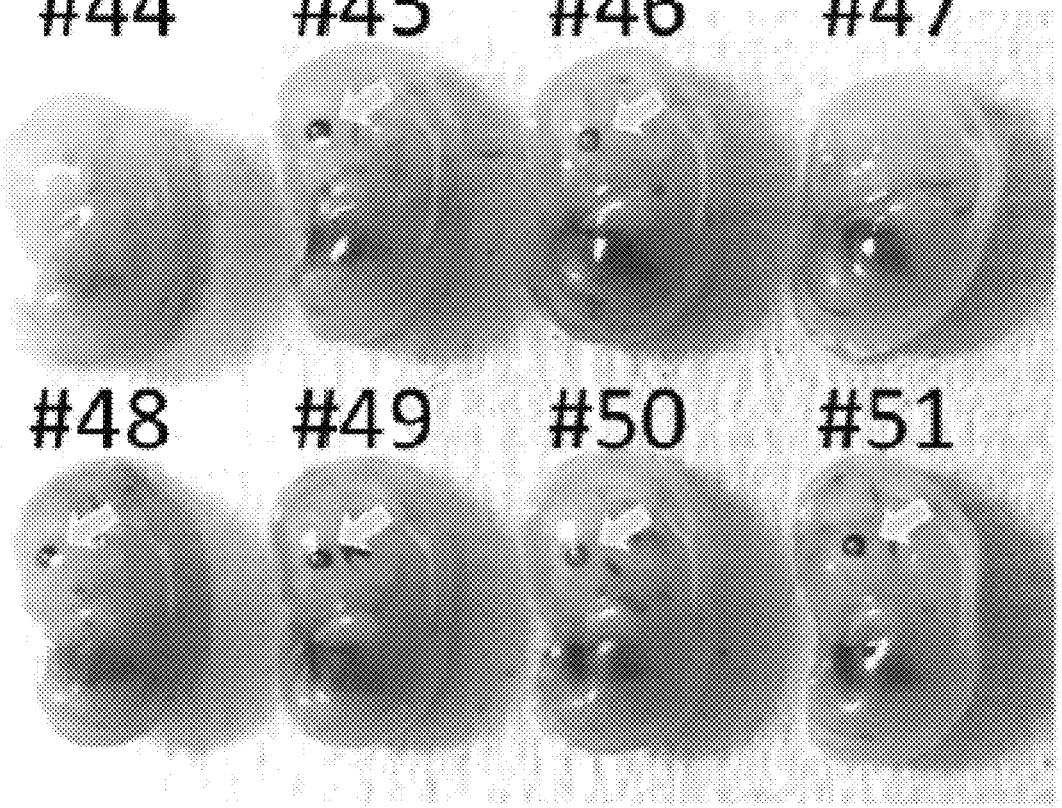
Figure 12C:
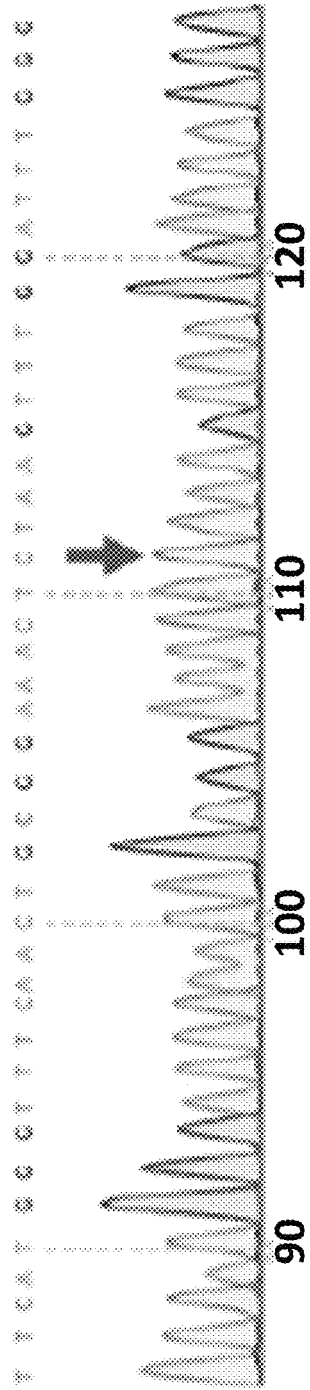
Figure 12C:
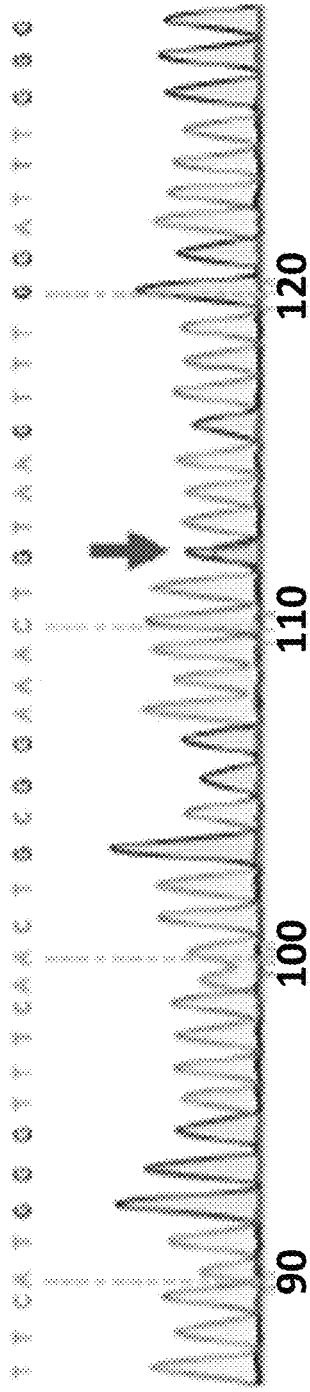
Figure 12C:
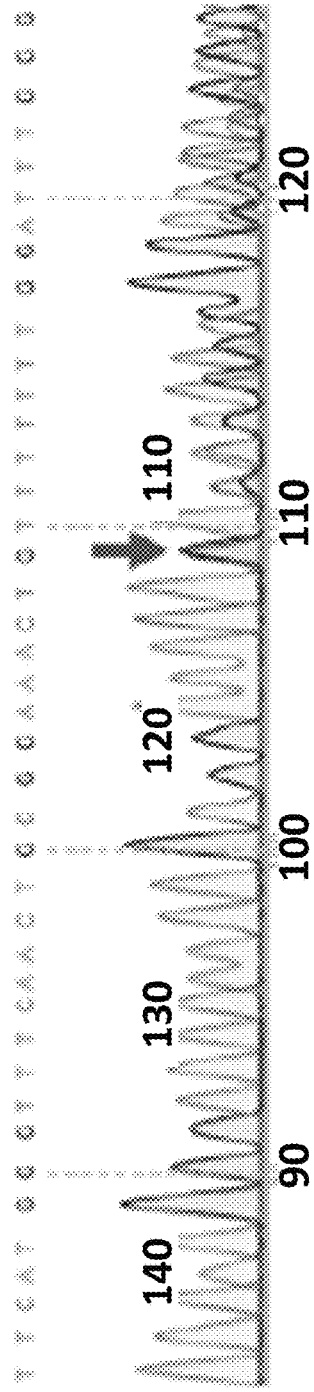

We also corrected the G308C mutation in the Tyr gene using AsCpf1. crRNA was designed for a region spanning the point mutation, and the same ssODN used in the Tyr repair experiments described for Cas9-mediated targeting was used (FIG. 12A). i-GONAD was performed on four pregnant Jcl:MCH(ICR) females. A total of 19 fetuses were harvested at E13.5. Eleven (58%) of these samples exhibited eye pigmentation indicative of repair (FIGS. 12B and Table 14, Table 15). Sequence analysis demonstrated that at least one allele had the corrected sequence (C to G) at the target site in the pigmented fetuses (FIG. 12C), and some fetuses had indel mutations. A total of 74% (14/19) of G0 fetuses were genome-edited, when gene correction and indels were combined, and the mosaicism frequency was 36% (5/14) (FIGS. 12A-12C). These studies indicate that i-GONAD can yield high efficiencies of genome editing when AsCpf1 nuclease substitutes for Cas9 (at least in two loci examined).

TABLE 14

Efficiencies of Tyr gene editing.

| No. mice treated | Electroporator used | No. G0 fetuses obtained | No. G0 mice with modified allele | No. G0 mice with repaired allele |
|---|---|---|---|---|
| 4 | CUY21EDIT II | 19 | 14 (74%) | 11 (58%) |

TABLE 15

Correction of Tyr mutation using the i-GONAD with AsCpf1.

| Female mice | Concentration of AsCpf1/crRNA components [Electroporator used] | No. of G0 fetuses obtained | No. of fetuses with modified allele | No. of fetuses with repaired allele | No. of fetuses with indel mutation | No. of mosaic fetuses |
|---|---|---|---|---|---|---|
| #1 | AsCpf1 protein | 6 | 6 | 3 | 4 | 3 |
| #2 | (6.3 μM) AsCpf1 | 5 | 2 | 2 | 0 | 0 |
| #3 | crRNA-ICR-tyr (30 μM) | 8 | 6 | 6 | 3 | 2 |
| #4 | ssODN-tyr (2 μg/μl) | 0 | 0 | 0 | 0 | 0 |
| total | [CUY21EDIT II] | 19 | 14 (74%) | 11 (58%) | 7 (37%) | 5 (36%) |

The Animals Used for i-GONAD Retain Reproductive Function

Figure 13:
FIG. 13 shows i-GONAD-used females retain reproductive capability. i-GONAD-used female mice (#3, #5, and #11 in Table 3) were mated with Jcl:MCH(ICR) males in their next cycle. Representative i-GONAD-used female mouse #3 with her litter of 9 pups.

Unlike traditional approaches to genome editing in which female embryo donors are sacrificed to isolate zygotes, the i-GONAD method does not require euthanasia of donor females. Therefore, we asked whether female mice subjected to i-GONAD retain their reproductive function. Three female mice that underwent i-GONAD and delivered genome-edited pups (mice-#3, -#5, and -#11 in Table 3) were mated naturally to fertile male mice. Two of these (67%; mice-#3 and -#11) became pregnant and successfully delivered 9 and 12 pups, respectively (FIG. 13 and Table 16). These data suggest that the oviducts in these mice retained normal function, allowing fertilization and subsequent tubal transport of fertilized eggs to uteri.

TABLE 16

Litter size of all three i-GONAD-used females.

| Female mice used for i-GONAD | No. pups delivered |
|---|---|
| #3 | 9 |
| #5 | 0 |
| #11 | 12 |

Discussion

Development of i-GONAD

We demonstrated previously a proof-of-principle genome editing method called GONAD [10]. GONAD can be performed on zygotes in situ and thus bypasses the steps of isolation of zygotes, their ex vivo handling, and their subsequent transfer to recipient females, the steps of animal genome editing that were developed and have been practiced for more than three decades. In this study, we made several improvements to the GONAD method, making it highly suitable for routine creation of genome-edited animal models. First, we assessed the optimal time of pregnancy and showed that day 0.7 is suitable for GONAD, which facilitates introduction of solution into the ampulla. Second, replacing Cas9 mRNA with Cas9 protein and replacing in vitro transcribed sgRNA with synthetic components (such as crRNA+tracrRNA) in the approach termed i-GONAD enhanced genome editing efficiency up to the levels of microinjection-based approaches. Third, i-GONAD can be used for creating large deletion, point mutation, and large cassette knock-in models. Fourth, i-GONAD works in many mouse strains. Fifth, the females used for i-GONAD retain fully functional reproductive capability. Sixth, the AsCpf1 nuclease can also be used in the i-GONAD method. Lastly, we found that i-GONAD can be performed using different types of commercially available electroporators. Because electroporators cost ten times less than microinjection setups and do not require specialized personnel, the i-GONAD method can be readily adapted by many laboratories that lack one or both.

Evaluation of Timing of the i-GONAD Procedure

GONAD performed on day 0.7 (corresponding to the late 1-cell stage) was shown to be effective for genome editing. There are several advantages to performing GONAD at this stage. First, the E0.7 zygotes are surrounded by fewer cumulus cells (FIG. 1C) and thus are more easily accessible for delivery of genome editing components (CRISPR-related nucleic acids/protein). We saw that our experiments at day 0.4 did not elicit effective delivery of components via electroporation, probably because zygotes at this stage are surrounded by a cluster of cumulus cells. Second, the oviduct on day 0.7 has a distinctly visible ampulla in many cases, which facilitates micropipette-aided introduction of solutions under a dissecting microscope. Third, in comparison to our previously reported GONAD procedure, which is conducted at day 1.5, the amount of solution introduced at day 0.7 can be reduced to 1.0-1.5 µl per oviduct, which conserves reagents [10, 24]. Fourth, we speculate that because the E0.7 zygotes are in a more compact space within the oviduct ampulla, the genome editing components may reach zygotes more effectively than at day 1.5.

Although we expected less mosaicism with GONAD at day 0.7, mosaicism was still observed, especially when Cas9 mRNA/sgRNA was used (>82%). The level of mosaicism was considerably lower (~36-65%) when ctRNP was used. Very low, or no, mosaicism could potentially be achieved by delivery of CRISPR components at even earlier stages (~5 h post-fertilization) [4]. However, performing GONAD at this stage would be quite difficult for two reasons: (1) there are challenges in experimental timing; 5 h post-fertilization is typically very early in the morning for naturally mated mice; and (2) the eggs at this early stage of pregnancy are tightly covered within the cumulus cell complex, which can prevent effective delivery of reagents to zygotes. Nevertheless, mosaicism is not necessarily a major constraint, because most of the genome-edited founders transmit targeted alleles to their offspring.

Evaluation of Different Types of CRISPR Reagents

Accumulated data from zygote injection and ex vivo electroporation-based genome editing show that RNP elicits superior genome editing efficiencies to those achieved using mRNA/sgRNA [7, 13]. In this study, we also found that RNP components directed up to ~97% genome editing efficiency, whereas the efficiencies reached using sgRNA/Cas9 mRNA components were only up to 31% (FIG. 2f). Another advantage of the RNP platform is that all components can be commercially made, which will reduce variations resulting from reagents prepared in individual labs. Commercial RNA reagents can be received in lyophilized form for RNA components, and Cas9 protein can be purchased at high concentration. These features allow preparation of electroporation mixes at any desired concentration. For GONAD, the concentration of reagents required in the electroporation mix is typically much higher than the mixes used for direct zygote injection. The fact that 100% of zygotes were genome-edited in some females indicates that the injected electroporation mix successfully surrounded all the zygotes in the oviduct at the time of electroporation.

i-GONAD and Easi-CRISPR

The knock-in efficiency of ssODN donors in the i-GONAD-treated samples was 49% (FIG. 3E). By using the same combination of locus and genetic modification, we directly compared this efficiency with the microinjection genome editing method, and the efficiency was 52% (Table 6). The number of animals needed for i-GONAD is 2.5 times less than that needed for microinjection-based approaches. One of the limitations of i-GONAD is that it requires a higher concentration of reagents than microinjection. Although our data suggest that the efficiency of i-GONAD is comparable to that of microinjection, more loci and strains must be tested to assess the comparable efficiencies of the two methods.

As discussed above, i-GONAD is a simple and convenient method for production of genome-edited animals. We optimized various parameters of the i-GONAD procedure by using the Jcl:MCH(ICR) strain (one of the most fertile mouse strains that produces large litters). We also demonstrated that genome editing by i-GONAD works in various mouse strains, although its efficiency is still strain-dependent, and recovery of fetuses/pups in some inbred strains was lower (particularly in C57BL/6), probably because of poor fertility and/or smaller litter sizes in those strains. Thus, further optimization of parameters may be required for some inbred strains. Of note, we recently generated gene-edited rats using i-GONAD (Matsuyama et al.: Successful production of genome-edited rats by the rGONAD method, in preparation; Takabayashi et al.: Successful in situ genome editing of rat preimplantation embryos using the improved genome-editing via oviductal nucleic acids delivery (i-GONAD), in preparation), which suggests that the experimental conditions described here can serve as a starting point for applying the method to other mammals.

We also successfully inserted a long ssDNA donor fragment into a target locus using i-GONAD. Long ssDNA donors were prepared using the ivTRT method as used in our highly efficient knock-in method, "Easi-CRISPR" [17, 18, 19]. Since a large amount of ssDNA is required for i-GONAD, we used spin column-based nucleic acid purification instead of gel purification, where recovery of the sample is poor. Since the microinjection approach does not require high concentrations, gel purification is typically used for zygote-microinjection experiments [17]. The column-purified ssDNA (922-925 bases) exhibited a single band after agarose gel electrophoresis, and it produced knock-in mice when used as the i-GONAD donor (FIGS. 5A-5D). Column-purified long ssDNAs can also be used as donors for creating foxed mice (i.e., mice with a gene locus flanked by loxP using Easi-CRISPR). Unlike ssODN knock-in, he efficiency of inserting a long donor fragment with the i-GONAD method was low (up to 15%) compared with microinjection (25~67%) [18]. However, i-GONAD may be superior to microinjection in terms of the number of animals used, because unlike zygote microinjection, maintenance of vasectomized males and production of pseudopregnant females are not required. Thus, i-GONAD can be used as an alternative to zygote microinjection for creating knock-in alleles.

Advantages and Applications of i-GONAD

Several groups have demonstrated that genome-edited rodents can be produced through in vitro electroporation of zygotes [4, 5, 6, 7, 8, 9]. The GONAD method goes a step beyond this, given that it directly delivers genome editing nucleic acids and CRISPR components into embryos in situ. The GONAD method offers even more advantages over in vitro electroporation-based genome editing methods. They are as follows: (1) GONAD does not require ex vivo handling of embryos; (2) it does not require in vitro cultivation of isolated embryos; (3) it does not require pseudopregnant female mice for implantation of ex vivo-treated embryos; (4) it does not require vasectomized males to produce pseudopregnant females (which is particularly advantageous in species where assisted reproductive technologies such as methods of ex vivo handling of zygotes and/or methods to prepare surrogate mothers are not well established); and (5) GONAD-treated females need not be sacrificed for zygote isolation. Another very important advantage is that the GONAD-treated females retain reproductive function and can become pregnant again after delivering pups from the GONAD procedure, suggesting that females can be re-used for a second GONAD procedure. This is a very important feature when, e.g., (1) the animals used for GONAD experiments are valuable, and (2) another genetic manipulation can be performed immediately in a newly developed genetically engineered mouse line. This avoids the laborious requirement of expanding the line to produce hundreds of zygotes for performing the second genetic change, as occurs when using microinjection or ex vivo electroporation approaches.

We show that i-GONAD can be used to rescue pigmentation defects in albino mice (Jcl:MCH(ICR) and BALB/cAJcl strains) and black mice (C57BL/6JJcl strain) by correction of a point mutation in the Tyr gene and elimination of a retrotransposon sequence in the agouti gene, respectively. Such genetic alterations are quite common in many human genetic diseases [25, 25], and our strategy can be applicable to human germline gene therapy to correct disease-causing mutations. Insertion of long sequences will also be useful in gene therapy strategies based on the addition of a functional gene [27]. Considering that human germline gene therapy will often be coupled with ex vivo handling of embryos, including an in vitro cell culture step that could cause epigenetic changes to gene expression and affect fetal development [28, 29], i-GONAD, which does not require ex vivo handling or sacrifice of GONAD-treated females, offers a highly promising approach to human germline gene therapy in the future.

Conclusions

Animal genome engineering experiments involve three major, but critical, steps: isolation of zygotes from sacrificed females, their micromanipulation ex vivo, and then transfer of the treated zygotes into another set of females. These steps have remained largely unchanged for the past four decades. Here we described a new editing method called i-GONAD and showed that popular mouse models can be routinely generated without the use of such complex and critical steps. i-GONAD offers a number of opportunities that were not possible before. First, i-GONAD does not require highly sophisticated equipment or specialized skill sets. This feature is a significant departure from traditional methods, which cannot be performed outside specialized laboratories. Even students or beginner technicians can perform i-GONAD. Second, i-GONAD uses only 40% or fewer animals than are required by conventional methods. Third, females used in currently used methods will inevitably be euthanized, whereas females used for i-GONAD can be recycled; thus, creation of genome-edited animals can occur without loss of the female. These two latter points offer significant benefits from an animal welfare point of view. Fourth, the i-GONAD method established in this study can be readily adapted for genome editing in other mammals such as the rat, other rodents, primates, and large animals. The method is particularly powerful for rare and valuable animals which cannot be sacrificed for zygote collection and/or for animals in which ex vivo handling of zygotes has not been established. Lastly, i-GONAD-treated females fully retain reproductive function; thus, the approach holds high promise as an in vivo gene therapy tool for germline gene correction.

Methods

CRISPR Reagents

CRISPR guide RNAs were designed using CRISPR.mit.edu or CHOPCHOP (Table 17). The sgRNA for Foxe3 was synthesized as described previously [10] using the primer sets (M1055/M939) and the pUC57-sgRNA vector as a template (Addgene plasmid number: #51132). The mRNAs for eGFP and Cas9 were in vitro transcribed as previously described [10, 24]. The synthetic crRNA and tracrRNA were commercially obtained as Alt-R™ CRISPR guide RNAs from Integrated DNA Technologies (IDT), Skokie, Ill., USA or purchased from FASMAC, Kanagawa, Japan together with Cas9 protein (Alt-R™ S.p. CAS9 Nuclease 3NLS). The ssODN donors were custom synthesized from IDT (Ultramer: for Tyr rescue experiment [Tyr-rescue] and agouti rescue experiment [agouti-rescue]) or synthesized from Eurofins Genomics, Louisville, Ky., USA (for ssODN knock-in into the Cdkn1a and Cdkn1a genes). Long ssDNA donors (for Pitx3 and Tis21 reporters) were prepared from the double-stranded DNA (dsDNA) templates using the ivTRT method described previously [17] with slight modifications. The T2A-mCitrine cassette was amplified from the original vector (pP200) with primer sets (M1051/M1052 for Pitx3 and M1053/M1054 for Tis21) and inserted into the SmaI site of pUC119, resulting in pP206 (for Pitx3) and pP209 (for Tis21). The templates for RNA synthesis were amplified from these vectors with primer sets (PP226/M272 for Pitx3 and PP227/M272 for Tis21), and RNAs were synthesized using the T7 RiboMax Express Large Scale RNA Production System (Promega, Madison, Wis., USA). The RNAs were purified using a MEGAclear Kit (Ambion), and the cDNAs were generated using SuperScript III Reverse Transcriptase (for Pitx3) or SuperScript IV Reverse Transcriptase (for Tis21; Life Technologies) with the primers PP226 for Pitx3 and PP227 for Tis21. The final step of gel extraction, as done for purifying cDNA for microinjection, was excluded in order to obtain a sufficiently higher concentration of the final ssDNA. Instead, spin column-based nucleic acid purification using NucleoSpin Gel and PCR Clean-up (Macherey-Nagel, Duren, Germany) was performed. After ethanol precipitation, the DNA pellet was dissolved in EmbryoMax Injection Buffer (Millipore). The sequences for primers and ssODNs are shown in Table 18.

TABLE 17

CRISPR target sequences and the types of gRNA used.

| Target loci | Target seqs (5'-3') PAM | Types of gRNA used |
|---|---|---|
| Foxe3 | GAGACAGCCGGGCTTCGCGCCGG | crRNA/tracrRNA or sgRNA |
| Tyr (ICR) | GGAAACTCTAAGTTTGGATTTGG | crRNA/tracrRNA |
| Agouti (1) | AATGGACATTTAGTCGAACTGGG | crRNA/tracrRNA |
| Agouti (2) | AGGGTTTAACCACCTATCGAAGG | crRNA/tracrRNA |
| Pitx3 | CGGTGTGAGCCGCAGGTCTGTGG | crRNA/tracrRNA |
| Tis21 | GGCTCCTATCTAGCTGGAGACGG | crRNA/tracrRNA |
| Tyr (wild) | AACTTCATGGGTTTCAACTGCGG | crRNA/tracrRNA |
| Kit | CTGTTCACGCCGCTGCTCATTGG | crRNA/tracrRNA |
| p21 (Cdkn1a) | TGATTGCGATGCGCTCATGGCGG | crRNA/tracrRNA |
| p16/p19 (Cdkn2a) | CGGTGCAGATTCGAACTGCGAGG | crRNA/tracrRNA |

*Sequences in Table 17 are SEQ ID NOS: 21-30, respectively.

TABLE 18

Sequences of the oligonucleotides used in this study.

| Name of oligos | Sequences (5'-3') |
|---|---|
| Tyr-rescue* | TGTTTTATAATAGGACCTGCCAGTGCTCAGGCAACTTCATGGGTTTCAACTGCGGAAACTGTAAGTTTGGATTTGGGGGCCCAAATTGTACAGAGAAGCGAGTCTTGATTAGAAGAAACATTTTTGATTTG |
| agouti-rescue* | TTTATTGCAACCTGCCTTTGCCTTTATATGTGTTGAATATTTTTAGACTTGATACCCAGTGAATTCGAAGGGTTTTCCCAAACCCCTCCTCAGAACTCAGGAGTATCATTAAGGTACTGCGGTTT |
| M1035 | TCCTCCCCCTATGTATACCG |
| M1036 | TCCCTGTTCCTGGCCTTAG |
| M1037 | CCTGTGGGTTGATCCCTATG |
| M1038 | CAAACACTGGCTCACAGATG |
| M1051 | GTAATACGACTCACTATAGGGCCCGGGCCGCCGCCGGCCGCTAACCTTAGCCCCTGCCAGTACGCCGTGGAACGGCCGGTGGGCAGTGGAGAGGGCAGAG |
| M1052 | CATGAATTCAAGCCAGTCTAGGCGACCCCTGTCCGGAGAGGCTGTGAATTACTGCCCCGCCCTCGGGGATGGATCCACAGACCTGCGGCTCACTTGTACAGCTCGTCCATGCC |
| M1053 | GTAATACGACTCACTATAGGGCAAGAACCAGATGATGCTGGGCAGGAGCAGCCCCTCGAAGAACTATGTGATGGCCGTCTCCAGCGGCAGTGGAGAGGGCAGAG |
| M1054 | CATGAATTCTATACGGTGGCCTGTTGTCAGGGCAGCATGAGAACAGTAGAGTGCCAGGGTCGGGTGGCTCCTATCTACTTGTACAGCTCGTCCATGCC |
| M1055 | TAATACGACTCACTATAGGGAGACAGCCGGGCTTCGCGCGTTTTAGAGCTAGAAATAGCAAG |
| M272 | CAGGAAACAGCTATGACC |
| M389 | TCGCCACCATGGTGAGCAAGGGCGAG |
| M390 | CTCTAGACTTACTTGTACAGCTCGTCCAT |
| M463 | TCCTTCTGTCCAGTGCACCAT |
| M939 | AAAAAAAGCACCGACTCGG |
| M943 | AGGATCTGTGTTCAACCCATT |
| M944 | ACAAAGAAAACCAAGCGTGAC |
| M947 | CTTGAGAAAGGCCACAGTTTC |
| M948 | ACGAACCTCTTCATCTGCTGT |

TABLE 18-continued

Sequences of the oligonucleotides used in this study.

| Name of oligos | Sequences (5'-3') |
|---|---|
| M992 | CCTGGACAGCCTGTTGGG |
| M993 | TTCAGTCTGGTGGTGAGACAG |
| M999 | ATGGGTGTTGACCCATTGTT |
| PP226 | CAAGCCAGTCTAGGCGACCC |
| PP227 | CATGAATTCTATACGGTGGCC |
| Mm HPRTF15 | AGGTTTCGAGCCCTGATATTCG |
| Mm HPRTR15 | ATGTGGCAAGGTCAAAAACAGT |
| Tyr-F | TCTCTGATGGCCATTTTCCTC |
| Tyr-R | AACATGGGTGTTGACCCATT |
| Kit-F | GAGGGAAATGGTTTAGTTTGGG |
| Kit-R | GGGTTTCTGGAGGAGAAAGG |
| Cdkn1a-fw | CCTGAAGACTGTGATGGGGTA |
| Cdkn1a-rv | TCTCCGTGACGAAGTCAAAGT |
| Cdkn2a-fw | GCCGTGATCCCTCTACTTTTT |
| Cdkn2a-rv | TATCGCACGATGTCTTGATGT |
| Sry-F2 | AAGCGACCATGAATGCATTCATGGTGTGGT |
| Sry-R2 | GAGGTCGATACTTATAGTTCGGGTATTTCTCTCTGTG |

*Regions of homology are underlined. Sequences in Table 18 are SEQ ID NOS: 31-67, respectively.

Animals

Mice were maintained at the animal facility in Tokai University School of Medicine, Hamamatsu University School of Medicine, or Shigei Medical Research Institute. Adult Jcl:MCH(ICR) (hybrid strain originally derived from Jcl:ICR strain: www.clea-japan.com/en/animals/animal_g/g_01.html), C57BL/6JJcl (inbred strain), and BALB/cAJcl (inbred strain) mice were obtained from CLEA Japan, Inc. (Tokyo, Japan); C3H/HeSlc (inbred strain), C57BL/6NCrSlc (inbred strain), DBA/2CrSlc (inbred strain), and B6D2F1/Slc (hybrid strain) mice were obtained from Japan SLC, Inc. (Shizuoka, Japan); and C57BL/6NCrbl (inbred strain) mice were obtained from Charles River Laboratories Japan, Inc. (Yokohama, Japan). All the animal experiments were performed in accordance with institutional guidelines and were approved by the Institutional Animal Care and Use Committee (Permit Numbers #154014, #165009, #171003 at Tokai University, #2017062 at Hamamatsu University, and #17008 at Shigei Medical Research Institute).

Preparation of CRISPR Electroporation Solutions

The solution contained in vitro synthesized sgRNAs (or commercially procured crRNA/tracrRNA mixes) and the commercially procured Cas9 protein. When the donor DNAs were included in the electropoartion solutions, they were either commercially synthesized ssODNs or ivTRT synthesized long ssDNAs. The Cas9 mRNA/sgRNA mixture was prepared as we previously described [10]. We used 0.05% of trypan blue (Nacalai Tesque Inc., Kyoto, Japan) as a marker for successful injection, only when eGFP mRNA was used or Cas9 was supplied as mRNA. Lyophilized ssODNs were re-suspended in nuclease-free water to a concentration of 10 µg/µl. Lyophilized crRNA and tracrRNA were first re-suspended in RNase-free Duplex Buffer to a concentration of 200 µM. Equal volumes of crRNA and tracrRNA were combined in a 1.5-ml tube, heated in a thermocycler to 94° C. for 2 min, and then placed at room temperature for about 10 min. The annealed crRNA and tracrRNA were mixed with Cas9 protein and/or ssODN/ssDNA so that the final concentrations of components were 30 µM (for crRNA/tracrRNA), 1 mg/ml (for Cas9 protein), 1 or 2 µg/µl (for ssODN), and 0.85~1.4 µg/µl (for ssDNA). AsCpf1 crRNA (MmHPRT-273-S: 5'-GTGCCCTCTTCTGGCCTGCCA-3') (SEQ ID NO: 69) was a kind gift from IDT. Lyophilized crRNAs were first re-suspended in RNase-free water to a concentration of 100 µM and then heated in a thermocycler to 95° C. for 5 min and placed at room temperature for about 10 min. AsCpf1 protein (IDT) was mixed with crRNA so that the final concentrations of components were 30 µM (for crRNA) and 6.3 µM (for AsCpf1 protein). The electroporation solution was occasionally diluted using Opti-MEM (Thermo Fisher Scientific) to adjust the volume to 1.5 µl/oviduct.

GONAD Procedure

The females used for the procedure were not super-ovulated except for the C57BL/6JJcl strain. For all of the strains except C57BL/6JJcl, females in estrus were mated with stud males. Matings were set up at 16:00-17:00, and copulation plugs were confirmed by visual inspection the next morning (9:00-10:00). We designated day 0 of gestation at 0:00 (midnight) according to *Manipulating the Mouse Embryo: A Laboratory Manual* [30], and the females with plugs were designated as day 0.4 of gestation at 10:00 and day 0.7 of gestation at 16:00, at which time they were used for the electroporation experiments.

Surgical procedures were performed on anesthetized females at day 0.7 of pregnancy (corresponding to late 1-cell stage zygotes, at 16:00 of the same day when the plugs were confirmed) under observation using a dissecting microscope (SZ11; Olympus, Tokyo, Japan), as described previously [10, 24] with slight modifications. The ovary/oviduct/uterus was exposed after making an incision at the dorsal skin. Approximately 1.0-1.5 µl of electroporation solution (pre-warmed at 37° C. for 10 min) was injected into the oviduct lumen from upstream of the ampulla using a micropipette. The micropipette apparatus consisted of a glass capillary needle (pulled using a P-97/IVF electric puller; Sutter Instrument Co., Novato, Calif., USA) and a mouthpiece attached to the needle. Immediately after the injection of solution, the oviduct regions were covered with a piece of wet paper (Kimwipe; Jujo-Kimberly Co. Ltd., Tokyo, Japan) soaked in phosphate-buffered saline (PBS) and then grasped in tweezer-type electrodes (CUY652-3 [NEPA GENE Co. Ltd., Ichikawa, Chiba, Japan] for T820 and NEPA21, and LF650P3 [BEX Co. Ltd., Tokyo, Japan] for CUY21EDIT II). The electroporation was performed using a square-wave pulse generator T820 (BTX Genetronics Inc.), or NEPA21 (NEPA GENE), or CUY21EDIT II (BEX). The electroporation parameters were as follows: eight square-wave pulses with a pulse duration of 5 ms, a pulse interval of 1 s, and an electric field intensity of 50 V for T820; poring pulse: 50 V, 5-ms pulse, 50-ms pulse interval, 3 pulse, 10% decay (±pulse orientation) and transfer pulse: 10 V, 50-ms pulse, 50-ms pulse interval, 3 pulse, 40% decay (±pulse orientation) for NEPA21; and square (mA), (+/−), Pd V: 60 V or 80 V, Pd A: 200 mA, Pd on: 5.00 ms, Pd off: 50 ms, Pd N: 3, Decay: 10%, DecayType: Log for CUY21EDIT II. After the electroporation, the oviducts were returned to their original position, and the incisions were sutured. The animals were monitored for anesthesia recovery and were housed for further analysis.

Microinjection

CRISPR components were mixed in EmbryoMax Injection Buffer. The final concentrations of Cas9 protein, crRNA/tracrRNA, and ssODN (for Tyr rescue) were 50 ng/µl, 0.61 µM, and 10 ng/µl, respectively. Unfertilized oocytes isolated from super-ovulated female mice (Jcl:MCH (ICR)) were subjected to in vitro fertilization (IVF) with spermatozoa freshly isolated from a Jcl:MCH(ICR) male mouse. Microinjection of the mixture was performed into pronuclei of in vitro fertilized eggs. The injected embryos were transferred into the oviduct of pseudopregnant Jcl:MCH(ICR) females to allow further development. The resulting fetuses (day 13.5 or 15.5) were recovered and subjected to genotyping analysis.

Observation of mCitrine Fluorescence

The fetuses recovered were observed using a fluorescence stereomicroscope with filter for GFP (Olympus SZX7 with SZX-MGFPA) for detecting the mCitrine fluorescence.

Analysis of CRISPR/Cas9-Induced Mutations and Insertions

Genomic DNAs were isolated from the limb of mid-gestational fetuses or the ear-piece of live mice using All-In-One Mouse Tail Lysis Buffer (ABP-PP-MT01500; Kurabo, Osaka, Japan) through incubation at 55° C. for 3 h or overnight and subsequent inactivation at 85° C. for 45 min. The PCR for amplification of target loci Foxe3, Tyr, agouti, and Hprt was performed in a total of 10 µl solution containing 5 µl of 2× GC buffer I, 0.2 mM deoxynucleotide (dNTP), 1 µl of the crude lysate, the primer pairs (Table 18), and 0.125 U of TaKaRa r-Taq (TaKaRa) using denaturation (95° C. for 5 min), 35 cycles of 95° C. for 45 s, 58° C. for 30 s, and 72° C. for 1 min, and extension (72° C. for 5 min). For amplification of target loci Pitx3 and Tis21, PCR amplifications were performed using PrimeSTAR HS DNA Polymerase (TaKaRa) in a total of 10 µl solution containing 2 µl of 5× PrimeSTAR buffer I, 0.2 mM dNTP, 1 µl of the crude lysate, the primer pairs (Additional file 1: Table S9), and 0.25 U of PrimeSTAR HS DNA Polymerase using denaturation (94° C. for 3 min), 35 cycles of 98° C. for 10 s, 62° C. or 64° C. for 5 s, and 72° C. for 2 min, and extension (72° C. for 10 min). Direct sequencing was performed using the PCR products and the primers listed in Table 18.

Mosaicism of alleles was assessed by observing an electropherogram of Sanger sequence results. Mosaicism was assessed based on the following criteria: (1) the presence of multiple peaks consisting of more than three peaks (or two peaks in the Hprt gene of male mice) and (2) one of the two overlapping peaks apparently lower or higher than the other. Determination of gender was performed with PCR using primer set Sry-F2 and Sry-R2 (Table 18)[31].

REFERENCES

1. Harms D W, Quadros R M, Seruggia D, Ohtsuka M, Takahashi G, Montoliu L, et al. Mouse genome editing using the CRISPR/Cas system. Curr Protoc Hum Genet. 2014; 83: 15.7.1-15.7.27.
2. Wang H, Yang H, Shivalila C S, Dawlaty M M, Cheng A W, Zhang F, et al. One-step generation of mice carrying mutations in multiple genes by CRISPR/Cas-mediated genome engineering. Cell. 2013; 153: 910-8.
3. Gurumurthy C B, Grati M, Ohtsuka M, Schilit S L P, Quadros R M, Liu X Z. CRISPR: a versatile tool for both forward and reverse genetics research. Hum Genet. 2016; 135: 971-6.
4. Hashimoto M, Yamashita Y, Takemoto T. Electroporation of Cas9 protein/sgRNA into early pronuclear zygotes generates non-mosaic mutants in the mouse. Dev Biol. 2016; 418: 1-9.
5. Kaneko T, Mashimo T. Simple genome editing of rodent intact embryos by electroporation. PLoS One. 2015; 10: e0142755.
6. Kaneko T, Sakuma T, Yamamoto T, Mashimo T. Simple knockout by electroporation of engineered endonucleases into intact rat embryos. Sci Rep. 2014; 4: 6382.
7. Chen S, Lee B, Lee A Y F, Modzelewski A J, He L. Highly efficient mouse genome editing by CRISPR ribonucleoprotein electroporation of zygotes. J Biol Chem. 2016; 291: 14457-67.
8. Hashimoto M, Takemoto T. Electroporation enables the efficient mRNA delivery into the mouse zygotes and facilitates CRISPR/Cas9-based genome editing. Sci Rep. 2015; 5: 11315.

9. Qin W, Dion S L, Kutny P M, Zhang Y, Cheng A W, Jillette N L, et al. Efficient CRISPR/Cas9-mediated genome editing in mice by zygote electroporation of nuclease. Genetics. 2015; 200: 423-30.
10. Takahashi G, Gurumurthy C B, Wada K, Miura H, Sato M, Ohtsuka M. GONAD: Genome-editing via Oviductal Nucleic Acids Delivery system: a novel microinjection independent genome engineering method in mice. Sci Rep. 2015; 5: 11406.
11. Wada K, Maeda Y Y, Watanabe K, Oshio T, Ueda T, Takahashi G, et al. A deletion in a cis element of Foxe3 causes cataracts and microphthalmia in rct mice. Mamm Genome. 2011; 22: 693-702.
12. Medina-Martinez O, Brownell I, Amaya-Manzanares F, Hu Q, Behringer R R, Jamrich M. Severe defects in proliferation and differentiation of lens cells in Foxe3 null mice. Mol Cell Biol. 2005; 25: 8854-63.
13. Aida T, Chiyo K, Usami T, Ishikubo H, Imahashi R, Wada Y, et al. Cloning-free CRISPR/Cas system facilitates functional cassette knock-in in mice. Genome Biol. 2015; 16: 87.
14. Jacobi A M, Rettig G R, Turk R, Collingwood M A, Zeiner S A, Quadros R M, et al. Simplified CRISPR tools for efficient genome editing and streamlined protocols for their delivery into mammalian cells and mouse zygotes. Methods. 2017; 121-2: 16-28.
15. Yokoyama T, Silversides D W, Waymire K G, Kwon B S, Takeuchi T, Overbeek P A. Conserved cysteine to serine mutation in tyrosinase is responsible for the classical albino mutation in laboratory mice. Nucleic Acids Res. 1990; 18: 7293-8.
16. Pettitt S J, Liang Q, Rairdan X Y, Moran J L, Prosser H M, Beier D R, et al. Agouti C57BL/6N embryonic stem cells for mouse genetic resources. Nat Methods. 2009; 6: 493-5.
17. Miura H, Gurumurthy C B, Sato T, Sato M, Ohtsuka M. CRISPR/Cas9-based generation of knockdown mice by intronic insertion of artificial microRNA using longer single-stranded DNA. Sci Rep. 2015; 5: 12799.
18. Quadros R M, Miura H, Harms D W, Akatsuka H, Sato T, Aida T, et al. Easi-CRISPR: a robust method for one-step generation of mice carrying conditional and insertion alleles using long ssDNA donors and CRISPR ribonucleoproteins. Genome Biol. 2017; 18: 92.
19. Miura H, Quadros R M, Gurumurthy C B, Ohtsuka M. Easi-CRISPR for creating knock-in and conditional knockout mouse models using long ssDNA donors. Nat Protoc. 2018; 13: 195-215.
20. Grealish S, Jonsson M E, Li M, Kirik D, Bjorklund A, Thompson L H. The A9 dopamine neuron component in grafts of ventral mesencephalon is an important determinant for recovery of motor function in a rat model of Parkinson's disease. Brain. 2010; 133: 482-95
21. Haubensak W, Attardo A, Denk W, Huttner W B. Neurons arise in the basal neuroepithelium of the early mammalian telencephalon: a major site of neurogenesis. Proc Natl Acad Sci. 2004; 101: 3196-201.
22. Zetsche B, Gootenberg J S, Abudayyeh O O, Slaymaker I M, Makarova K S, Essletzbichler P, et al. Cpf1 is a single RNA-guided endonuclease of a class 2 CRISPR-Cas system. Cell. 2015; 163: 759-71.
23. Hur J K, Kim K, Been K W, Baek G, Ye S, Hur J W, et al. Targeted mutagenesis in mice by electroporation of Cpf1 ribonucleoproteins. Nat Biotechnol. 2016; 34: 807-8.
24. Gurumurthy C B, Takahashi G, Wada K, Miura H, Sato M, Ohtsuka M. GONAD: a novel CRISPR/Cas9 genome editing method that does not require ex vivo handling of embryos. Curr Protoc Hum Genet 2016; 88: 15.8.1-15.8.12.
25. Hancks D C, Kazazian H H, Koning A, Gu W, Castoe T, Batzer M, et al. Roles for retrotransposon insertions in human disease. Mob DNA. 2016; 7: 9.
26. Yu H, Zhang V W. Precision medicine for continuing phenotype expansion of Human Genetic diseases. Biomed Res Int. 2015; 2015: 745043.
27. Abe H, Kamimura K, Kobayashi Y, Ohtsuka M, Miura H, Ohashi R, et al. Effective prevention of liver fibrosis by liver-targeted hydrodynamic gene delivery of matrix metalloproteinase-13 in a rat liver fibrosis model. Mol Ther Nucleic Acids. 2016; 5: e276.
28. Khosla S, Dean W, Reik W, Feil R. Culture of preimplantation embryos and its long-term effects on gene expression and phenotype. Hum Reprod Update. 2001; 7: 419-27.
29. Dumoulin J C, Land J A, Van Montfoort A P, Nelissen E C, Coonen E, Derhaag J G, et al. Effect of in vitro culture of human embryos on birthweight of newborns. Hum Reprod 2010; 25: 605-612.
30. Behringer R, Gertsenstein M, Nagy K V, Nagy A. Manipulating the mouse embryo: a laboratory manual. 4th ed. Cold Spring Harbor Laboratory Press: Cold Spring Harbor; 2014.
31. Kageyama S, Moriyasu S, Tabata T, Chikuni K. Amplification and sequence analysis of SRY (sex-determining region Y) conserved region of domestic animals using polymerase chain reaction. Anim Sci Technol. 1992; 63: 1059-65.

Example 2—Essential Role of Acrosin in Fertilization: Reinvestigation Using Gene-Knockout Hamsters Abstract During natural fertilization, mammalian spermatozoa must pass through the zona pellucida before reaching the plasma membrane of the oocyte. It is assumed that this step involves partial lysis of the zona by sperm acrosomal enzyme(s), but there has been no unequivocal evidence to support this view. Here we present evidence that acrosin, an acrosomal serine protease, plays an essential role in sperm penetration of the zona. We generated acrosin-knockout (KO) hamsters using an in vivo transfection CRISPR/Cas9 system. Homozygous mutant males were completely sterile. Acrosin-KO spermatozoa ascended the female genital tract and reached ovulated oocytes in the oviduct ampulla, but never fertilized them. In vitro fertilization (IVF) experiments revealed that mutant spermatozoa attached to the zona, but failed to penetrate it. When the zona pellucida was removed prior to IVF, all oocytes were fertilized. This indicates that in hamsters, acrosin plays an indispensable role in allowing fertilizing spermatozoa to penetrate the zona. This study also suggests that the KO hamster system would be a useful model for identifying new gene functions or analyzing human and animal disorders because of its technical facility and reproducibility.

Significance

Mammalian oocytes are surrounded by the zona pellucida, a glycoprotein coat that protects the oocyte and embryo from mechanical damage during their preimplantation development within the oviduct. Fertilizing spermatozoa must penetrate the zona, but we do not know the exact mechanisms underlying this process. Sperm proteases were thought to work as zona lysins, but gene-knockout studies in mice did not support this assumption. In this study, we generated hamsters without acrosin, the major acrosomal protease, to examine its role in in vivo and in vitro fertilization. Surprisingly, mutant male hamsters were completely infertile because their spermatozoa were unable to penetrate the zona. We thus demonstrated that, at least in hamsters, acrosin is essential for sperm penetration through the zona.

Introduction

Mammalian spermatozoa deposited in the vagina or uterus ascend the female genital tract and penetrate the outer layers of the oocyte (cumulus oophorus and zona pellucida) before reaching its plasma membrane. It is generally assumed that spermatozoa penetrate the zona by mechanical force, aided by the acrosomal enzymes that are bound to the inner acrosomal membrane (1). A biophysical analysis suggested that the calculated force generated by the sperm alone is not sufficient to penetrate the zona mechanically (2). Of the many acrosomal enzymes, acrosin has been thought to be a major player in this process, because of its strong hydrolyzing activity and widespread distribution in mammals (3, 4). Indeed, it was reported that anti-acrosin antibodies significantly decreased the incidence of in vivo fertilization in rabbits (5), and inhibition of acrosin by soybean trypsin inhibitor prevented human spermatozoa from penetrating the zona (6). However, in contrast to these findings, acrosin-deficient mouse spermatozoa could pass through the zona, although dispersion of the cumulus oophorus was delayed to some extent (7). It is possible that mouse spermatozoa are exceptional in that they do not rely on acrosomal enzymes to penetrate the zona, because sperm acrosin activity is weaker in mice compared with that in other mammalian species such as rats and hamsters (8). The recent advent of gene-editing technology has enabled the generation of knockout (KO) rats (9), and although Isotani et al. successfully disrupted the acrosin gene in rats, acrosin-KO rat spermatozoa were able to penetrate the zona and fertilize oocytes (10). Thus, there has been no conclusive evidence for the involvement of acrosomal enzyme(s) in mammalian sperm penetration through the zona.

The golden hamster (*Mesocricetus auratus*) is a small rodent that has been extensively used in biomedical research in fields including oncology, immunology, metabolic disease, cardiovascular disease, infectious disease, physiology, and behavioral and reproductive biology (11). Unlike laboratory mice and rats, which belong to the Muridae family of rodents, hamsters belong to the Cricetidae family. Hamsters have many advantages as a laboratory species, including small body size (between mice and rats), short gestation period (16 days), large litter size (5-10 pups), and a very stable four-day estrous cycle (12). Indeed, the golden hamster is the species in which in vitro fertilization (IVF) using epididymal spermatozoa was first reported (13). The large acrosome of hamster spermatozoa enables researchers to observe the acrosomal reaction in live spermatozoa under a phase-contrast microscope (14, 15). However, hamster embryos are highly vulnerable to in vitro conditions, which has hindered the generation of gene-modified hamsters (16). To circumvent this obstacle, we employed a recently developed in vivo gene-editing system (improved genome-editing via oviductal nucleic acids delivery system; i-GONAD) (17) to generate gene-KO hamsters. This enabled us to bypass all the in vitro embryo-handling steps, thus making generation of KO hamsters technically easier and highly reproducible. The present study aimed to determine whether acrosin is essential for sperm penetration through the zona by investigating how acrosin-KO hamster spermatozoa behaved both in vivo and in vitro.

Results

Generation of Acrosin-Deficient Hamsters

Figure 14:
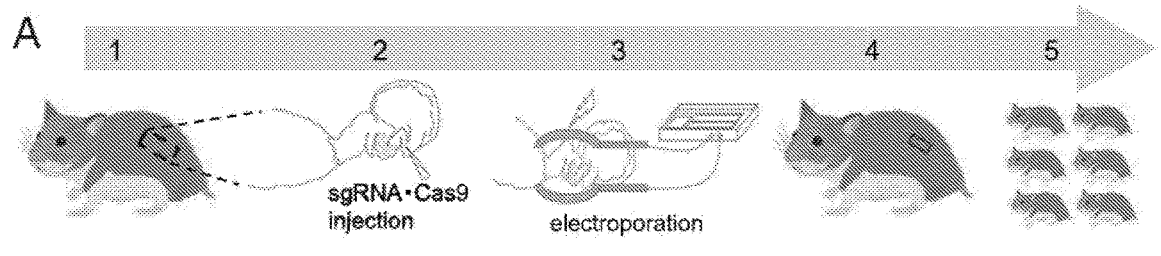
FIG. 14. Generation of acrosin-KO hamsters and biochemical analyses of spermatozoa. (A) Generation of KO hamsters by the GONAD method. After the solution containing sgRNAs and Cas9 protein was injected into the exposed oviducts containing zygotes (Step 1-2), electric pulses for in vivo transfection into zygotes were applied to the oviducts using a forceps-like electrode (Step 3). After surgery, the females were allowed to deliver young (Step 4-5). (B) The position of sgRNAs and Cas9 injection. These were injected from the upper segment of the ampulla (one of two arrows) toward the lower segments where oocytes reside. (C) The mutant alleles found in four founders. Six mutant alleles were identified. For more information on the WT sequence, FIG. 18. (D) Western blot of sperm acid extracts from WT and acrosin-KO hamsters using affinity-purified antibody against the N-terminal 20 amino acids of mouse proacrosin. Acrosin-KO hamster spermatozoa completely lacked the 47- and 40-kDa forms of (pro)acrosin. (E) Gelatin zymography of sperm acid extracts. After SDS-PAGE in the presence of 0.1% gelatin, the gels were washed with 2.5% Triton X-100, incubated at pH 8.0 at 37° C., and then stained with Coomassie brilliant blue. Gelatin-hydrolyzing proteins were detected as transparent bands against a blue background. Note that KO spermatozoa are completely devoid of gelatin-hydrolyzing proteins, whereas 47- and 40-kDa (pro)acrosins in WT spermatozoa exhibit the enzyme activity. (F) Acrosin activity in sperm acid extracts. Proteolytic activity of acrosin-KO sperm was measured using Boc-Phe-Ser-Arg-MCA (FSR), Boc-Leu-Thr-Arg-MCA (LTR), and Boc-Val-Pro-Arg-MCA (VPR) as substrates. Data are expressed as the mean±standard error of the mean; n=3. (G) Fertility test of acrosin-KO males. No homozygous acrosin-KO males from either of two lines carrying different mutant alleles produced offspring after mating with WT females. All WT males were confirmed to be fertile. (II) A cumulus-oocyte complex retrieved from the oviduct of a female that had been mated with an acrosin-KO male. A spermatozoon had reached the zona of an oocyte (arrow) but had not penetrated it. Bar, 20 μm.
Figure 14:
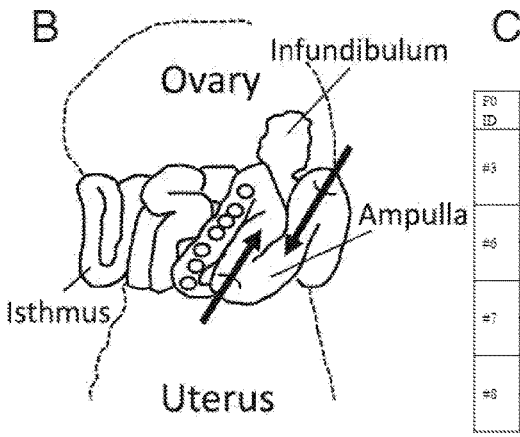
Figure 14:
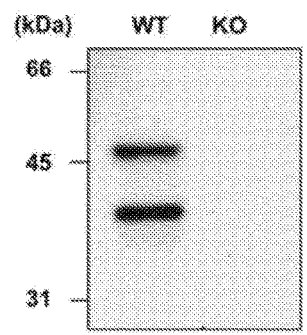
Figure 14:
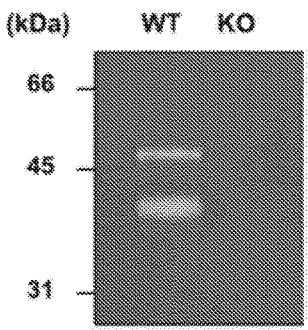
Figure 14:
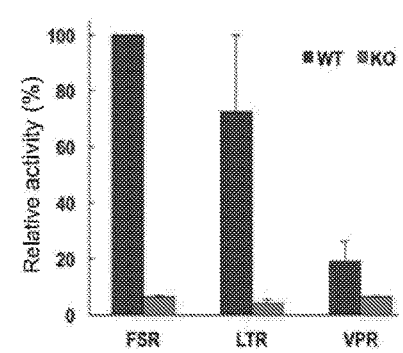
Figure 14:
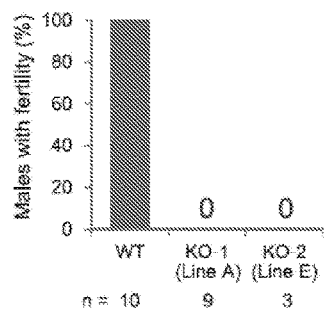
Figure 14:
Figure 18:
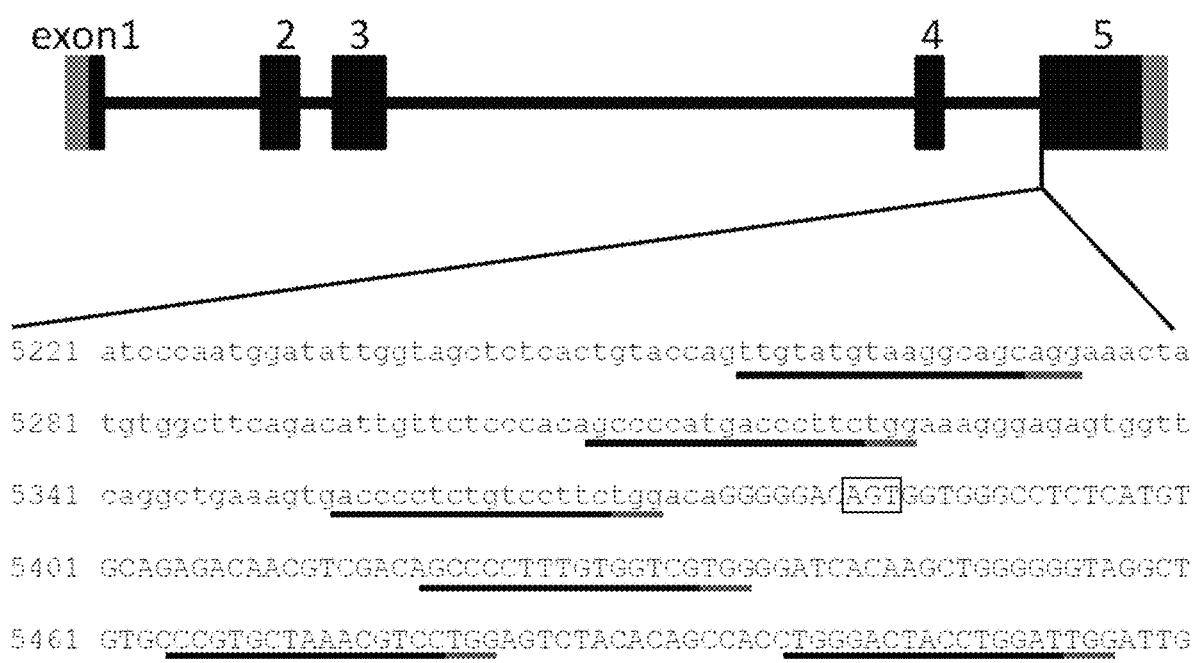
FIG. 18. The structure of the hamster acrosin gene and the positions of sgRNAs. We designed six sgRNAs for knockout of the acrosin gene. The sgRNA target sequences and protospacer adjacent motif (PAM) sequences are highlighted by black and grey lines, respectively. The square indicates the sequence coding for serine, the active center of acrosin.
Figure 19:
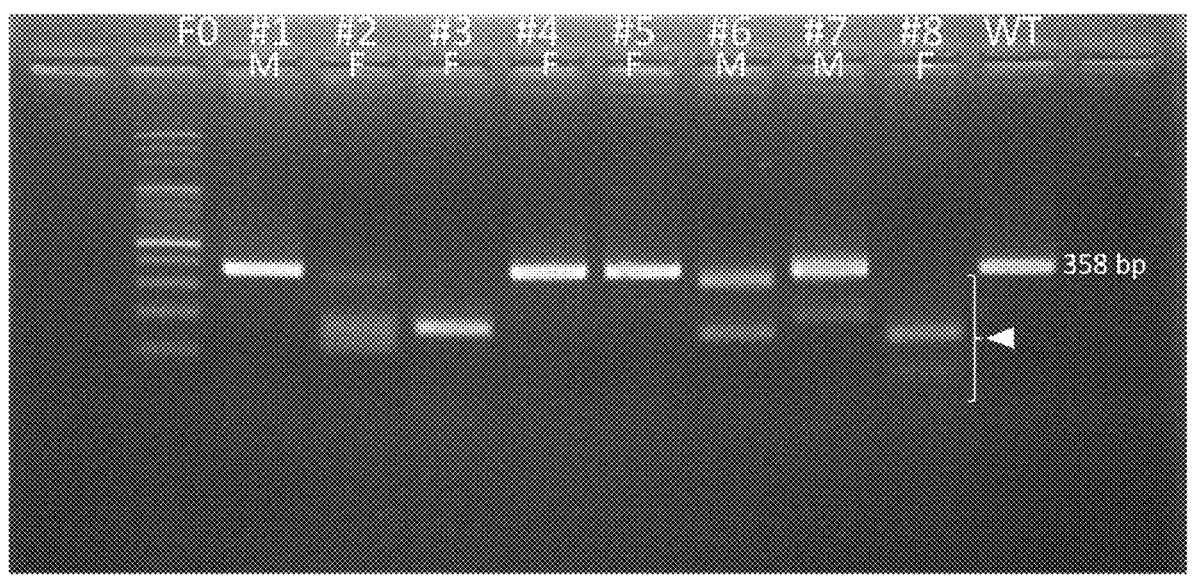
FIG. 19. The results of PCR analysis for mutations of the acrosin gene in F0 founder hamsters. For the PCR primers used, see Table S2. The white arrowhead indicates mutated alleles. F0 #2, #3, #6, #7, and #8 carried mutations. PCR products were sequenced for identification of the mutation patterns (FIG. 14C), except for #2 which showed a high level of mosaicism.

We designed six single-guide RNAs (sgRNAs) that targeted the sequences of either the 5'- or 3'-side of the catalytic domain of the hamster acrosin gene (FIG. 18 and Table 19). We injected the six sgRNAs, together with Cas9 protein, into the oviducts of four females on Day 0.5 (the day following mating) and immediately applied electric pulses to the oviducts using a forceps-like electrode (FIGS. 14A and B). On Day 15.5, the females gave birth to a total of 15 pups, eight of which were weaned. Of these, five (two females and three males) carried mutant alleles, as demonstrated by genomic polymerase chain reaction (PCR) using ear tissue (SI Appendix, FIG. 19). Genomic sequencing analysis identified six types of mutant alleles (Alleles A to F) from four founders (F0 #3, #6, #7, and #8) (FIG. 14C). We could not identify the sequence of each mutant allele in F0 #2, because of extensive mosaicism at the target region (SI Appendix, FIG. 19). We mated these four founders with wild-type (WT) hamsters and intercrossed the resultant F1 heterozygous KO hamsters to generate F2 homozygous KO hamsters. Because homozygous KO hamsters carrying Allele A originating from F0 #3 (female) were the first obtained, they were used for establishment of the acrosin-KO line (Line A) and subjected to a series of phenotypic analyses as described below.

TABLE 19

The primer sestys used for the PCT in this study.

| Name | Forward (5' to 3') | Reverse (5' to 3') |
| --- | --- | --- |
| sgRNA of CRISPR1 | TAATACGACTCACTATA GCCAGTTGTATGTAAGG | TTCTAGCTCTAAAACGC TGCCTTACATACAACTG |
| sgRNA of CRISPR2 | TAATACGACTCACTATA GCCACAGCCCCATGACC | TTCTAGCTCTAAAACGA AGGGTCATGGGGCTGTG |
| sgRNA of CRISPR3 | TAATACGACTCACTATA GAAGTGACCCCTCTGTC | TTCTAGCTCTAAAACGA AGGACAGAGGGGTCACT |
| sgRNA of CRISPR4 | TAATACGACTCACTATA GCGACAGCCCCTTTGTG | TTCTAGCTCTAAAACCG ACCACAAAGGGGCTGTC |
| sgRNA of CRISPR5 | TAATACGACTCACTATA GTGTGCCCGTGCTAAAC | TTCTAGCTCTAAAACGG ACGTTTAGCACGGGCAC |
| sgRNA of CRISPR6 | TAATACGACTCACTATA GCCACCTGGGACTACCT | TTCTAGCTCTAAAACAT CCAGGTAGTCCCAGGTG |
| Sequencing of the acrosin gene | GCCTTCACATCCCAATG GATA | AGTAGTAGTAGGCGGGG GAG |
| qRT-PCR of RABL2B | TCTCCCTGCCCCTGTAC TTT | GCCTGACCCTGCATTTG TCC |
| qRT-PCR of beta-actin | CAAGAGATGGCCACTGC CG | GTGGATGCCACAGGATT CCATA |

Biochemical Analyses of Spermatozoa

To confirm that KO spermatozoa were devoid of acrosin, we analyzed them by Western blot, using as a probe polyclonal antibody raised against the N-terminal 20-mer oligopeptide of mouse proacrosin (8). As expected, two forms of hamster (pro)acrosin with approximate sizes of 47 and 40 kDa were found only in WT spermatozoa (FIG. 14D). These two proteins displayed gelatin-hydrolyzing activity (FIG. 14E). When the serine protease activities of sperm acid extracts were measured using three t-butyloxycarbonyl (Boc)-dipeptidyl-Arg-4-methylcoumaryl-7-amide (MCA) as substrate, KO spermatozoa exhibited a negligible level of enzyme activity (FIG. 14F). Thus, these data demonstrate the absence of acrosin in KO spermatozoa.

Homozygous Acrosin-KO Males Are Completely Sterile

Heterozygous acrosin-KO males and females showed normal reproductive performance, as confirmed by their efficient production of offspring. We next examined the fertility of homozygous acrosin-KO males. Nine F2 to F4 males homozygous for acrosin mutations were mated with three WT females each for 2 weeks. Ten WT males served as controls. None of the females mated with KO males became pregnant, but all the females mated with WT males became pregnant (FIG. 14G). We obtained similar results with another KO line (Line E carrying the mutant allele E derived from F0 #8) (FIG. 14G). These results indicated that acrosin-KO males were completely sterile. Then we examined the behavior of KO spermatozoa within the female genital tract after natural mating. We found spermatozoa within the matrix of the cumulus oophorus (SI Appendix, Movie S1) and on the surface of the zona pellucida (FIG. 14H) after females were mated with acrosin-KO males. However, there were no spermatozoa within the perivitelline space. Thus, acrosin-KO spermatozoa ascended the uteri and the oviducts normally after mating but did not penetrate the oocyte zona pellucida.

Figure 15:
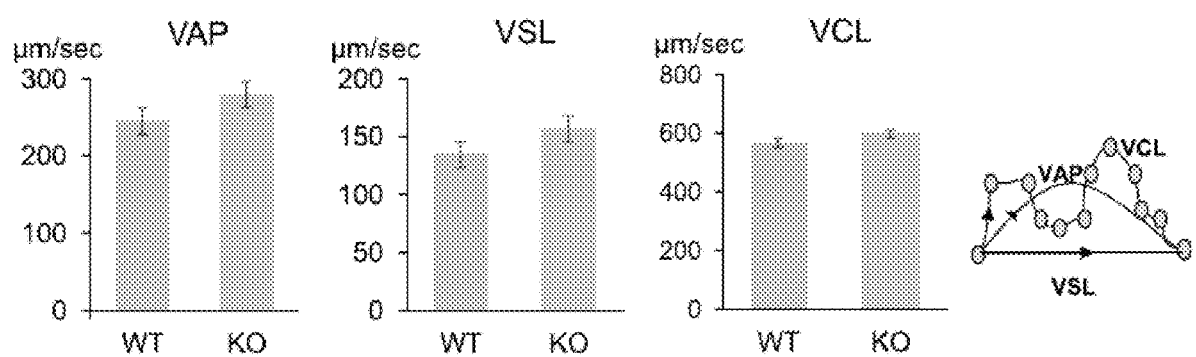
FIG. 15. Sperm motility of acrosin-KO spermatozoa. Three motility parameters of spermatozoa, VAP (average path velocity), VSL (straight-line velocity) and VCL (curvilinear velocity), were not affected by acrosin KO. For other parameters, see Table S1.
Figure 16:
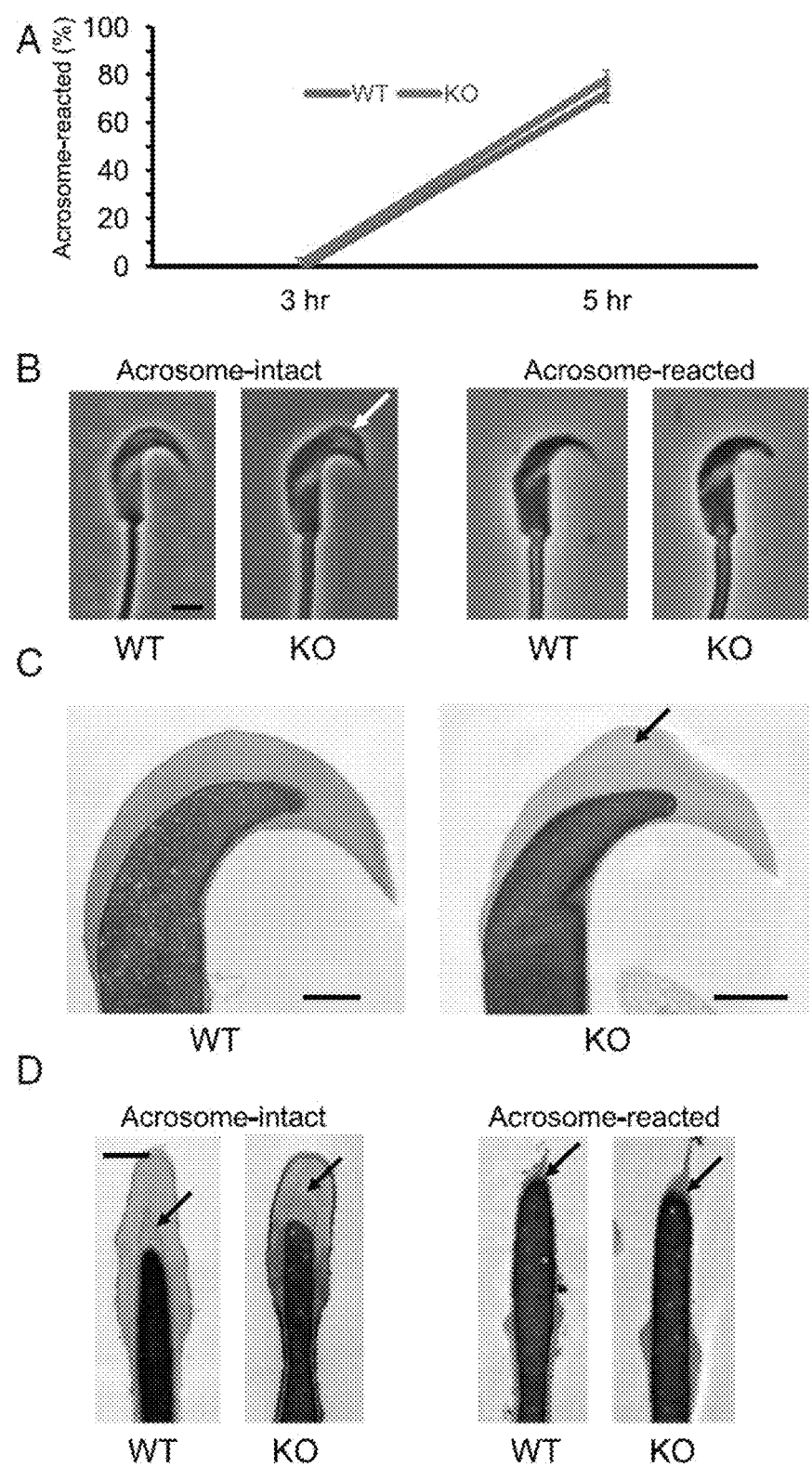
FIG. 16. The acrosomal status of normal (WT) and acrosin-KO spermatozoa. (A) The time course of the appearance of acrosome-reacted spermatozoa. Only live, motile spermatozoa were counted (51-161 sperm per observation). In both WT and KO sperm, the acrosome reaction started 3 h after the start of incubation and was completed in the majority of spermatozoa (69%-77%) by 5 h. Results of two replicate experiments expressed as mean±S.E.M. P<0.05 between the two groups at each time point. (B) Phase-contrast micrographs of spermatozoa. Acrosin-KO spermatozoa had a protrusion in the acrosome before the acrosomal reaction (arrow). Bar, 2 μm. (C) Longitudinal sections of the head of acrosome-intact spermatozoa observed by transmission electron microscopy. The protrusion on the head of the spermatozoa corresponded to a partial enlargement of the acrosome (arrow). Bar, 1 μm. (D) Sagittal section of spermatozoa before and after acrosome reaction. Both WT and acrosin-KO spermatozoa exposed the inner acrosomal membrane (arrows) after the acrosome reaction. Bar, 500 nm.

Acrosin-KO Spermatozoa Have Normal Motility and Can Undergo the Acrosome Reaction Failure of the acrosome reaction and/or poor motility of spermatozoa are common causes of male infertility. We therefore examined the behavior of the acrosin-KO spermatozoa in vitro. First, we analyzed sperm motility by computer-assisted sperm analysis (CASA) and found that acrosin-KO spermatozoa were indistinguishable from WT spermatozoa for all parameters examined (FIG. 15A, Table 20). We then examined the ability of the spermatozoa to undergo the acrosomal reaction by incubating them in acrosome reaction-inducing medium containing high concentrations of $Ca^{2+}$ (3.4 mM) and bovine serum albumin (15 mg/mL). Only live, motile spermatozoa were counted because dead spermatozoa often lose their acrosomes. In both WT and KO groups, the acrosome reaction started in a small population of spermatozoa (0%-2%) at 3 h and was complete in the majority (69%-77%) by 5 h (FIG. 16A). This implied that acrosin plays no essential role in the initiation of the acrosome reaction. The acrosome status of live hamster spermatozoa was easily determined under a phase-contrast microscope (FIG. 16B). We found that acrosin-KO spermatozoa had a protrusion in the acrosome cap region, which disappeared during the acrosome reaction (FIG. 16B). Transmission electron microscopic examination revealed that this protrusion was caused by a partial swelling of the acrosome, not by the formation of an additional space beneath the plasma membrane (FIG. 16C). Nonetheless, it did not seem to disturb the acrosome reaction because acrosome-reacted KO spermatozoa were indistinguishable from acrosome-reacted WT spermatozoa at both light microscopic (FIG. 16B) and electron microscopic levels (FIG. 16D).

TABLE 20

The sperm motility parameters assessed by computer-assisted sperm analysis.

| Parameters | WT | KO |
| --- | --- | --- |
| Motility (%) | 80.0 ± 0.8 | 81.3 ± 2.3 |
| Progressive motility (%) | 45.7 ± 0.9 | 48.3 ± 1.8 |
| Average path velocity (VAP)(μm/s) | 244.8 ± 15.7 | 279.1 ± 24.3 |
| Straight-line velocity (VSL)(μm/s) | 134.2 ± 9.6 | 156.7 ± 16.3 |
| Curvilinear velocity (VCL)(μm/s) | 567.0 ± 15.8 | 596.0 ± 27.2 |
| Amplitude of lateral head displacement (ALH)(μm) | 34.4 ± 1.3 | 36.5 ± 3.4 |
| Beat cross frequency (BCF)(Hz) | 34.0 ± 1.2 | 32.3 ± 1.5 |
| Linearity (LIN)(%) | 24.3 ± 1.2 | 26.0 ± 1.1 |
| Straightness (STR)(%) | 54.7 ± 0.7 | 54.7 ± 0.3 |

The values indicate the means±S.E.M. calculated from three replicates using different animals. The values of all parameters were not significantly different between the two groups.

Acrosin is Essential for Sperm Penetration Through the Zona

Figure 17:
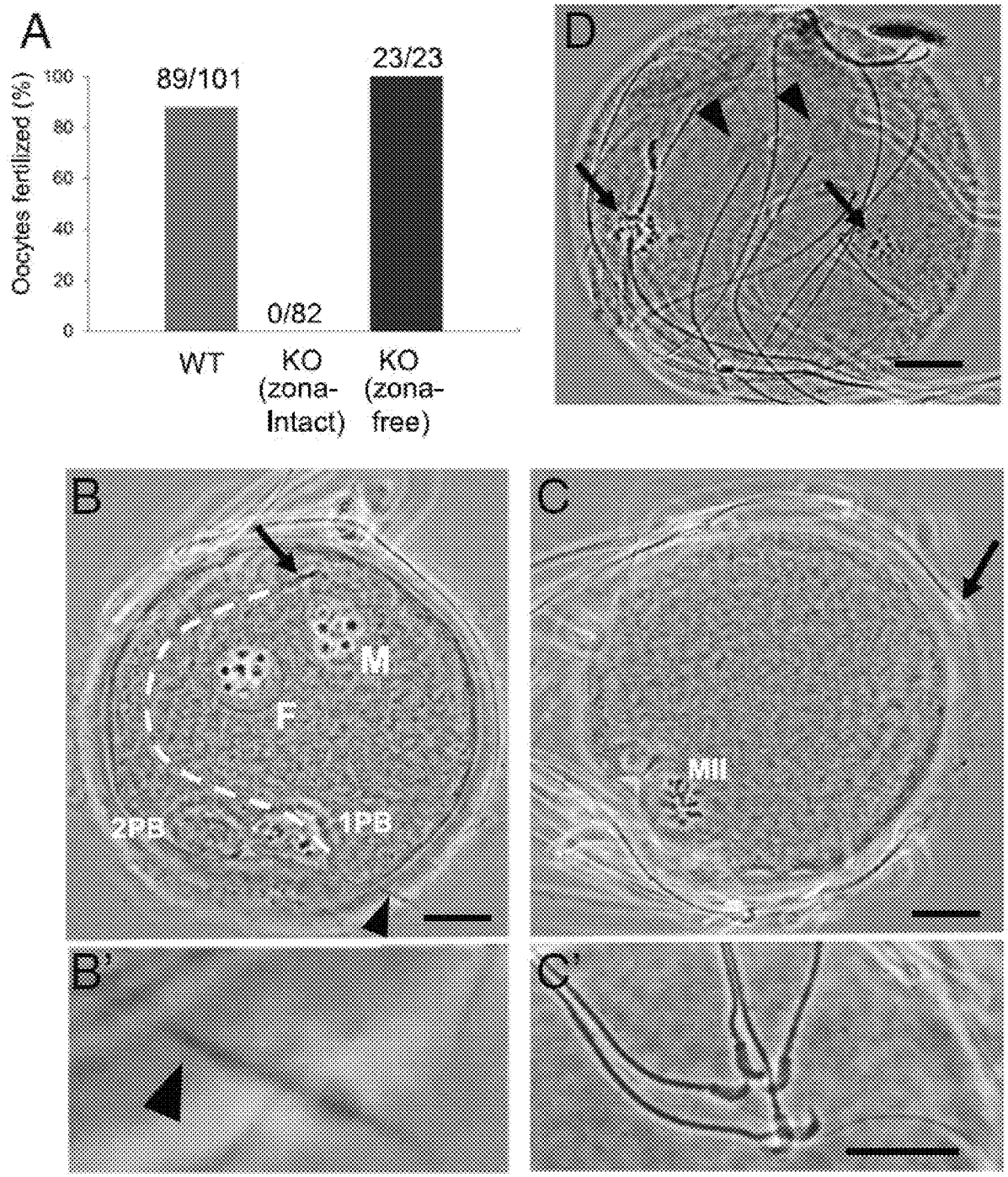
FIG. 17. Fertilizing ability of acrosin-KO spermatozoa assessed by IVF. (A) Although approximately 90% of oocytes were fertilized by WT spermatozoa, no oocytes were fertilized by acrosin-KO spermatozoa. When the zona was removed, all oocytes were fertilized by acrosin-KO spermatozoa. (B) An oocyte fertilized by WT spermatozoon. F, female pronucleus; M, male pronucleus; 1PB, first polar body; 2PB, second polar body; arrow, sperm tail in the egg cytoplasm in focus. The rest of the tail was out of focus (dotted line); tip of the sperm tail crossing the zona (arrowhead). (B') High magnification of the tip of the sperm tail seen crossing the zona in B. (C) An unfertilized oocyte inseminated with acrosin-KO spermatozoa. Spermatozoa attached to the zona but did not penetrate it (arrow). MII, metaphase II chromosomes. (C') Spermatozoa on the zona of the oocyte in C. They are all acrosome-reacted. (D) A zona-free oocyte inseminated with acrosin-KO spermatozoa. Arrows and arrowheads indicate male pronuclei and decondensing sperm heads, respectively. Bar, 20 μm.

We then analyzed the fertilizing ability of acrosin-KO spermatozoa in vitro. First, cumulus-intact oocytes were inseminated with spermatozoa that had been preincubated for 2 h. About 5 h after insemination, most oocytes (about 90%) were fertilized by WT spermatozoa, whereas none were fertilized by acrosin-KO spermatozoa (FIG. 17A-C). Acrosin-KO spermatozoa penetrated the cumulus cell layer and bound tightly to the zona pellucida in the same way as WT spermatozoa (SI Appendix, Movies S2,3), but were never found within the perivitelline space. Next, to determine whether acrosin-KO spermatozoa could fuse with the oolemma, we removed the zona before insemination with KO spermatozoa. We found that all the oocytes (n=23) were fertilized by KO spermatozoa, with multiple male pronuclei (FIG. 17A, D). This means that acrosin is essential for sperm penetration through the zona, but not for the acrosome reaction or sperm fusion with the oolemma.

Discussion

Before gene-KO technology became available, it was expected that acrosin-deficient animals would be infertile, because many acrosin inhibitors prevented fertilization in vitro (6, 18, 19). Surprisingly, acrosin-KO mouse spermatozoa were fertile both in vivo and in vitro (7). Furthermore, mice lacking two acrosomal enzymes, acrosin and PRSS21, were also fertile (20). Acrosin-KO rats also showed no distinct phenotype although they produced smaller litter sizes (10). Although these results implied that a zona lysin was unlikely to be involved in zona penetration by sperm, there was substantial evidence to support the presence of sperm-borne zona lysins; the presence of eroded holes on the zona surface near the attached spermatozoa (21) and the inability of acrosome-intact spermatozoa to penetrate the zona (22). Thus, the involvement of acrosomal enzyme(s) in sperm zona penetration has not been completely excluded. In this study, we demonstrated that in the golden hamster, acrosin is essential for sperm penetration through the zona.

Thus, the currently prevailing concept that acrosin is nonessential for fertilization in mammalian species must be reconsidered.

In general, gene-KO mice often show no obvious changes in phenotype, probably reflecting the redundancy of the particular gene function or the features of genes specific to mice. Gene KO in rats may have similar results to that in mice because of the phylogenetic closeness of the two species. By contrast, Cricetidae rodents (hamsters) diversified from Muridae rodents long before *Mus* (mouse) and *Rattus* (rat) emerged (23, 24). Therefore, if some physiological mechanisms underwent specific patterns of evolution in murine rodents, the related KO phenotypes could be different between murine rodents and other animals. Perhaps the mechanisms of fertilization are one such case. Indeed, the acrosome cap of mouse and rat spermatozoa is much smaller than those of many other rodent species (1) and acrosin-bound markers (e.g., enhanced green fluorescent protein) are necessary for clear visualization of their acrosome (25). This small acrosomal cap in mice and rats may be related to the lesser dependence of their spermatozoa on acrosin for fertilization. Interestingly, both acrosin-KO mice and rats showed a delayed sperm penetration of cumulus layers, implying that acrosin in these species functions on cumulus layers, not on the zona pellucida. By contrast, acrosin-KO hamster spermatozoa readily dispersed cumulus cells as WT spermatozoa at least in vitro. In mice, KO of many other fertilization-related factors such as hyaluronidase and fertilin also resulted in no or subtle changes to adult phenotypes (26). It is possible that hamsters and some other animals with large acrosome caps would have serious problems with fertilization when spermatozoa lack these substances.

Important questions relating to sperm acrosin are its intracellular location and its role in fertilization. In cattle and in humans, acrosin is present on the inner acrosome membrane of spermatozoa after the acrosome reaction (27, 28). Membrane-bound acrosin may well serve as a zona lysin as the sperm head advances through the zona pellucida. Although Yanagimachi and Teichman (29) and Yunes et al. (30) were unable to detect proteolytic activity on the inner acrosome membrane of acrosome-reacted hamster spermatozoa by cytochemical and immunocytochemical methods, the results of the present study have prompted us to reinvestigate this.

Our study may have broad implications in diverse fields of biology. Our hamster genome-editing system is technically easy and highly reproducible. Although the mouse KO system has contributed immeasurably to our understanding of physiology and pathology in general, it is not always perfect. We expect that KO hamsters could substitute for KO mice in the analysis of gene functions and the generation of new human disease models that have not been achieved in mice.

Materials and Methods

Animals

Golden (Syrian) hamsters purchased from Japan SLC, Inc. were housed under controlled lighting conditions (daily light period, 0700 to 2100) and provided with water and food ad libitum. All animal experiments were approved (T2019-J004) by the Animal Experimentation Committee at the RIKEN Tsukuba Institute and were performed in accordance with the committee's guiding principles.

Generation of KO Hamsters

Figure 20:
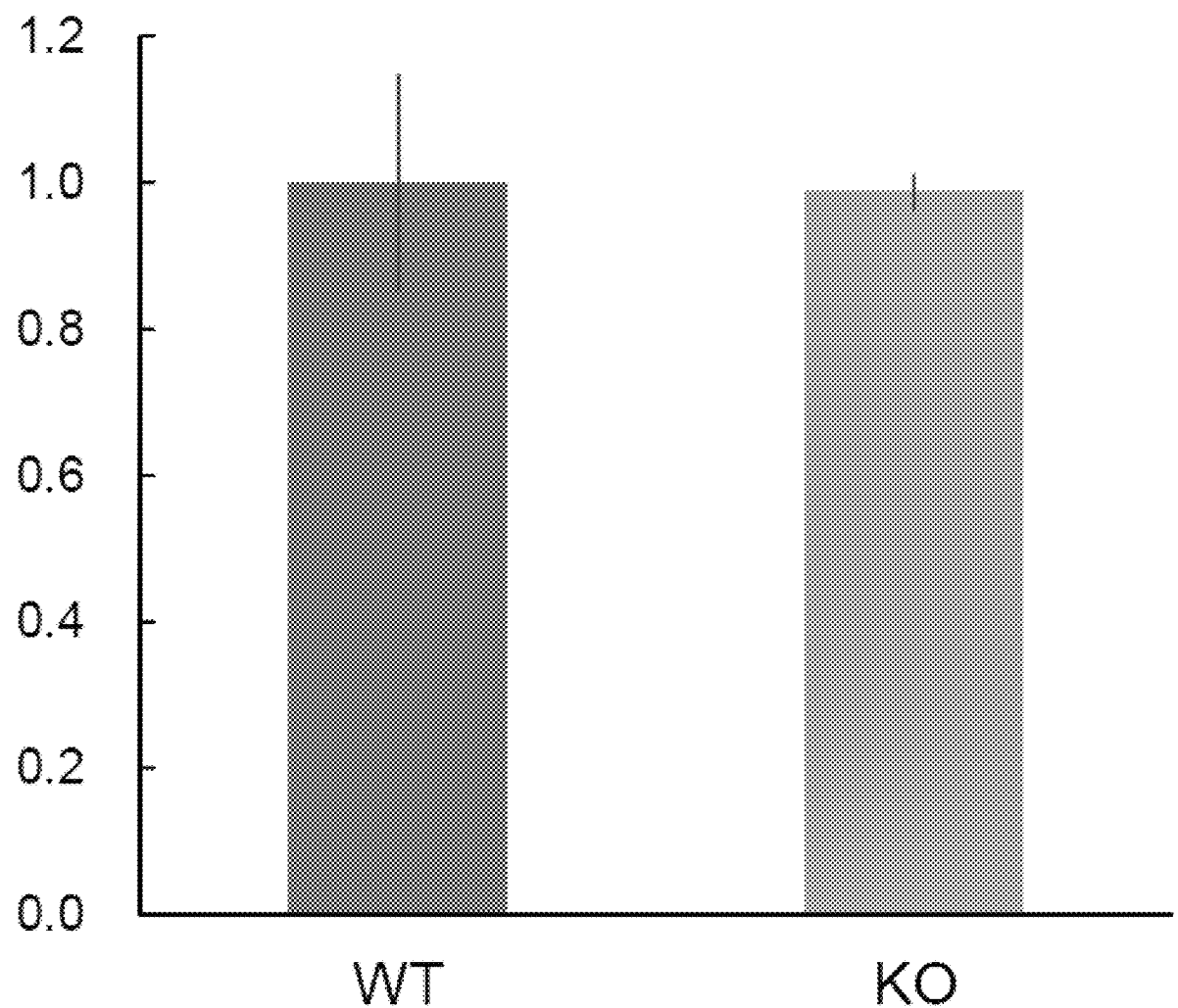
FIG. 20. Expression analysis of the RABL2B gene, which is located in the vicinity of the Acrosin gene. There was no significant difference between the two groups (P>0.05). beta-actin was used as an internal control gene. Data are expressed as the mean±standard error of the mean; n=3. The mean level of WT was set as 1.

Mature females were induced to superovulate by intraperitoneal injection of 10 IU equine chorionic gonadotropin (eCG) at 0900-1200 on the day of conspicuous, postestrus vaginal discharge (Day 1 of the estrous cycle), followed by mating with fertile males during the night of Day 4 until the next morning (Day 1 of pregnancy). The sgRNAs were designed using CRISPOR (http://crispor.tefor.net) and produced using a GeneArt Precision gRNA Synthesis Kit (# A29377; Thermo Fisher Scientific). Potential off-target sites in the golden hamster genome (MesAur1.0) were identified using the latest version of the CRIPSR Design Tool website (CRISPRdirect: http://crispr.dbcls.jp/). We confirmed that there was no potential off-target site containing 1-2 nucleotide mismatches with the 20-nt target sequence of the sgRNAs used. There is one sperm-related gene, RABL2B, in the vicinity of the Acrosin gene. This is known to be a risk factor for the fertilizing ability of spermatozoa in humans (31). We confirmed that the RABL2B expression in the testes was not affected by Acrosin gene deletion, as shown by quantitative RT-PCR using specific primers (FIG. 20 and Table 19). i-GONAD was performed as described (17). Briefly, the solution contained six sgRNAs (Table 20) and Cas9 protein (#1081059; IDT). Approximately 2.5-3.0 µL of solution was injected from the upper segment of ampulla toward the lower segments using a fine glass micropipette (FIG. 14B). After injection, the oviduct was covered with a piece of Kimwipe wetted with phosphate-buffered saline (PBS) and then pinched by a forceps-type electrode (#CUY650P5; NEPA GENE). Electroporation was performed using NEPA21 (NEPA GENE). The electroporation conditions consisted of three sequential poration pulses (500 V/cm, 50 ms duration, 5 ms intervals) followed by three transfer pulses (100 V/cm, 50 ms duration, 50 ms intervals). On Day 16 of pregnancy, fetuses were delivered naturally, and live pups were examined for CRISPR-Cas9-induced mutations at the target sites.

Identification of Mutations on the Acrosin Gene

Genomic DNA was extracted from small pieces of ear tissue from the pups. Approximately 400-bp genomic fragments containing the target site were amplified by PCR using primers (Table 19) and 0.625U of Tks Gflex (Takara Bio). PCR was performed under the following conditions: 1 cycle of 94° C. for 3 min, 35 cycles of 94° C. for 30 s, 60° C. for 30 s and 72° C. for 30 s, and 1 cycle of 72° C. for 3 min. After confirmation of an indel mutation at the target site, PCR fragments were subcloned into a pGEM T Vector system (Promega) and sequenced for the determination of each allele.

Western Blot

Freshly excised epididymides were minced in PBS. Sperm were collected by centrifugation at 3,000 rpm for 5 min and extracted on ice for 2 h in 1 mM HCl solution containing 5 mM p-aminobenzamidine (15). After centrifugation at 12,000 rpm for 10 min, the supernatant solution was dialyzed against 1 mM HCl to remove p-aminobenzamidine and used as sperm acid extracts. Proteins were separated by sodium dodecyl sulfate-polyacrylamide gel electrophoresis (SDS-PAGE) under nonreducing conditions and transferred onto Immobilon-P polyvinylidene difluoride membranes (Merck Millipore). After being blocked with 2% skim milk, the blots were incubated with affinity-purified antibody against the N-terminal 20-mer oligopeptide of mouse proacrosin (8), and then incubated with horseradish peroxidase-conjugated goat anti-rabbit IgG (Jackson ImmunoResearch Laboratories). The immunoreactive proteins were detected by an enhanced chemiluminescence Western blotting detection kit (GE Healthcare UK).

Gelatin Zymography

Proteins exhibiting gelatin-hydrolyzing activities in sperm acid extracts were visualized by SDS-PAGE in the presence of 0.1% gelatin under non-reducing conditions, as described previously (8). After electrophoresis, gels were washed twice with 0.1 M Tris/HCl, pH 8.0, containing 2.5% Triton X-100 at room temperature to remove SDS, and then incubated in the same buffer free of Triton X-100 at 37° C. overnight. The gelatin-hydrolyzing proteins were detected by staining the gels with Coomassie Brilliant Blue.

Measurement of Enzyme Activity

Proteolytic activity of acrosin in sperm acid extracts was measured using Boc-Phe-Ser-Arg-MCA, Boc-Leu-Thr-Arg-MCA, and Boc-Val-Pro-Arg-MCA as substrates (32). The reaction mixture (0.25 mL) consisted of 50 mM Tris/HCl, pH 8.0, 10 mM $CaCl_2$, 40 µM enzyme substrate (Peptide Institute), and sperm acid extracts (1 µg of protein). After incubation at 30° C. for 30 min, the reaction was terminated by addition of 0.1 M acetate buffer, pH 4.3 (0.75 mL). The amount of 7-amino-4-methylcoumarin (AMC) formed from the substrates was measured fluorometrically with excitation at 380 nm and emission at 460 nm. One unit of the enzyme activity was defined as 1 nmol of AMC formed per minute under these conditions.

IVF

Actively motile spermatozoa for IVF were collected by the swim-up method. Briefly, about 2 µL sperm mass was collected from the cauda epididymis and placed at the bottom of a 15-mL round-bottom polystyrene tube. About 2 mL of modified TALP (mTALP) medium (33), which had been equilibrated in 5% $CO_2$ at 37° C., was gently laid on the sperm mass. Approximately 2 to 3 min later, the upper 150 µL of the medium with actively motile spermatozoa was sucked up and transferred to a plastic dish, which was then covered with mineral oil. The spermatozoa were incubated for 3 h in 5% $CO_2$ at 37° C. before they were used for insemination. To collect mature unfertilized eggs, female hamsters (8-16 weeks old) were each injected with 7.5 units of eCG, followed by 7.5 units of human chorionic gonadotropin (hCG) 48 h later. Cumulus-oocyte complexes were collected from the oviducts 15 h after hCG injection and placed in 150-µL drops of mTALP medium. They were inseminated with preincubated spermatozoa and kept in 5% $CO_2$ at 37° C. The final concentration of spermatozoa in the insemination medium was approximately 150 sperm/µL. About 5 to 6 h later, the oocytes were mounted and compressed between a slide and coverslip, fixed with 2.5% glutaraldehyde in cacodylate buffer, and their nuclear status was examined as described previously (34).

Zona-Free Oocyte IVF

To induce the acrosome reaction of spermatozoa, cauda epididymal spermatozoa were preincubated in mTALP medium with higher concentrations of bovine serum albumin (15 mg/mL) and $Ca^{2+}$ (3.4 mM) for 5 to 6 h. At the end of this preincubation, about 70% of spermatozoa were acrosome-reacted and actively motile, irrespective of their genotype (FIG. 16A). Oocytes collected as described above were freed from both cumulus cells and the zona pellucida by treatment with 0.1% hyaluronidase and acid Tyrode's solution, respectively. After coculture with preincubated spermatozoa for 2.5 h, oocytes were examined for the presence or absence of the male pronucleus as described above.

Transmission Electron Microscopy of Spermatozoa

Spermatozoa were fixed in 2% paraformaldehyde and 2% glutaraldehyde in 30 mM Hepes buffer containing 100 mM NaCl and 2 mM $CaCl_2$ (pH 7.4) for >2 h at room temperature, followed by postfixation in an aldehyde-$OsO_4$ mixture (1% $OsO_4$, 1.25% glutaraldehyde, 1% paraformaldehyde, and 0.32% $K_3[Fe\{CN\}_6]$ in 30 mM Hepes buffer [pH 7.4]) for 2 h. Fixed spermatozoa were washed three times with Milli Q water and stained en bloc with 0.5% uranyl citrate for 10 min. Stained spermatozoa were centrifuged and placed in Milli-Q-water-washed citrus pulp to facilitate later handling of spermatozoa. Each aliquot of citrus pulp containing fixed spermatozoa was washed with 50% ethyl alcohol, dehydrated in an ethanol series, and dipped in epoxy resin (Quetol 812, Nisshin EM). Sperm masses dissected out of the pulp were reembedded in the same resin. Each sample was sectioned at 80-nm thickness with an ultramicrotome (EM UC7; Leica). Sections were examined in a transmission electron microscope (JEM-1400; JEOL).

Sperm Motility Analysis

Cauda epididymal spermatozoa were collected and preincubated as described above for 2 h at 37° C. in 5% $CO_2$. The overall sperm motility, progressive motility, average path velocity, straight-line velocity, curvilinear velocity, amplitude of lateral head displacement, beat cross frequency, linearity, and straightness were assessed by computer-assisted sperm analysis using a Hamilton Thorne IVOS computerized semen analyzer (Hamilton Thorne). All the parameters were measured in >200 spermatozoa in at least three different fields.

Statistical Analysis

The results from the sperm motility assay, enzyme reactivity test, and observation of the time course of the acrosome reaction were analyzed by two-way analysis of variance. The percentages were subjected to arcsine transformation before the statistical analysis. P values less than 0.05 were considered to indicate significance.

REFERENCES

1. R. Yanagimachi, "Mammalian fertilization" in The Physiology of Reproduction, N. J. Knobil E, Ed. (Raven Press, New York, 1994), pp. 189-317.
2. D. P. Green, Mammalian sperm cannot penetrate the zona pellucida solely by force. *Exp. Cell Res.* 169, 31-38 (1987).
3. A. Honda, J. Siruntawineti, T. Baba, Role of acrosomal matrix proteases in sperm-zona pellucida interactions. *Hum. Reprod. Update* 8, 405-412 (2002).
4. H. T. Mao, W. X. Yang, Modes of acrosin functioning during fertilization. *Gene* 526, 75-79 (2013).
5. A. B. Dudkiewicz, Inhibition of fertilization in the rabbit by anti-acrosin antibodies. *Gamete Res.* 8, 183-197 (1983).
6. D. Y. Liu, H. W. Baker, Inhibition of acrosin activity with a trypsin inhibitor blocks human sperm penetration of the zona pellucida. *Biol. Reprod.* 48, 340-348 (1993).

7. T. Baba, S. Azuma, S. Kashiwabara, Y. Toyoda, Sperm from mice carrying a targeted mutation of the acrosin gene can penetrate the oocyte zona pellucida and effect fertilization. *J. Biol. Chem.* 269, 31845-31849 (1994).

8. K. Yamagata, A. Honda, S. I. Kashiwabara, T. Baba, Difference of acrosomal serine protease system between mouse and other rodent sperm. *Dev. Genet.* 25, 115-122 (1999).

9. T. Mashimo, Gene targeting technologies in rats: zinc finger nucleases, transcription activator-like effector nucleases, and clustered regularly interspaced short palindromic repeats. *Dev. Growth. Differ.* 56, 46-52 (2014).

10. A. Isotani et al., A delayed sperm penetration of cumulus layers by disruption of acrosin gene in rats. *Biol. Reprod.* 97, 61-68 (2017).

11. D. Whittaker, "Hamster" in The UFAW Handbook on the Care and Management of Laboratory Animals, P. Trevor, Ed. (Blackwell Science Ltd., Oxford, 1999), vol. 1, pp. 356-366.

12. M. Hirose, A. Ogura, The golden (Syrian) hamster as a model for the study of reproductive biology: Past, present, and future. *Reprod. Med. Biol.* 18, 34-39 (2019).

13. R. Yanagimachi, M. C. Chang, Fertilization of hamster eggs in vitro. *Nature* 200, 281-282 (1963).

14. C. R. Austin, M. W. H. Bishop, Role of the rodent acrosome and perforatorium in fertilisation. *Proc. R. Soc. Lond. B. Biol. Sci.* 148, 241-248 (1958).

15. J. M. Cummins, R. Yanagimachi, Development of ability to penetrate the cumulus oophorus by hamster spermatozoa capacitated in vitro, in relation to the timing of the acrosome reaction. *Gamete Res.* 15, 187-212 (1986).

16. S. A. Schini, B. D. Bavister, Two-cell block to development of cultured hamster embryos is caused by phosphate and glucose. *Biol. Reprod.* 39, 1183-1192 (1988).

17. C. B. Gurumurthy et al., Creation of CRISPR-based germline-genome-engineered mice without ex vivo handling of zygotes by i-GONAD. *Nature Protoc.* 14, 2452-2482 (2019).

18. L. R. Fraser, p-Aminobenzamidine, an acrosin inhibitor, inhibits mouse sperm penetration of the zona pellucida but not the acrosome reaction. *J. Reprod. Fertil.* 65, 185-194 (1982).

19. H. Takano, R. Yanagimachi, U. A. Urch, Evidence that acrosin activity is important for the development of fusibility of mammalian spermatozoa with the oolemma: inhibitor studies using the golden hamster. *Zygote* 1, 79-91 (1993).

20. N. Kawano et al., Mice lacking two sperm serine proteases, ACR and PRSS21, are subfertile, but the mutant sperm are infertile in vitro. *Biol. Reprod.* 83, 359-369 (2010).

21. A. Jedlicki, C. Barros, Scanning electron microscope study of in vitro prepenetration gamete interactions. *Gamete Res.* 11, 121-131 (1985).

22. N. Inoue, Y. Satouh, M. Ikawa, M. Okabe, R. Yanagimachi, Acrosome-reacted mouse spermatozoa recovered from the perivitelline space can fertilize other eggs. *Proc. Natl. Acad. Sci. U.S.A.* 108, 20008-20011 (2011).

23. S. Blanga-Kanfi et al., Rodent phylogeny revised: analysis of six nuclear genes from all major rodent clades. *BMC Evol. Biol.* 9, 71 (2009).

24. J. Michaux, A. Reyes, F. Catzeflis, Evolutionary history of the most speciose mammals: molecular phylogeny of muroid rodents. *Mol. Biol. Evol.* 18, 2017-2031 (2001).

25. T. Nakanishi et al., Real-time observation of acrosomal dispersal from mouse sperm using GFP as a marker protein. *FEBS Lett.* 449, 277-283 (1999).

26. M. Okabe, Mechanisms of fertilization elucidated by gene-manipulated animals. *Asian J. Androl.* 17, 646-652 (2015).

27. M. Ferrer et al., MMP2 and acrosin are major proteinases associated with the inner acrosomal membrane and may cooperate in sperm penetration of the zona pellucida during fertilization. *Cell Tissue Res.* 349, 881-895 (2012).

28. J. Tesarik, J. Drahorad, J. Peknicova, Subcellular immunochemical localization of acrosin in human spermatozoa during the acrosome reaction and zona pellucida penetration. *Fertil. Steril.* 50, 133-141 (1988).

29. R. Yanagimachi, R. J. Teichman, Cytochemical demonstration of acrosomal proteinase in mammalian and avian spermatozoa by a silver proteinate method. *Biol. Reprod.* 6, 87-97 (1972).

30. R. Yunes, J. Melendez, M. Valdivia, C. Barros, Golden hamster perivitelline spermatozoa do not show proacrosin/acrosin at the inner acrosomal membrane. *Biol. Res.* 25, 91-93 (1992).

31. Hosseini S H, Sadighi Gilani M A, Meybodi A M, Sabbaghian M. The impact of RABL2B gene (rs144944885) on human male infertility in patients with oligoasthenoteratozoospermia and immotile short tail sperm defects. *J Assist Reprod Genet* 34, 505-10 (2017).

32. A. Honda, K. Yamagata, S. Sugiura, K. Watanabe, T. Baba, A mouse serine protease TESP5 is selectively included into lipid rafts of sperm membrane presumably as a glycosylphosphatidylinositol-anchored protein. *J. Biol. Chem.* 277, 16976-16984 (2002).

33. B. D. Bavister, R. Yanagimachi, The effects of sperm extracts and energy sources on the motility and acrosome reaction of hamster spermatozoa in vitro. *Biol. Reprod.* 16, 228-237 (1977).

34. K. Yanagida, R. Yanagimachi, S. D. Perreault, R. G. Kleinfeld, Thermostability of sperm nuclei assessed by microinjection into hamster oocytes. *Biol. Reprod.* 44, 440-447 (1991).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for germline genome engineering in a subject having a reproductive organ containing a fertilized zygote comprising:
   (a) isolating or obtaining the reproductive organ from the subject after a time period of about 12 hours to about 16.8 hours following insemination of the subject;
   (b) introducing a reagent composition into the reproductive organ, the reagent composition comprising a nuclease system and/or an exogenous polynucleotide; and
   (c) electroporating the reproductive organ, wherein during electroporation, the reproductive organ contains the fertilized zygote,
   wherein the reproductive organ is electroporated using an electroporator using the following parameters selected from the group consisting of:
   A) poring pulse: 50 V, 5-ms pulse, 50-ms pulse interval, 3 pulse, 10% decay (±pulse orientation) and transfer pulse: 10 V, 50-ms pulse, 50-ms pulse interval, 3 pulse, 40% decay(+pulse orientation) and
   B) square (mA), (+/−), Pd V: 60 V or 80 V, Pd A: 150 mA, Pd on: 5.00 ms, Pd off: 50 ms, Pd N: 3, Decay: 10%, Decay Type: Log.

2. The method of claim 1, wherein the nuclease system comprises an RNA-programmable nuclease polypeptide and a guide RNA polynucleotide.

3. The method of claim 2, wherein the RNA-programmable nuclease polypeptide comprises a Cas9 polypeptide and the guide RNA comprises a crRNA and a tracrRNA.

4. The method of claim 2, wherein the RNA-programmable nuclease polypeptide comprises a Cpf1 polypeptide.

5. The method of claim 1, wherein the reagent composition further comprises a single-stranded DNA (ssDNA) repair template.

6. The method of claim 1, wherein the subject is inseminated by mating the subject with another subject.

7. The method of claim 1 wherein the subject is a rodent.

8. The method of claim 1, wherein the reproductive organ is an oviduct.

9. The method of claim 8, wherein the reagent composition is introduced into the oviduct by injecting the reagent composition into the lumen of the oviduct.

10. The method of claim 1, wherein the time period is about 12 hours.

11. The method of claim 1, wherein the time period is about 16.8 hours.

* * * * *

UNITED STATES PATENT AND TRADEMARK OFFICE
CERTIFICATE OF CORRECTION

| | |
|---|---|
| PATENT NO. | : 11,732,273 B2 |
| APPLICATION NO. | : 16/799398 |
| DATED | : August 22, 2023 |
| INVENTOR(S) | : Channabasavaiah Gurumurthy et al. |

It is certified that error appears in the above-identified patent and that said Letters Patent is hereby corrected as shown below:

In the Specification

Column 30, Line 63, "foxed" should be --floxed--.

Column 30, Line 64, "he" should be --the--.

Column 35, Line 49, "C57BL/6NCrbl" should be --C57BL/6NCrl--.

Signed and Sealed this
Twenty-first Day of November, 2023

Katherine Kelly Vidal
*Director of the United States Patent and Trademark Office*